(12) United States Patent
Dhar et al.

(10) Patent No.: US 7,943,617 B2
(45) Date of Patent: May 17, 2011

(54) HETEROBICYCLIC COMPOUNDS USEFUL AS KINASE INHIBITORS

(75) Inventors: T. G. Murali Dhar, Newtown, PA (US); Stephen T. Wrobleski, Whitehouse Station, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 516 days.

(21) Appl. No.: 11/940,382

(22) Filed: Nov. 15, 2007

(65) Prior Publication Data
US 2008/0275052 A1 Nov. 6, 2008

Related U.S. Application Data

(60) Provisional application No. 60/861,168, filed on Nov. 27, 2006.

(51) Int. Cl.
A01N 43/58 (2006.01)
A01N 43/60 (2006.01)
A61K 31/50 (2006.01)
A61K 31/495 (2006.01)
C07D 471/00 (2006.01)
C07D 487/00 (2006.01)
C07D 491/00 (2006.01)
C07D 495/00 (2006.01)
C07D 497/00 (2006.01)

(52) U.S. Cl. ........................ 514/249; 544/350
(58) Field of Classification Search ............... None
See application file for complete search history.

(56) References Cited

U.S. PATENT DOCUMENTS

| | | | |
|---|---|---|---|
| 4,810,496 A * | 3/1989 | Jensen | 424/646 |
| 5,658,903 A | 8/1997 | Adams et al. | |
| 5,932,576 A | 8/1999 | Anantanarayan et al. | |
| 5,945,418 A | 8/1999 | Bemis et al. | |
| 5,977,103 A | 11/1999 | Adams et al. | |
| 6,087,496 A | 7/2000 | Anantanarayan et al. | |
| 6,130,235 A | 10/2000 | Mavunkel et al. | |
| 6,147,080 A | 11/2000 | Bemis et al. | |
| 6,251,914 B1 | 6/2001 | Adams et al. | |
| 6,277,989 B1 | 8/2001 | Chakravarty et al. | |

FOREIGN PATENT DOCUMENTS

| | | |
|---|---|---|
| WO | WO 00/12074 | 3/2000 |
| WO | WO 00/12497 | 3/2000 |
| WO | WO 00/56738 | 9/2000 |
| WO | WO 01/27089 | 4/2001 |
| WO | WO 01/34605 | 5/2001 |

OTHER PUBLICATIONS

Henry, J.R. et al., "p38 mitogen-activated protein kinase as a target for drug discovery", Drugs of the Future, vol. 24, No. 12, pp. 1345-1354 (1999).
Moreland, L.W. et al., "Etanercept Therapy in Rheumatoid Arthritis: A Randomized, Controlled Trial", Annals of Internal Medicine, vol. 130, No. 6, pp. 478-486 (1999).
Rankin, E.C.C. et al., "The Therapeutic Effects of an Engineered Human Anti-Tumor Necrosis Factor Alpha Antibody (CDP571) in Rheumatoid Arthritis", British Journal of Rheumatology, vol. 34, pp. 334-342 (1995).
Salituro, F.G. et al., "Inhibitors of p38 MAP Kinase: Therapeutic Intervention in Cytokine-Mediated Diseases", Current Medicinal Chemistry, vol. 6, No. 9, pp. 807-823 (1999).

* cited by examiner

Primary Examiner — James O Wilson
Assistant Examiner — Jeffrey H Murray
(74) Attorney, Agent, or Firm — Laurelee A. Duncan

(57) ABSTRACT

A compound of Formula (I)

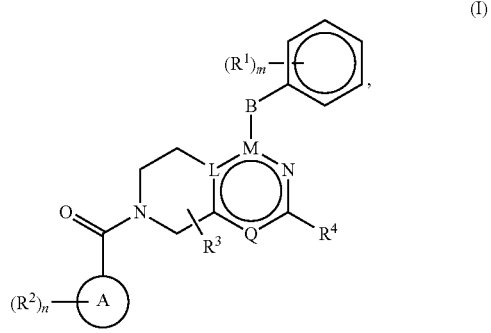

and enantiomers, diastereomers and pharmaceutically-acceptable salts thereof. Also disclosed are pharmaceutical compositions containing compounds of Formula I, and methods of treating conditions associated with the activity of p38 kinase.

4 Claims, No Drawings

HETEROBICYCLIC COMPOUNDS USEFUL AS KINASE INHIBITORS

This application claims priority to U.S. Provisional Patent Application Ser. No. 60/861,168 filed Nov. 27, 2006, which is hereby incorporated by reference in its entirety.

FIELD OF THE INVENTION

This invention relates to heterobicyclic compounds useful for treating kinase-associated conditions, such as p38 kinase-associated conditions. The invention further pertains to pharmaceutical compositions containing at least one compound according to the invention useful for treating kinase-associated conditions, such as p38 kinase-associated conditions, and methods of inhibiting the activity of kinase in a mammal.

BACKGROUND OF THE INVENTION

A large number of cytokines participate in the inflammatory response, including IL-1, IL-6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., *Drugs Fut.*, 24:1345-1354 (1999); Salituro et al., *Curr. Med. Chem.*, 6:807-823 (1999)]. Evidence in human patients indicates that protein antagonists of cytokines are effective in treating chronic inflammatory diseases, such as, for example, monoclonal antibody to TNF-α (Enbrel) [Rankin et al., *Br. J. Rheumatol.*, 34:334-342 (1995)], and soluble TNF-α receptor-Fc fusion protein (Etanercept) [Moreland et al., *Ann. Intern. Med.*, 130:478-486 (1999)].

The biosynthesis of TNF-α occurs in many cell types in response to an external stimulus, such as, for example, a mitogen, an infectious organism, or trauma. Important mediators of TNF-α production are the mitogen-activated protein (MAP) kinases, and in particular, p38 kinase. These kinases are activated in response to various stress stimuli, including, but not limited to, proinflammatory cytokines, endotoxin, ultraviolet light, and osmotic shock.

One important MAP kinase is p38 kinase, also known as cytokine suppressive anti-inflammatory drug binding protein (CSBP) or IK. Activation of p38 requires dual phosphorylation by upstream MAP kinase kinases (MKK3 and MKK6) on threonine and tyrosine within a Thr-Gly-Tyr motif characteristic of p38 isozymes. There are four known isoforms of p38, i.e., p38α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has proven that such inhibitors are effective in treating those diseases. Accordingly, the p38 enzymes serve an important role in inflammatory processes mediated by IL-1 and TNF-α.

Compounds that reportedly inhibit p38 kinase and cytokines, such as IL-1 and TNF-α for use in treating inflammatory diseases, are disclosed in U.S. Pat. Nos. 6,277,989 and 6,130,235 to Scios, Inc; U.S. Pat. Nos. 6,147,080 and 5,945,418 to Vertex Pharmaceuticals, Inc.; U.S. Pat. Nos. 6,251,914, 5,977,103 and 5,658,903 to Smith-Kline Beecham Corp.; U.S. Pat. Nos. 5,932,576 and 6,087,496 to G. D. Searle & Co.; PCT Publication Numbers WO 00/56738 and WO 01/27089 to Astra Zeneca; WO 01/34605 to Johnson & Johnson; WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

The present invention provides certain heterobicyclic compounds useful as kinase inhibitors, particularly kinases p38α and β. Each of the patent applications, patents, and publications referred to herein is incorporated herein by reference as to the subject matter referenced.

SUMMARY OF THE INVENTION

The instant invention generally pertains to compounds of Formula (I),

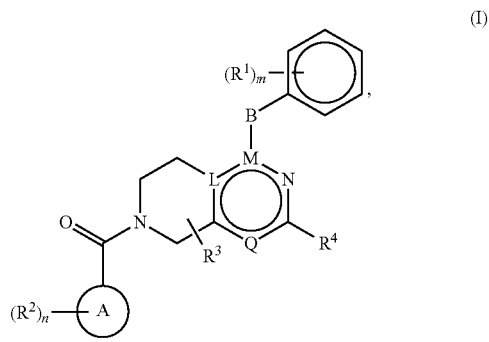

(I)

and enantiomers, diastereomers and pharmaceutically-acceptable salts thereof, wherein:

L and M are each independently selected from —N— and —C= wherein both L and M cannot be —N— at the same time;

Q is selected from the group consisting of —N—, —C=, and a bond, wherein:
(a) Q is a bond when L is —N— and M is —C=;
(b) Q is a bond when L is —C= and M is —N—; and
(c) Q is —N= or —C= when L and M are both —C=;

$R^1$ and $R^2$ are each independently selected at each occurrence from the group consisting of hydroxyl, halo, haloalkyl, optionally substituted amino, optionally substituted alkoxy, optionally substituted alkyl, optionally substituted alkenyl, optionally substituted alkynyl, optionally substituted cycloalkyl, optionally substituted heterocyclo, optionally substituted benzyl, optionally substituted benzoyl, optionally substituted aryl, optionally substituted heteroaryl, optionally substituted carbamoyl and —[C(O)]$_2$NR$^7$R$^8$, wherein each of $R^7$ and $R^8$ is independently an optionally substituted $C_{1-6}$ alkyl, and further wherein $R^7$ and $R^8$ can be taken together with the atoms to which they are attached to form an optionally substituted 5-6 member ring;

$R^3$ and $R^4$ are each independently selected from the group consisting of hydrogen, hydroxyl, halo, haloalkyl, optionally substituted amino, optionally substituted alkyl, optionally substituted alkenyl, optionally substituted alkynyl, optionally substituted cycloalkyl, optionally substituted heterocyclo, optionally substituted benzyl, optionally substituted benzoyl, optionally substituted aryl, and optionally substituted heteroaryl; CO$_2$R$^{11}$, CONR$^{11}$R$^{12}$ and NR$^{11}$R$^{12}$, wherein each of $R^{11}$ and $R^{12}$ are independently selected from the group consisting of H, C1-C6 straight or branched chain alkyl, C1-C4 straight or branched chain alkyl amino, C1-C4 straight or branched chain dialkyl amino, C1-C4 straight or branched chain alkyl with an OH group, and C4-C10 heterocyclo with 1-3 members selected from the group consisting of N, S and O; provided there are no O—O or S—S bonds in $R^3$ and $R^4$ and any of the heterocyclo groups can be optionally substituted with a member of the group consisting of C1-C4 alkyl, optionally substituted amino, and alkyl amino;

ring A is aryl or heteroaryl;

B is —$(CR^5R^6)_q$— wherein $R^5$ and $R^6$ are each independently selected from the group consisting of hydrogen and optionally substituted alkyl;

m is 0-2, wherein when m=2 (so that there are 2 $R^1$ groups (which may be the same or different) off the phenyl ring, then (a) the 2 $R^1$ groups can be separate substituents or (b) the 2 $R^1$ groups, together with the carbons to which they are attached can form a fused ring, wherein (a) and (b) can each optionally be substituted with a member selected from the group consisting of cycloalkyl, benzyl, benzoyl, aryl, heterocyclo and heteroaryl; and n and q are each independently 0-3, more particularly 0-2.

More particular values for the groups are as follows:

$R^1$ is selected from the group consisting of hydrogen, halo, C1-C6 alkyl, cyano and haloalkyl, wherein the haloalkyls have 1-3 carbons and 1-5 halogens (for example, $CF_3$, $CH_2CF_3$, and $CF_2CH_3$);

$R^2$ is selected from the group consisting of hydrogen; hydroxyl; halo; haloalkyl wherein the haloalkyls have 1-3 carbons and 1-5 halogens (for example, $CF_3$, $CH_2CF_3$, and $CF_2CH_3$); C1-C6 alkoxy; cyano; optionally substituted C1-C4 alkyl; C3-C6 cycloalkyl; heterocyclo (for example, having 4-12 carbon atoms and 1-5 members selected from the group consisting of nitrogen, oxygen, sulfur, provided that no O—O or S—S bonds are present in the ring); aryl selected from phenyl and naphthyl; heteroaryl selected from pyridyl, thiophene, thiazole, indole, indazole, azaindole, quinoline, thiazole, benzthiazole, benzofuran and benzimidazole; and —$[C(O)]_2NR^7R^8$, wherein each of $R^7$ and $R^8$ is independently selected to be H or an optionally substituted $C_{1-6}$ alkyl, or $R^7$ and $R^8$ can be taken together (with the carbons to which they are attached) to form an optionally substituted (for example, C1-C4 alkyl or hydroxyl) 5-6 membered ring;

$R^3$ is selected from the group consisting of hydrogen and C1-C3 alkyl;

$R^4$ is selected from the group consisting of hydrogen; hydroxyl; halo; haloalkyl wherein the haloalkyls have 1-3 carbons and 1-5 halogens (for example, $CF_3$, $CH_2CF_3$, and $CF_2CH_3$); $CO_2R^{11}CONR^{11}R^{12}$ or $NR^{11}R^{12}$ wherein each of $R^{11}$ and $R^{12}$ are independently selected from the group consisting of H, C1-C6 straight or branched chain alkyl, C1-C4 straight or branched chain alkyl amino, C1-C4 straight or branched chain dialkyl amino, C1-C4 straight or branched chain alkyl with an OH group, C4-C10 heterocyclo with 1-3 members selected from the group consisting of N, S and O, provided there is no O—O or S—S bonds in the ring and the heterocyclo group can be optionally substituted with C1-C4 alkyl optionally substituted amino and alkyl amino;

B is —$(CR^5R^6)_q$— wherein $R^5$ and $R^6$ are each independently selected from the group consisting of H and optionally substituted C1-C4 alkyl, wherein the substitutions are selected from the group consisting of, for example, H and $CH_3$; ring A is a aryl or heteroaryl selected from the group consisting of phenyl, naphthyl, pyridyl, thiophene, indole, indazole, azaindole, quinoline, thiazole, benzthiazole, benzofuran and benzimidazole;

m is 0-2;

n is 0-2; and q is 0-2.

The invention further pertains to pharmaceutical compositions containing compounds of Formula (I), and to methods of treating conditions associated with the activity of kinase, such as p38 (α and β), comprising administering to a mammal a pharmaceutically-acceptable amount of a compound of Formula (I).

DETAILED DESCRIPTION OF THE INVENTION

Listed below are definitions of various terms used to describe this invention. These definitions apply to the terms as they are used throughout this specification, unless otherwise limited in specific instances, either individually or as part of a larger group.

The terms "alkyl" and "alk" refers to a straight or branched chain alkane (hydrocarbon) radical containing from 1 to 12 carbon atoms, preferably 1 to 6 carbon atoms. Exemplary groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like.

"Substituted alkyl" refers to an alkyl group substituted with one or more substituents, preferably 1 to 4 substituents, at any available point of attachment on the alkyl straight or branched chain. Exemplary substituents include one or more of the following groups: halo (e.g. a single halo substituent or multiple halo substituents forming, in the latter case, groups such as a perfluoroalkyl group or an alkyl group bearing $Cl_3$ or $CF_3$), nitro, cyano, hydroxy, alkoxy, haloalkoxy (e.g., trifluoromethoxy), —O-aryl, —O-heterocyclo, —O-alkylene-aryl, —O-haloalkyl, alkylthio, carboxy (i.e., —COOH), alkoxycarbonyl, alkylcarbonyloxy, carbamoyl, substituted carbamoyl, carbamate, substituted carbamate, urea, substituted urea, amidinyl, substituted amidinyl, aryl, heterocycle, cycloalkyl, —$NR^cR^d$, —$OC(=O)NR^cR^d$, —$C(=O)NR^cR^d$, —$NR^eC(=O)NR^cR^d$, —$NR^cC(O)^2$—$NR^cR^d$, —$N(R^e)S(O)_2NR^cR^d$, —$N(R^e)P(O)_2NR^cR^d$, (wherein each of $R^c$ and $R^d$ is independently selected from hydrogen, alkyl, aryl, and heterocyclo, and $R^e$ is hydrogen, alkyl, or phenyl); and —$SR^f$, —$S(=O)R^g$, —$S(O)_2R^g$, —$NR^eS(O)_2$—$R^g$, —$P(O)_2$—$R^g$, —$NR^eC(=O)R^f$, —$NR^eC(O)_2R^f$, —$OC(=O)R^f$, —$OC(=O)OR^f$, —$C(=O)OR^f$ or —$C(=O)R^f$ (wherein $R^e$ is defined as immediately above, $R^f$ is hydrogen, alkyl, aryl or heterocyclo, and $R^g$ is alkyl, aryl, or heterocyclo). In the aforementioned substituents, in each instance, the alkyl, aryl, heterocyclo or cycloalkyl groups ($R^c$, $R^d$, $R^e$, $R^f$, and $R^g$) in turn can be optionally substituted with one to four, preferably one to three further groups, selected from $R^k$, —O—$R^k$, cyano, nitro, haloalkyl, haloalkoxy, halo, —$NR^kR^m$, —$OC(=O)NR^kR^m$, —$C(=O)NR^kR^m$, —$NR^kC(=O)R^m$, —$SR^k$, —$S(=O)R^n$, —$S(O)_2R^n$, —$OC(=O)R^k$, —$C(=O)OR^k$, —$C(=O)R^k$, phenyl, benzyl, phenyloxy, or benzyloxy, or a lower alkyl substituted with one to two of —O—$R^k$, cyano, nitro, haloalkyl, haloalkoxy, halo, —$NR^kR^m$, —$OC(=O)NR^kR^m$, —$C(=O)NR^kR^m$, —$NR^kC(=O)R^m$, —$SR^k$, —$S(=O)R^n$, —$S(O)_2R^n$, —$OC(=O)R^k$, —$C(=O)OR^k$, —$C(=O)R^k$, phenyl, benzyl, phenyloxy, or benzyloxy, wherein $R^k$ and $R^m$ are selected from hydrogen, lower alkyl, hydroxy(lower alkyl), halo(lower alkyl), cyano(lower alkyl), and amino (lower alkyl), and $R^n$ is lower alkyl.

As used herein, "alkylene" refers to a bivalent alkyl radical having the general formula —$(CH_2)_n$—, where n is 1 to 10. Non-limiting examples include methylene, dimethylene, trimethylene, tetramethylene, pentamethylene, and hexamethylene. The term "lower alkylene" herein refers to those alkylene groups having from about 1 to about 6 carbon atoms. "Substituted alkylene" refers to an alkylene group substituted with one or more substituents, preferably 1 to 4 substituents, at any available point of attachment. Exemplary substituents include, but are not limited to alkyl, substituted alkyl, and those groups recited above as exemplary alkyl substituents.

When the term alkyl is used as a subscript following another particularly-named group, as in "arylalkyl", "substituted arylalkyl", "cycloalkylalkyl", etc., or as in hydroxy (lower alkyl), this refers to an alkyl group having one or two (preferably one) substituents selected from the other, particularly-named group. Thus, for example, arylalkyl includes benzyl, biphenyl and phenylethyl. A "substituted arylalkyl" will be substituted on the alkyl portion of the radical with one or more groups selected from those recited above for alkyl, and/or will be substituted on the aryl portion of the radical with one or more groups selected from those recited below for substituted aryl.

The term "alkenyl" refers to a straight or branched chain hydrocarbon radical containing from 2 to 12 carbon atoms and at least one carbon-carbon double bond. Exemplary groups include ethenyl or allyl. "Substituted alkenyl" refers to an alkenyl group substituted with one or more substituents, preferably 1 to 4 substituents, at any available point of attachment. Exemplary substituents include, but are not limited to, alkyl, substituted alkyl, and those groups recited above as exemplary alkyl substituents.

The term "alkenylene" refers to a straight or branched chain bivalent hydrocarbon radical containing from 2 to 12 carbon atoms and at least one carbon-carbon double bond. Exemplary groups include ethenylene or allylene. "Substituted alkenylene" refers to an alkenylene group substituted with one or more substituents, preferably 1 to 4 substituents, at any available point of attachment. Exemplary substituents include, but are not limited to, alkyl, substituted alkyl, and those groups recited above as exemplary alkyl substituents.

The term "alkynyl" refers to a straight or branched chain hydrocarbon radical containing from 2 to 12 carbon atoms and at least one carbon to carbon triple bond. Exemplary groups include ethynyl. "Substituted alkynyl" refers to an alkynyl group substituted with one or more substituents, preferably 1 to 4 substituents, at any available point of attachment. Exemplary substituents include, but are not limited to, alkyl, substituted alkyl, and those groups recited above as exemplary alkyl substituents.

The term "alkynylene" refers to a straight or branched chain bivalent hydrocarbon radical containing from 2 to 12 carbon atoms and at least one carbon to carbon triple bond. Exemplary groups include ethynylene. "Substituted alkynylene" refers to an alkynylene group substituted with one or more substituents, preferably 1 to 4 substituents, at any available point of attachment. Exemplary substituents include, but are not limited to, alkyl, substituted alkyl, and those groups recited above as exemplary alkyl substituents.

The term "cycloalkyl" refers to a fully saturated cyclic hydrocarbon group containing from 1 to 3 rings and 3 to 8 carbons per ring. Exemplary groups include cyclopropyl, cyclobutyl, cyclopentyl, and cyclohexyl. The term "cycloalkyl" also includes groups having a carbon-carbon bridge of one to two bridgehead carbon atoms, and bicyclic and tricyclic groups in which at least one of the rings is a saturated, carbon-containing ring, in which case the second or third ring may be carbocyclic or heterocyclic, provided that the point of attachment is to the cycloalkyl group. The further rings may be attached to the saturated, carbon-containing ring in a spiro or fused fashion. "Substituted cycloalkyl" refers to a cycloalkyl group substituted with one or more substituents, preferably 1 to 4 substituents, at any available point of attachment. Exemplary substituents include, but are not limited to, alkyl, substituted alkyl, oxo($=$O), and those groups recited above as exemplary alkyl substituents.

The term "cycloalkylene" refers to a bivalent cycloalkyl group as defined above. Exemplary groups include cyclopropylene, cyclobutylene, cyclopentylene and cyclohexylene. "Substituted cycloalkylene" refers to a cycloalkylene group substituted with one or more substituents, preferably 1 to 4 substituents, at any available point of attachment selected from those recited for substituted cycloalkyl. The term "cycloalkenyl" refers to a partially unsaturated cyclic hydrocarbon group containing 1 to 3 rings and 4 to 8 carbons per ring. Exemplary groups include cyclobutenyl, cyclopentenyl, and cyclohexenyl. The term "cycloalkenyl" also includes bicyclic and tricyclic groups in which at least one of the rings is a partially unsaturated, carbon-containing ring and the second or third ring may be carbocyclic or heterocyclic, provided that the point of attachment is to the cycloalkenyl group. "Substituted cycloalkenyl" refers to a cycloalkenyl group substituted with one or more substituents, preferably 1 to 4 substituents, at any available point of attachment selected from those recited above for cycloalkyl groups.

The term "cycloalkenylene" refers to a bivalent cycloalkenyl group, as defined above. Exemplary groups include cyclobutenylene, cyclopentenylene, and cyclohexenylene. "Substituted cycloalkenylene" refers to a cycloalkenylene group substituted with one or more substituents, preferably 1 to 4 substituents, at any available point of attachment, selected from those recited for substituted cycloalkyl.

The terms "alkoxy" or "alkylthio" refer to an alkyl group as described above bonded through an oxygen linkage (—O—) or a sulfur linkage (—S—), respectively. The terms "substituted alkoxy" or "substituted alkylthio" refer to a substituted alkyl group as described above bonded through an oxygen or sulfur linkage, respectively. "Thiol" refers to —SH.

The term "alkoxycarbonyl" refers to an alkoxy group bonded through a carbonyl group (i.e., —C($=$O)—O-alkyl).

The term "alkylcarbonyl" refers to an alkyl group bonded through a carbonyl group (i.e., —C($=$O)alkyl).

The term "alkylcarbonyloxy" refers to an alkylcarbonyl group bonded through an oxygen linkage (i.e., —O—C($=$O)-alkyl).

The term "amido" refers to the group —NHC($=$O)H, and amidinyl refers to the group —C($=$NH)(NH$_2$). A "substituted amido" refers to the group —NR$^p$C($=$O)R$^q$, and a "substituted amidinyl" refers to the group —C($=$NR$^p$)(NR$^q$R$^r$), wherein R$^p$, R$^q$, and R$^r$ are selected from hydrogen, alkyl, substituted alkyl, cycloalkyl, substituted cycloalkyl, aryl, substituted aryl, heterocyclo, and substituted heterocyclo, provided that at least one of R$^p$, R$^q$, and R$^r$ is other than hydrogen.

The term "aryl" encompasses monocyclic and polycyclic aryl groups. The term "monocyclic aryl" refers to phenyl, and the term "polycyclic aryl" refers to napthyl and anthracenyl, to phenyl rings having at least a second ring fused thereto, and to napthyl rings having a third ring fused thereto. In the case of a polycyclic aryl consisting of a phenyl ring having a second or third ring fused thereto, or a napthyl ring having a third ring fused thereto, the additional rings may be aromatic or non-aromatic carbocyclic or heterocyclic rings, provided that in such cases the point of attachment will be to the carbocyclic aromatic ring. Additionally, a ring carbon atom of the second and third further rings may be replaced with a carbonyl [—C($=$O)group] (e.g., when such rings are non-aromatic). "Substituted aryl" refers to an aryl group substituted by one or more substituents, preferably 1 to 4 substituents (more preferably 1 or 2), at any point of attachment of any ring, selected from alkyl, substituted alkyl, and the substituents recited above for substituted alkyl groups.

Accordingly, examples of aryl groups include:

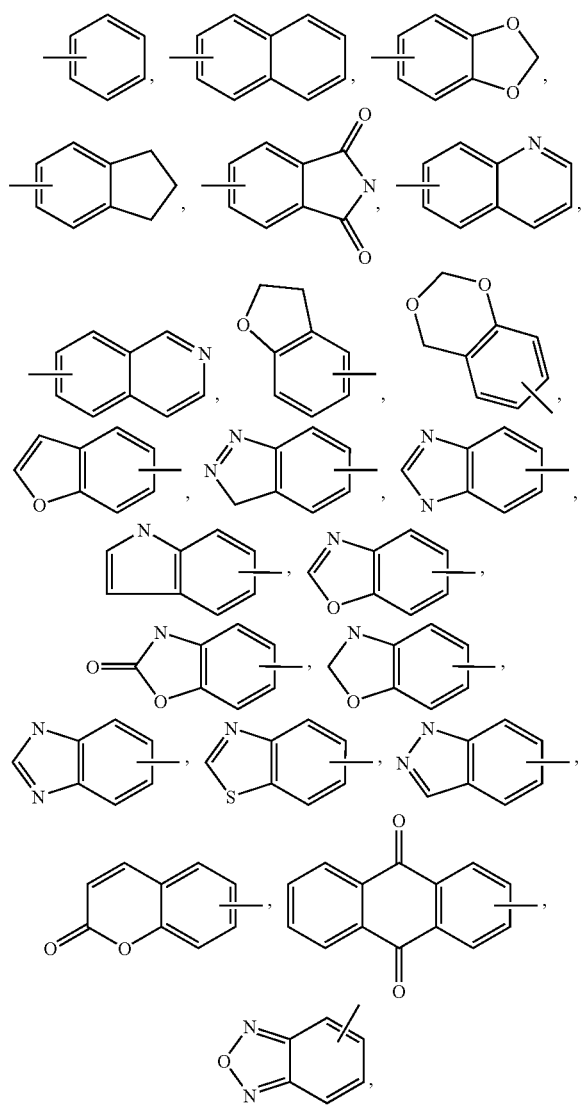

and the like.

The term "arylene" refers to bivalent aryl groups as defined above.

"Carbamoyl" refers to the group —C(=O)—NR$^h$R$^i$, wherein R$^h$ and R$^i$ are selected from hydrogen, alkyl, cycloalkyl, aryl, and heterocyclo.

"Carbamate" refers to the group —O—C(=O)—NR$^h$R$^i$, and "urea" refers to the groups NH—C(=O)—NR$^h$R$^i$ and N(alkyl)-C(=O)—NR$^h$R$^i$, wherein R$^h$ and R$^i$ are selected from the same groups recited for carbamoyl.

"Substituted carbamoyl", "substituted carbamate", and "substituted urea" refer to the groups —C(=O)—NR$^h$R$^i$, —O—C(=O)—NR$^h$R$^i$, and —N(R$^j$)—C(=O)—NR$^h$R$^i$, respectively, wherein R$^h$, R$^i$, and R$^j$ are selected from hydrogen, alkyl, substituted alkyl, cycloalkyl, substituted cycloalkyl, aryl, substituted aryl, heterocyclo, and substituted heterocyclo, provided that at least one of R$^h$, R$^i$, and R$^j$ is substituted alkyl, substituted cycloalkyl, substituted aryl, or substituted heterocyclo.

The terms "heterocycle", "heterocyclic" and "heterocyclo" refer to fully saturated, partially unsaturated, or fully unsaturated, including aromatic (i.e., "heteroaryl") cyclic groups (for example, 3 to 7 membered monocyclic, 7 to 11 membered bicyclic, or 10 to 16 membered tricyclic ring systems) which have at least one heteroatom in at least one carbon atom-containing ring. Thus, the term "heteroaryl" is a subset of heterocyclo groups. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) Additionally, one or more (preferably one) carbon ring atoms of the heterocyclo ring may, as valence allows, be replaced with carbonyl group, i.e., —C(=O)—. The heterocyclic group may be attached to the remainder of the molecule at any heteroatom or carbon atom of the ring or ring system.

Exemplary monocyclic heterocyclic groups include ethylene oxide, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, isoindolyl, benzothiazolyl, benzodioxolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydrobenzodioxinyl, dihydrodioxidobenzothiophenyl, dihydroisoindolyl, dihydroindolyl, dihydroquinolinyl, dihydroquinazolinyl (such as 3,4-dihydro-4-oxo -quinazolinyl), triazinylazepinyl, tetrahydroquinolinyl and the like. Exemplary tricyclic heterocyclic groups include carbazolyl, benzidolyl, phenanthrolinyl, dibenzofuranyl, acridinyl, phenanthridinyl, xanthenyl and the like. The term "heterocyclene" refers to bivalent heterocycle groups as defined above.

"Substituted heterocycle", "substituted heterocyclic", and "substituted heterocyclo" (such as "substituted heteroaryl") refer to heterocycle, heterocyclic or heterocyclo groups substituted with one or more substituents, preferably 1 to 4 substituents, at any available point of attachment, wherein the substituents are selected from those recited above for substituted cycloalkyl groups.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethyl-hydroammonium, N-hydropyridinium), the positively charged nitrogen in amine N-oxides (e.g., N-methylmorpholine-N-oxide, pyridine-N-oxide), and the positively charged nitrogen in an N-amino-ammonium group (e.g., N-aminopyridinium).

The term "heteroaryl" refers to five and six member monocyclic aromatic heterocyclo groups, as well as bicyclic and tricyclic heterocyclic ring systems in which the point of attachment of the ring system to another group is via a five or six member aromatic ring of the ring system. Thus, for example, the term heteroaryl includes groups such as five or six member heteroaryl groups, such as thienyl, pyrrolyl, oxazolyl, pyridyl, pyrazinyl, and the like, wherein fused rings completing bicyclic and tricyclic groups may contain only carbon atoms and may be saturated, partially saturated, or unsaturated. Heteroaryl groups which are bicyclic or tricyclic must include at least one fully aromatic ring but the other fused ring or rings may be aromatic or non-aromatic. The term "substituted heteroaryl" refers to five and six member monocyclic aromatic heterocyclo groups substituted with one or more substituents, preferably 1 to 4 substituents, at any available point of attachment, wherein the substituents are selected from those recited above for substituted cycloalkyl groups.

Exemplary monocyclic heteroaryl groups include pyrrolyl, pyrazolyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, and the like.

Exemplary bicyclic heteroaryl groups include indolyl, benzothiazolyl, benzodioxolyl, benzoxazolyl, benzothienyl, quinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, and the like.

Exemplary tricyclic heteroaryl groups include carbazolyl, benzidolyl, phenanthrolinyl, acridinyl, phenanthridinyl, xanthenyl and the like.

The terms "halogen" or "halo" refer to chlorine, bromine, fluorine or iodine.

The terms "hydroxylamine" and "hydroxylamide" refer to the groups —NH—OH and —C(=O)—NH—OH, respectively.

Unless otherwise indicated, the term "substituted amino" as employed herein alone or as part of another group refers to amino substituted with one or two substituents, which may be the same or different, such as alkyl, aryl, arylalkyl, heterocyclo, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, —C(O)R$^f$, —C(=O)OR$^f$, —C(=O)NR$^f$R$^g$, —S(O)$_2$R$^f$, —S(O)$_2$OR$^f$, or —S(O)$_2$NR$^f$R$^g$, wherein R$^f$ and R$^g$ can be hydrogen, alkyl, substituted alkyl, aryl, substituted aryl or heterocyclo. These substituents may be further substituted with a carboxylic acid and/or any of the substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, aryl, heterocyclo, alkoxy, alkylthio, halo, trifluoromethyl, hydroxy, amino, —C(O)R$^f$, —C(=O)OR$^f$, —C(=O)NR$^f$R$^g$, —S(O)$_2$R$^f$, —S(O)$_2$OR$^f$, or —S(O)$_2$NR$^f$R$^g$, wherein R$^f$ and R$^g$ can be hydrogen, alkyl, substituted alkyl, aryl, substituted aryl or heterocyclo.

The term "heteroatoms" shall include oxygen, sulfur and nitrogen.

The term "haloalkyl" means an alkyl having one or more halo substituents.

The term "haloalkoxy" means an alkoxy group having one or more halo substituents. For example, "haloalkoxy" includes —OCF$_3$.

The term "carbocyclic" means a saturated or unsaturated monocyclic or bicyclic ring in which all atoms of all rings are carbon. Thus, the term includes cycloalkyl and aryl rings. The carbocyclic ring may be substituted, in which case the substituents are selected from those recited above for cycloalkyl and aryl groups.

When the term "unsaturated" is used herein to refer to a ring or group, the ring or group may be fully unsaturated or partially unsaturated.

When it is stated that a group may be "optionally substituted", this is intended to include unsubstituted groups and substituted groups wherein the substituents are selected from those recited above for the particularly named group. Thus, when reference is made to an optionally substituted aryl, it is intended to refer to unsubstituted aryl groups, such as phenyl or naphthyl, and such groups having one or more (preferably 1 to 4, and more preferably 1 or 2) substituents selected from alkyl, substituted alkyl, and those substituents recited for substituted alkyl groups. When the term "optionally substituted" precedes a Markush group, the term "optionally substituted" is intended to modify each one of the species recited in the Markush group. Thus, for example, the phrase "optionally substituted aryl, cycloalkyl, or heterocycle" includes aryl, substituted aryl, cycloalkyl, substituted cycloalkyl, heterocycle, and substituted heterocycle.

Among the compounds of the invention, in the case of a compound which has a sulfide, the sulfur atom may be converted into oxido at an appropriate oxidation state, and all of these oxido derivatives are included herein.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

"Solvate" refers to a molecular or ionic complex of molecules or ions of solvent with molecules or ions of solute. It should further be understood that solvates (e.g., hydrates) of the compounds of Formula (I) are also within the scope of the present invention. Methods of solvation are generally known in the art.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1991).

Unless otherwise indicated, any heteroatom with unsatisfied valences is assumed to have hydrogen atoms sufficient to satisfy the valences.

Carboxylate anion refers to a negatively charged group —COO$^-$.

The compounds of the present invention may form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of the present invention may form salts with alkali metals such as sodium, potassium, and lithium; with alkaline earth metals such as calcium and magnesium; and with organic bases such as dicyclohexylamine, tributylamine, pyridine, and amino acids such as arginine, lysine, and the like. Such salts can be formed as known to those skilled in the art.

The compounds of the present invention may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid, and various others (e.g., nitrates, phosphates, borates, tartrates, citrates, succinates, benzoates, ascorbates, salicylates, and the like). Such salts can be formed as known to those skilled in the art. Salt forms of the compounds may be advantageous for improving the compound dissolution rate and oral bioavailability.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures; it also embraces the racemic forms and the isolated optical isomers having the specified activity. The racemic forms can be resolved by physical methods, such as, for example, fractional crystallization, separation, or crystallization of diastereomeric derivatives or separation by chiral column chromatography. The individual optical isomers can be obtained from the racemates from the conventional methods, such as, for example, salt formation with an optically active acid followed by crystallization.

Particular Compounds

One embodiment of the present invention relates to a compound of Formula (I)

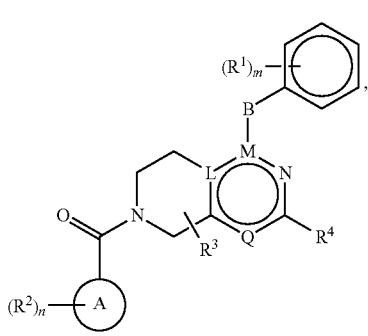

(I)

or an enantiomer, diastereomer or a pharmaceutically-acceptable salt thereof wherein:

L and M are as defined above;

ring A is an aryl or heteroaryl selected from the group consisting of phenyl, indole, azaindole, quinoline, thiazole, thiophene, benzofuran and benzothiophene;

$R^1$, $R^2$ and $R^3$ are as defined above;

$R^4$ is selected from the group consisting of hydrogen; hydroxyl; halo; haloalkyl wherein the haloalkyls have 1-3 carbons and 1-5 halogens (for example, $CF_3$, $CH_2CF_3$, and $CF_2CH_3$); $CO_2R^{10}$, $CONR^{10}R^{20}$ or $NR^{10}R^{10}R^{20}$ wherein each of $R^{10}$ and $R^{20}$ are independently selected from the group consisting of H, C1-C6 straight or branched chain alkyl, C1-C4 straight or branched chain alkyl amino, C1-C4 straight or branched chain dialkyl amino, C 1-C4 straight or branched chain alkyl with an OH group, C4-C10 heterocyclo with 1-3 members selected from the group consisting of N, S and O, provided there is no O—O or S—S portion, optionally substituted amino, and alkyl amino;

m is as defined above with particular examples of fused rings formed by 2 of $R^1$ being a ring selected from the group consisting of an optionally fused and optionally substituted cycloalkyl, benzyl, benzoyl, aryl, heterocyclo and heteroaryl;

n is as defined above;

B is as defined above, particularly wherein q is 0.

In another embodiment, a particular value for $R^4$ is selected from the group consisting of hydrogen; hydroxyl, halo, haloalkyl wherein the haloalkyls have 1-3 carbons and 1-5 halogens, $CO_2R^{11}$, $CONR^{11}R^{12}$ and $NR^{11}R^{12}$ wherein each of $R^{11}$ and $R^{12}$ are independently selected from the group consisting of H, C1-C6 straight or branched chain alkyl, C1-C4 straight or branched chain alkyl amino, C1-C4 straight or branched chain dialkyl amino, C 1-C4 straight or branched chain alkyl with an OH group; and C4-C10 heterocyclo with 1-3 members selected from the group consisting of N, S and O, provided there are no O—O or S—S bonds in $R^4$ and the heterocyclo group can be optionally substituted with a member selected from the group consisting of C1-C4 alkyl, optionally substituted amino, and alkyl amino.

In another particular embodiment for Formula (I),

Q is a bond when L is —N— and M is —C═;

ring A is selected from phenyl, indole and pyrrolo[2,3-b]pyridine;

q is 0;

m is 1 or 2;

n is 1 or 3;

$R^1$ is halo, halo-$C_{1-3}$ alkyl (for example, those having 1-3 carbons and 1-5 halogens such as $CF_3$, $CH_2CF_3$, and $CF_2CH_3$) or optionally substituted $C_{1-3}$ alkyl;

$R^2$ is selected from the group consisting of halo, halo-$C_{1-3}$ alkyl (for example, those having 1-3 carbons and 1-5 halogens such as $CF_3$, $CH_2CF_3$, and $CF_2CH_3$), optionally substituted $C_{1-3}$ alkyl, $C_{1-3}$ alkoxy and —[C(O)]$_2$NR$^7$R$^8$ wherein —[C(O)]$_2$NR$^7$R$^8$ has the meaning defined above; and $R^3$ and $R^4$ are each hydrogen.

One particular group of compounds of the present invention includes those selected from the group consisting of:

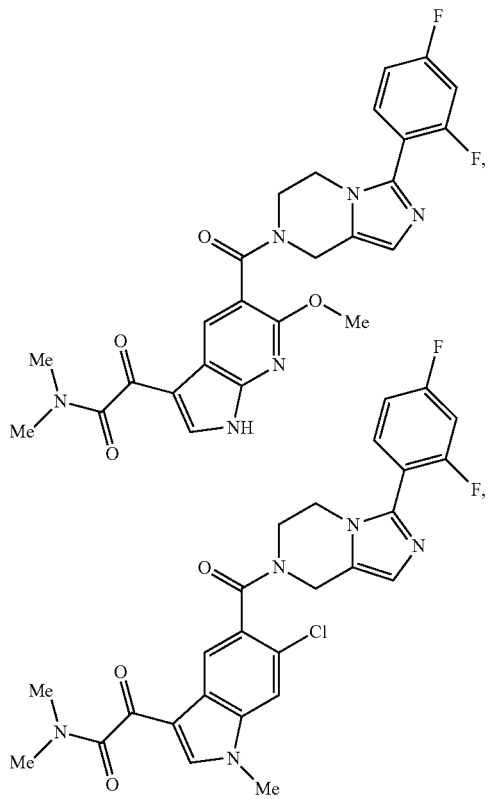

13
-continued

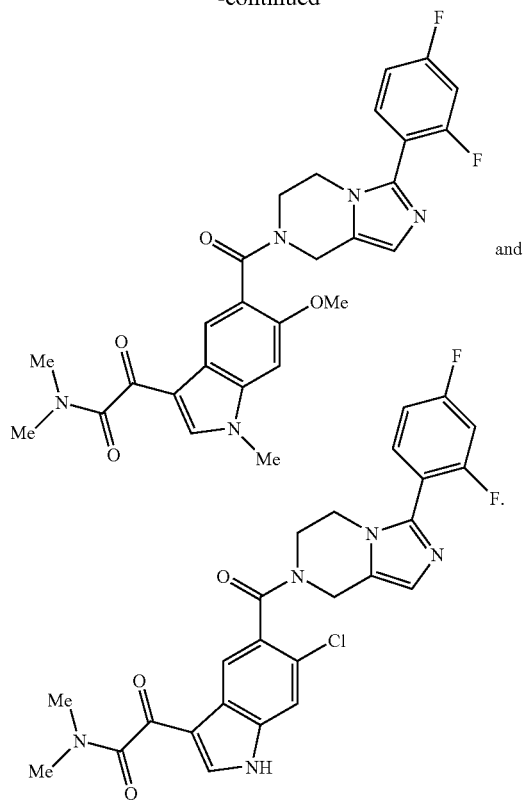

In yet another particular embodiment of Formula (I),
Q is a bond when L is —C═ and M is —N—;
q is O;
$R^1$ is halo or $C_{1-3}$ alkyl;
$R^2$ is selected from the group consisting of halo, halo-$C_{1-3}$ alkyl (for example, those having 1-3 carbons and 1-5 halogens such as $CF_3$, $CH_2CF_3$, and $CF_2CH_3$), optionally substituted $C_{1-3}$ alkyl, optionally substituted $C_{1-3}$ alkoxy, and —[C(O)]$_2$NR$^7$R$^8$ wherein —[C(O)]$_2$NR$^7$R$^8$ has the meaning defined above;
$R^3$ is hydrogen;
$R^4$ is hydrogen or —C(O)NR$^9$R$^{10}$ wherein —C(O)NR$^9$R$^{10}$ has the same meaning as defined above;
ring A is selected from the group consisting of phenyl, indole, indazole, benzo-imidazole, pyrrolo[2,3-b]pyridine and 2,3,4,9-tetrahydro-1H-pyrido[3,4-b]indole.

Still another particular group of compounds are those selected from the group consisting of:

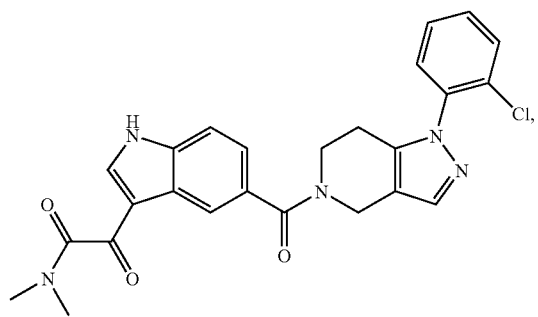

14
-continued

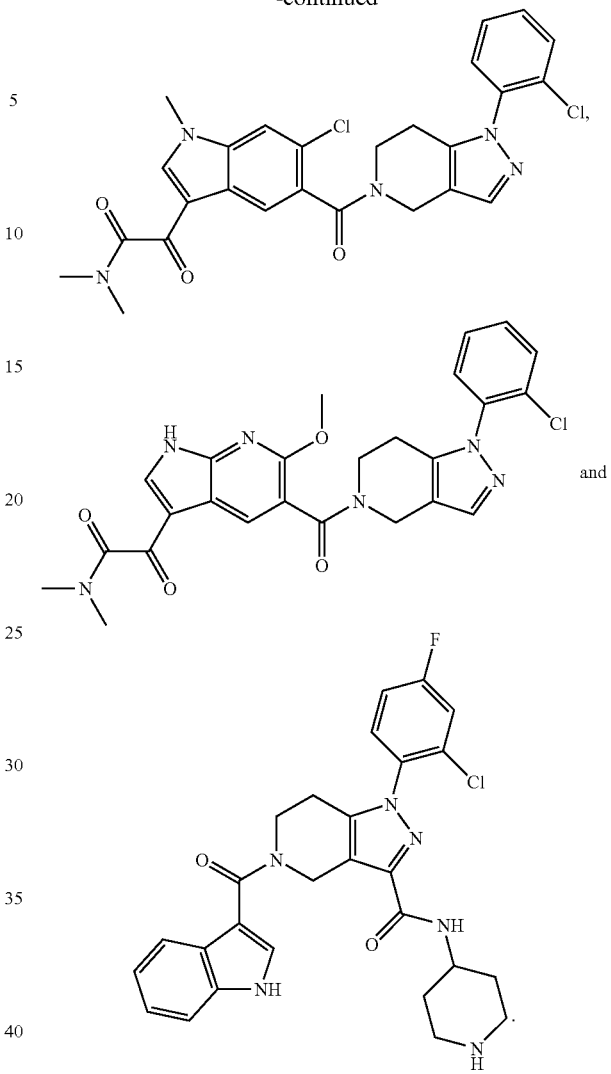

In another more particular embodiment of the invention as shown in Formula (I):
Q is —N═ when L and M are both —C═;
ring A is an indole;
m is 2;
n is 3;
q is 0;
$R^1$ is halo;
$R^2$ is halo, $C_{1-3}$ alkyl or —[C(O)]$_2$NR$^7$R$^8$ wherein each of $R^7$ and $R^8$ is independently a $C_{1-3}$ alkyl; and
$R^3$ and $R^4$ are each hydrogen.

Other embodiments of this invention include pharmaceutical compositions comprising at least one compound of Formula (I) and a pharmaceutically acceptable carrier or diluent.

Utility

The compounds of the invention are selective inhibitors of p38 kinase, and in particular, isoforms p38α and p38β. Accordingly, compounds of Formula (I) have utility in treating conditions associated with p38 kinase activity. Such conditions include diseases or disorders in which cytokine levels are modulated as a consequence of intracellular signaling via p38, and in particular diseases that are associated with an overproduction of cytokines IL-1, IL-4, IL-8 and TNF-α. As used herein, the terms "treating" or "treatment" encompass responsive and/or prophylaxis measures addressed to the disease state and/or its symptoms, e.g. measures designed to inhibit or delay the onset of the disease or disorder, achieve a full or partial reduction of the symptoms or disease state, and/or alleviate, lessen, or cure the disease and/or its symptoms. When reference is made herein to inhibition of "p-38α/β kinase", this means that either or both p38α and p38β kinase are inhibited.

In view of their activity as inhibitors of p-38α/β kinase, compounds of Formula (I) are useful in treating inflammatory diseases, autoimmune diseases, destructive bone disorders, proliferative disorders, angiogenic disorders, infectious diseases, neurodegenerative diseases, viral diseases, and ischemia reperfusion conditions.

More particularly, the inventive compounds may be used to treat inflammatory diseases including, but not limited to, arthritis (e.g., rheumatoid arthritis, lyme disease arthritis, osteoarthritis, traumatic arthritis, rubella arthritis, psoriatic arthritis, gouty arthritis, and other arthritic conditions), glomerulonephritis, pancreatitis (acute or chronic), diabetes, diabetic retinopathy, macular degeneration, conjunctivitis, aplastic anemia, thrombocytopenia, gastritis, chronic thyroiditis, chronic active hepatitis, multiple sclerosis, inflammatory bowel disease, ulcerative colitis, Crohn's disease, cachexia (including cachexia secondary to infection, cancer, or heart disease), periodontal disease, Alzheimer's disease, Parkinson's disease, keloid formation, pulmonary sarcoidosis, myasthenia gravis, inflammatory reaction induced by endotoxin, Reiter's syndrome, gout, acute synovitis, diseases characterized by massive neutrophil infiltration, ankylosing spondylitis, influenza, cerebral malaria, silicosis, bone resorption disease, fever, myalgias due to infection, osteoporosis, multiple myeloma-related bone disorder, neurodegenerative disease caused by traumatic injury, and traumatic brain injury.

The inventive compounds may also be used to treat acute or chronic graft vs. host reactions (e.g., pancreatic islet allograft), acute or chronic transplant rejection (e.g., kidney, liver, heart, lung, pancreas, bone marrow, cornea, small bowel, skin allografts, skin homografts, heterografts, and/or cells derived from such organs), and skin conditions including, but not limited to, scar tissue formation, eczema, atopic dermatitis, contact dermatitis, urticaria, scleroderma, scleraclerma, and psoriasis. The inventive compounds also may be used to treat allergies and respiratory conditions, including asthma, acute respiratory distress syndrome, hay fever, allergic rhinitis, and any chronic pulmonary inflammatory disease, such as chronic obstructive pulmonary disease. The compounds further may be used to treat steroid resistance in asthma and allergies.

Additionally, the inventive compounds may be used to treat inflammation associated with autoimmune diseases including, but not limited to, systemic lupus erythematosis, Addison's disease, autoimmune polyglandular disease (also known as autoimmune polyglandular syndrome), and Graves' disease. The inventive compounds may be used to treat infectious diseases such as sepsis, septic shock, Shigellosis, and *Heliobacter Pylori*.

The instant compounds may be used to treat viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatitis B, and hepatitis C), HIV infection and CMV retinitis, AIDS<ARC or malignancy, and herpes.

The inventive compounds also may be used to treat angiogenic disorders including solid tumors, ocular neovasculization and infantile haemangiomas. In addition, p38 inhibitors of this invention inhibit the expression of inducible pro-inflammatory proteins such as prostaglandin endoperoxide synthase-2 (PGHS-2), also referred to as cyclooxygenase-2 (COX-2). Accordingly, additional conditions that may be treated with the inventive compounds include edema, analgesia and pain, such as neuromuscular pain, headache, pain caused by cancer or surgery, dental pain and arthritis pain. In view of their COX-2 inhibitory activity, the inventive compounds also may be used to treat cancer, including, without limitation, epithelial cancer and adenocarcinoma.

Additionally, the compounds of this invention are useful to treat ischemia, including ischemia resulting from vascular occlusion, cerebral infarction, stroke, and related cerebral vascular diseases (including cerebrovascular accident and transient ischemic attack). Accordingly, the compounds may be used to treat myocardial infarction, coronary artery disease, non-Q wave MI, congestive heart failure, ventricular hypertrophy, cardiac arrhythmias, unstable angina, chronic stable angina, Prinzmetal's angina, high blood pressure, intermittent claudication, silent ischemia, cardiac hypertrophy, and peripheral occlusive arterial disease (e.g., peripheral arterial disease, critical leg ischemia, prevention of amputation, and prevention of cardiovascular morbidity such as MI, stroke or death).

Additionally, in view of their activity in treating ischemia, the compounds of the invention may be useful to treat symptoms or consequences occurring from thrombosis, atherosclerosis, peripheral arterial disease, and thrombotic or thromboembolic symptoms or consequences associated with and/or caused by one or more of the following: thromboembolic stroke (including that resulting from atrial fibrillation or from ventricular or aortic mural thrombus), venous thrombosis (including deep vein thrombosis), arterial thrombosis, cerebral thrombosis, pulmonary embolism, cerebral embolism, thrombophilia (e.g., Factor V Leiden, and homocystinenimia), coagulation syndromes and coagulopathies (e.g., disseminated intravascular coagulation), restenosis (e.g., following arterial injury induced endogenously or exogenously), atrial fibrillation, and ventricular enlargement (including dilated cardiac myopathy and heart failure). The compounds of the invention also may be used to treat symptoms or consequences of atherosclerotic diseases and disorders, such as atherosclerotic vascular disease, atherosclerotic plaque rupture, atherosclerotic plaque formation, transplant atherosclerosis, and vascular remodeling atherosclerosis. The compounds of the invention further may be used to treat symptoms or consequences of thrombotic or thromboembolic conditions associated with cancer, surgery, inflammation, systematic infection, artificial surfaces (such as stents, blood oxygenators, shunts, vascular access ports, vascular grafts, artificial valves, etc.), interventional cardiology such as percutaneous transluminal coronary angioplasty (PTCA), immobility, medication (such as oral contraceptives, hormone replacement therapy, and heparin), pregnancy and fetal loss, and diabetic complications including retinopathy, nephropathy, and neuropathy.

The compounds of the present invention may be used for the preservation of tissue, for example, the preservation of tissue as relates to organ transplantation and surgical manipulation. The compounds may be used to treat diseases or disorders in other tissues or muscles that are associated with ischemic conditions and/or to enhance the strength or stability of tissue and muscles. For example, the compounds may be used to treat muscle cell damage and necrosis and/or to enhance athletes' performance.

Additional diseases and disorders that may be treated with the inventive compounds include irritable bowel syndrome, leukemia, CNS disorders associated with cerebral ischemia, such as cerebral infarction, cerebral edema and the like, and diseases associated with proliferation of smooth muscle cells, mesangial cells, and fibroblasts. Such diseases include renal fibrosis, hepatic fibrosis, prostate hypertrophy, and pulmonary fibrosis.

The inventive compounds also may be used to treat veterinary viral infections, such as lentivirus infections, including, but not limited to, equine infectious anemia virus; or retro virus infections, including feline immunodeficiency virus, bovine immunodeficiency virus, and canine immunodeficiency virus.

When the terms "p38 associated condition" or "p38 associated disease or disorder" are used herein, each is intended to encompass all of the conditions identified above as if repeated at length, as well as any other condition that is modulated by p38 kinase activity.

The present invention thus provides methods for treating such conditions, comprising administering to a subject in need thereof an effective amount of at least one compound of Formula (I), or a pharmaceutically-acceptable salt thereof. The methods of treating p38 kinase-associated conditions may comprise administering compounds of Formula (I) alone or in combination with each other and/or other suitable therapeutic agents such as anti-inflammatory drugs, antibiotics, anti-viral agents, anti-oxidants, cholesterol/lipid lowering agents, anti-tumor agents including antiproliferative agents, and agents used to treat ischemia.

Examples of suitable other anti-inflammatory agents with which the inventive compounds may be used include aspirin, cromolyn, nedocromil, theophylline, zileuton, zafirlukast, monteleukast, pranleukast, indomethacin, and lipoxygenase inhibitors; non-steroidal anti-inflammatory drugs (NSAIDs) (such as ibuprofen and naproxin); TNF-α inhibitors (such as tenidap and rapamycin or derivatives thereof), or TNF-α antagonists (e.g., infliximab, enbrel, D2E7, OR1384), cytokine modulators (e.g., TNF-alpha converting enzyme [TACE] inhibitors, Interleukin-1 converting enzyme (ICE) inhibitors, Interleukin-1 receptor antagonists), prednisone, dexamethasone, Enbrel®, cyclooxygenase inhibitors (i.e., COX-1 and/or COX-2 inhibitors such as Naproxen®, Celebrex®, or Vioxx®), CTLA4-Ig agonists/antagonists (LEA29Y), CD40 ligand antagonists, IMPDH inhibitors (such as mycophenolate [CellCept®] and VX-497), integrin antagonists, alpha-4 beta-7 integrin antagonists, cell adhesion inhibitors, interferon gamma antagonists, ICAM-1, prostaglandin synthesis inhibitors, budesonide, clofazimine, CNI-1493, CD4 antagonists (e.g., priliximab), other p38 mitogen-activated protein kinase inhibitors, protein tyrosine kinase (PTK) inhibitors, IKK inhibitors, therapies for the treatment of irritable bowel syndrome (e.g., Zelmac®, Zelnorm®, and Maxi-K openers such as those disclosed in U.S. Pat. No. 6,184,231 B1), or other NF-κB inhibitors (such calphostin, CSAIDs, and quinoxalines as disclosed in U.S. Pat. No. 4,200,750); corticosteroids (such as beclomethasone, triamcinolone, budesonide, fluticasone, flunisolide, dexamethasone, prednisone, and dexamethasone); disassociated steroids; chemokine receptor modulators (including CCR1, CCR2, CCR3, CCR4, and CXCR2 receptor antagonists); secretory and cytosolic phospholipase A2 inhibitors, VLA4 antagonists, glucocorticoids, salicylates, nitric oxide, and other immunosuppressants; and nuclear translocation inhibitors, such as deoxyspergualin (DSG).

To treat pain, the inventive compounds may be used in combination with aspirin, NSAIDs, or with 5-HT 1 receptor agonists such as buspirone, sumitriptan, eletriptan or rizatriptan.

Examples of suitable antibiotics with which the inventive compounds may be used include β-lactams (e.g., penicillins, cephalosporins and carbopenams); β-lactam and lactamase inhibitors (e.g., augmentin); aminoglycosides (e.g., tobramycin and streptomycin); macrolides (e.g., erythromycin and azithromycin); quinolones (e.g., cipro and tequin); peptides and deptopeptides (e.g., vancomycin, synercid and daptomycin); metabolite-based antibiotics (e.g., sulfonamides and trimetoprim); polyring systems (e.g., tetracyclins and rifampins); protein synthesis inhibitors (e.g. zyvox, chlorophenicol, clindamycin, etc.); and nitro-class antibiotics (e.g., nitrofurans and nitroimidazoles).

Examples of suitable antiviral agents for use with the inventive compounds include nucleoside-based inhibitors, protease-based inhibitors, and viral-assembly inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-oxidants for use in combination with the compounds of the present invention include lipid peroxidation inhibitors such as probucol, BO-653, Vitamin A, Vitamin E, AGI-1067, and α-lipoic acid.

A further use of the compounds of this invention is in combination with steroidal or non-steroidal progesterone receptor agonists ("PRA"), such as levonorgestrel, medroxyprogesterone acetate (MPA).

The inventive compounds also may be used in combination with anti-diabetic agents, such as biguanides (e.g., metformin), glucosidase inhibitors (e.g., acarbose), insulins (including insulin secretagogues or insulin sensitizers), meglitinides (e.g., repaglinide), sulfonylureas (e.g., glimepiride, glyburide and glipizide), biguanide/glyburide combinations (e.g., glucovance), thiazolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Pat. No. 6,548,529 and assigned to the present assignee, glucagon-like peptide-1 (GLP-1), glucagon phosphorylase, and dipeptidyl peptidase IV (DP4) inhibitors.

In addition, the compounds may be used with agents that increase the levels of cAMP or cGMP in cells for a therapeutic benefit. For example, the compounds of the invention may have advantageous effects when used in combination with phosphodiesterase inhibitors, including PDE1 inhibitors (such as those described in *Journal of Medicinal Chemistry*, Vol. 40, pp. 2196-2210 [1997]), PDE2 inhibitors, PDE3 inhibitors (such as revizinone, pimobendan, or olprinone), PDE4 inhibitors (such as rolipram, cilomilast, or piclamilast), PDE7 inhibitors, or other PDE inhibitors such as dipyridamole, cilostazol, sildenafil, denbutyline, theophylline (1,2-dimethylxanthine), ARIFLO™ (i.e., cis-4-cyano-4-[3-(cyclopentyloxy)-4-methoxyphenyl]cyclohexane-1-carboxylic acid), arofyline, roflumilast, C-11294A, CDC-801, BAY-19-8004, cipamfylline, SCH351591, YM-976, PD-189659, mesiopram, pumafentrine, CDC-998, IC-485, and KW-4490.

The inventive compounds may also be useful in combination with anticancer strategies and chemotherapies such as taxol and/or cisplatin. The compounds may be used in conjunction with anti-tumor agents such as paclitaxel, adriamycin, epothilones, cisplatin, and carboplatin.

In view of their usefulness in treating ischemia, the inventive compounds may be used in combination with agents for inhibiting F1F0-ATPase, including efrapeptin, oligomycin, autovertin B, azide, and compounds described in U.S. Publication No. 2004-0039033A1, published Feb. 26, 2004, and assigned to the present assignee; alpha- or beta-adrenergic blockers (such as propranolol, nadolol, carvedilol, and prazosin), or -β-adrenergic agonists (such as albuterol, terbutaline, formoterol, salmeterol, bitolterol, pirbuterol, and fenoterol); antianginal agents such as nitrates, for example, sodium nitrates, nitroglycerin, isosorbide mononitrate, isosorbide dinitrate, and nitrovasodilator; antiarrhythmic agents including Class I agents (such as propafenone); Class II agents (propranolol); Class III agents (such as sotalol, dofetilide, amiodarone, azimilide and ibutilide); Class IV agents (such as ditiazem and verapamil); $K^+$ channel modulators such as IAch inhibitors and inhibitors of the Kv1 subfamily of $K^+$ channel openers such as IKur inhibitors (e.g., compounds disclosed in U.S. Pat. No. 6,706,720, assigned to the present assignee); and gap-junction modulators such as connections; anticoagulant or antithrombotic agents including aspirin, warfarin, ximelagatran, low molecular weight heparins (such as lovenox, enoxaparin, and dalteparin), anti-platelet agents such as GPIIb/GPIIIa blockers (e.g., abciximab, eptifibatide and tirofiban), thromboxane receptor antagonists (e.g., ifetroban), P2Y1 and P2Y12 antagonists (e.g., clopidogrel, ticlopidine, CS-747, and aspirin/clopidogrel combinations), and Factor Xa inhibitors (e.g., fondaprinux); and diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene and amiloride.

Additionally, the inventive compounds may be used in combination with lipid profile modulators and anti-atheroaclerotic agents including HMG-CoA reductase inhibitors (e.g., pravastatin, simvastatin, atorvastatin, fluvastatin, cerivastatin, AZ4522, itavastatin [Nissan/Kowa]), ZD-4522 (a.k.a. rosuvastatin, itavastatin or visastatin), pravachol, squalene synthetase inhibitors, fibrates, bile acid sequestrants (such as questran), niacin and niacin/statin combinations, lipoxygenase inhibitors, ileal Na+/bile acid cotransporter inhibitors, ACAT1 inhibitors, ACAT2 inhibitors, dual ACAT½ inhibitors, microsomal triglyceride transport protein inhibitors (such as disclosed in U.S. Pat. Nos. 5,739,135, 5,712,279 and 5,760,246), cholesterol absorption inhibitors (such as Zetia®), cholesterol ester transfer protein inhibitors (e.g., CP-529414), PPAR-delta agonists, PPAR-alpha agonists, dual PPAR-alpha/delta agonists, LXR-alpha agonists, LXR-beta agonists, LXR dual alpha/beta agonists, and SCAP modulators.

The combination of the inventive compounds with other therapeutic agents may prove to have additive and synergistic effects. The combination may be advantageous to increase the efficacy of the administration or decrease the dosage to reduce possible side-effects.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above. Pharmaceutical compositions may be formulated by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulations.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; buccally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

Compounds of Formula (I), including the compounds described in the examples herein, have been tested in one or more of the assays described below and have shown activity as inhibitors of p38α/β enzymes and TNF-α.

In general, preferred compounds of the present invention, such as particular compounds disclosed in the following examples, have been identified to inhibit the activity of one or more of p38α/β enzymes. Potencies can be calculated and expressed as either inhibition constants ($K_i$ values) or as $IC_{50}$ (inhibitory concentration 50%) values, and refer to activity measured employing the in vitro assay systems described herein. Exemplary values for compounds that inhibit the activity of p38α/β enzymes include concentration equivalent to, or more potent than, 10 μM, preferably 1 μM, and more preferably 0.1 μM, thereby demonstrating particular compounds of the present invention as effective inhibitors of p38 α/β enzymes.

Biological Assays

Generation of p38 Kinases cDNAs of human p38α, β, and γ isozymes were cloned by PCR. These cDNAs were subcloned in the pGEX expression vector (Pharmacia). GST-p38 fusion protein was expressed in *E. Coli* and purified from bacterial pellets by affinity chromatography using glutathione agarose. p38 fusion protein was activated by incubating with constitutively active MKK6. Active p38 was separated from MKK6 by affinity chromatography. Constitutively active MKK6 was generated according to Raingeaud et al. [*Mol. Cell. Biol.*, 1247-1255 (1996)].

TNF-α Production by LPS-stimulated PBMCs

Heparinized human whole blood was obtained from healthy volunteers. Peripheral blood mononuclear cells (PBMCs) were purified from human whole blood by Ficoll-Hypaque density gradient centrifugation and resuspended at a concentration of $5 \times 10^6$/ml in assay medium (RPMI medium containing 10% fetal bovine serum). 50 μl of cell suspension was incubated with 50 μl of test compound (4× concentration in assay medium containing 0.2% DMSO) in 96-well tissue culture plates for 5 minutes at RT. 100 μl of LPS (200 ng/ml stock) was then added to the cell suspension and the plate was incubated for 6 hours at 37° C. Following incubation, the culture medium was collected and stored at −20° C. TNF-α concentration in the medium was quantified using a standard ELISA kit (Pharmingen-San Diego, Calif.). Concentrations of TNF-α and $IC_{50}$ values for test compounds (concentration of compound that inhibited LPS-stimulated TNF-α production by 50%) were calculated by linear regression analysis.

p38 Assays (1) The assays were performed in V-bottomed 96-well plates. The final assay volume was 60 μl prepared from three 20 μl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 was pre-incubated with test compounds for 10 min. prior to initiation of reaction with substrates. The reaction was incubated at 25° C. for 45 min. and terminated by adding 5 μl of 0.5 M EDTA to each sample. The reaction mixture was aspirated onto a pre-wet filtermat using a Skatron Micro96 Cell Harvester (Skatron, Inc.), then washed with PBS. The filtermat was then dried in a microwave oven for 1 min., treated with MeltilLex A scintillation wax (Wallac), and counted on a Microbeta scintillation counter Model 1450 (Wallac). Inhibition data were analyzed by nonlinear least-squares regression using Prizm (GraphPadSoftware). The final concentration of reagents in the assays are ATP, 1 μM; [γ-$^{33}$P]ATP, 3 nM; MBP (Sigma, #M1891), 2 μg/well; p38, 10 nM; and DMSO, 0.3%.

(2) In an alternate method, the assays were performed in U-bottom 384-well plates. The final assay volume was 30 μl prepared from 15 μl additions of enzyme and substrates (fluoresceinated peptide FL-IPTSPITTTYFFFKKK—OH and ATP) and test compounds in assay buffer (100 mM HEPES pH 7.2, 10 mM $MgCl_2$, 0.015% Brij35 and 4 mM DTT). The reaction was initiated by the combination of bacterially expressed, activated p38 with substrates and test compounds. The reaction was incubated at room temperature for 60 min. and terminated by adding 30 μl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays are ATP, 20 μM; FL-IPTISPITTTYFFFKKK—OH, 1.5 uM; p38, 6 nM; and DMSO, 0.6%.

Abbreviations

For ease of reference, the following abbreviations are employed herein, including the methods of preparation and Examples that follow:
° C.=degrees Celsius
μL=microliter
anhyd.=anhydrous
aq.=aqueous
Boc=tert-butyloxycarbonyl CBZ=carbobenzyloxy or carbobenzoxy or benzyloxycarbonyl
$CO_2$=carbon dioxide
d=doublet
DCE=1,2-dichloroethane
DCM=dichloromethane
dd=doublet of doublet
DEAD=diethyl azodicarboxylate
DIPEA=diisopropylethylamine
DMF=dimethyl formamide
DMSO=dimethyl sulfoxide
EDC or EDCI=1-(3-Dimethylaminopropyl)-3-ethylcarbodiimide hydrochloride
EtOAc=ethyl acetate
EtOH=ethanol
g=gram(s)
h=hour(s)
HATU=O-(7-Azabenzotriazol-1-yl-N,N,N'N'-tetramethyluronium hexafluorophosphate
HCl=hydrogen chloride
HOBt=1-hydroxybenzotriazole hydrate
HPLC=high performance liquid chromatography
$K_2CO_3$=potassium carbonate
KOH=potassium hydroxide
KOtBu=potassium t-butoxide
L=liter
LCMS=high performance liquid chromatography/mass spectrometry
M=Molar
m=multiplet
m-CPBA=m-chloroperbenzoic acid
MeOH=methanol
mg=milligram(s)
MHz=megahertz
min=minute(s)
mL or ml=milliliter
mmol=millimole(s)
mol=moles
MS=mass spectrometry
N=Normal
$Na_2S_2O_3$=sodium thiosulfate
NaH=sodium hydride
NaOEt=sodium ethoxide
NaOH=sodium hydroxide
NMP=N-methylpyrrolidinone
NMR=nuclear magnetic resonance
Pd=palladium
Pd/C=palladium on carbon
PmB=para-methoxybenzyl
$POCl_3$=phosphorous oxychloride
p-TsOH=para-toluenesulphonic acid
Ret. time or $t_R$=retention time (minutes)
rt=room temperature
s=singlet
sat or sat'd=saturated
sec=second (s)
TFA=trifluoroacetic acid
THF=tetrahydrofuran
TMS=trimethylsilyl Methods of Preparation The compounds of the present invention may be synthesized using conventional techniques known in the art. Advantageously, these compounds are conveniently synthesized from readily available starting materials. Following are general synthetic schemes for manufacturing compounds of the present invention. These schemes are illustrative and are not meant to limit the possible techniques one skilled in the art may use to manufacture compounds disclosed herein. Different methods will be evident to those skilled in the art. Additionally, the various steps in the synthesis may be performed in an alternate sequence or order to give the desired compound(s). All documents cited are incorporated herein by reference in their entirety.

Compounds of the present invention can be made by many methods, which will be known to one skilled in the art of organic chemistry. In general, the time taken to complete a reaction procedure will be judged by the person performing the procedure, preferably with the aid of information obtained by monitoring the reaction by methods such as HPLC or TLC. A reaction does not have to go to completion to be useful to this invention. The preparation of heterocycles useful to this invention are described in the series of books: "Comprehensive Heterocyclic Chemistry. The Structure, Reactions, Synthesis and Uses, of Heterocyclic Compounds" Katritzky, A. R., Rees, C. W. Ed's Pergamon Press New York, First edition 1984, and "Comprehensive Heterocyclic Chemistry II. A Review of the Literature 1982-1995. The Structure, Reactions, Synthesis and Uses, of Heterocyclic Compounds" Katritzky, A. R., Rees, C. W. and Scriven, E., F. Ed's Pergamon Press New York, 1996.

Acids or acid chlorides, used for the preparation of compounds useful to this invention may be commercially available or readily prepared by many methods known to one skilled in the art of organic chemistry, and are described in "Comprehensive Organic Transformations. A Guide to Functional Group Preparation." pp. 385-439. Richard C. Larock 1989 VCH Publishers, Inc. General methods for the synthesis of imidazo[1,5a]pyrazines, useful for this invention are outlined in the following schemes.

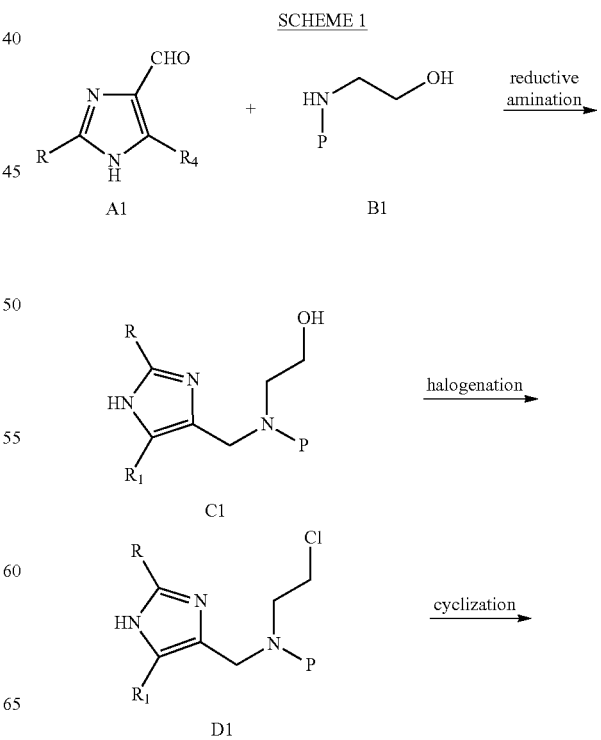

SCHEME 1

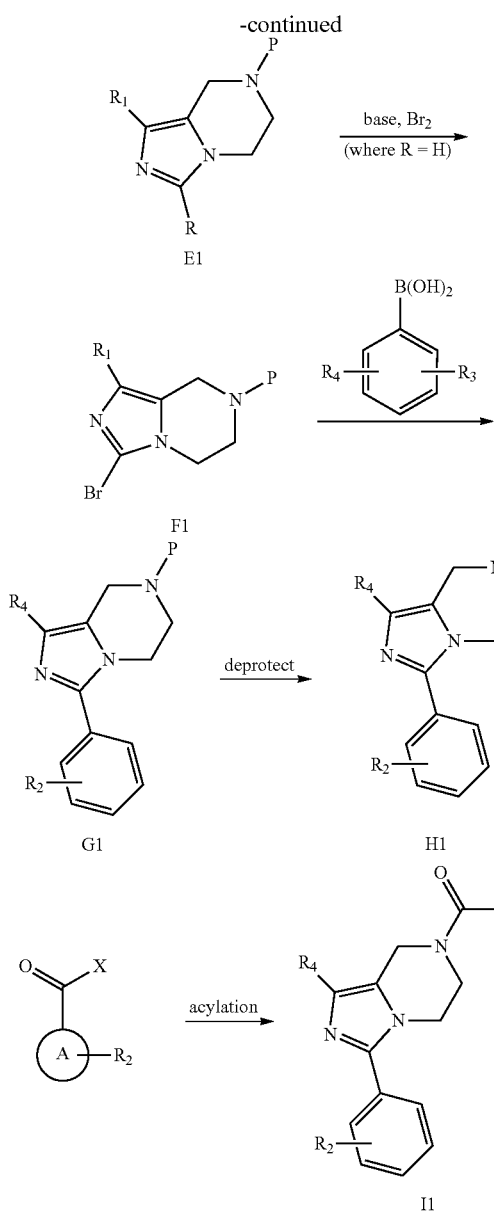

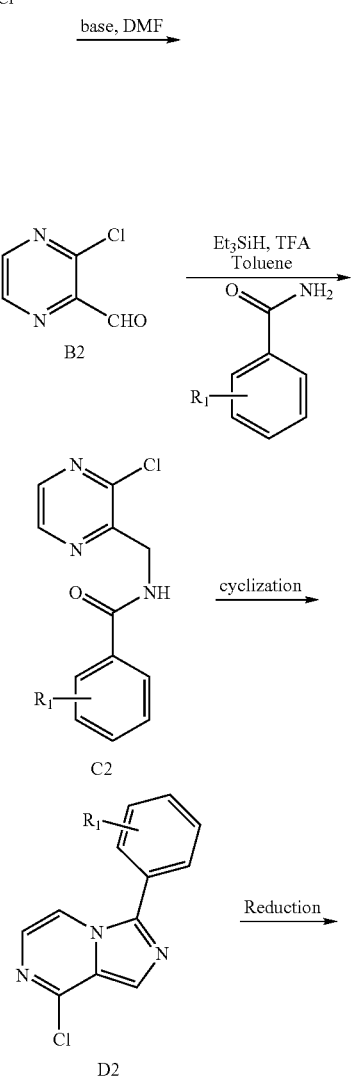

(2004), 1 211-229] of (F1) with an aryl boronic acid or ester in the presence of a suitable catalyst such as tetrakis(triphenylphosphine) palladium affords compounds of type (G1). After cross coupling has been performed, the product may be deprotected to give the amine intermediate (H1) The choice of protecting group and its method of removal will be readily apparent to one skilled in the art of organic chemistry. Such considerations and methods are, for example, described by Theodora W. Greene and Peter G. M. Wuts in *Protective Groups in Organic Synthesis*, 3rd Ed. (1999), (John Wiley and Sons, Inc., New York, N.Y. For example, if the protecting group is acetyl, the product may be deprotected by treatment with aqueous potassium hydroxide at a concentration of 0.5 N to 5 N at room temperature to 100° C. for a period between 0.5 h and 24 h. A method similar to that outlined in Scheme 1 is reported in PCT Publication Number WO 03/076427. Acylation of (H1) using a substituted benzoyl chloride in the presence of a base such as triethylamine or a substituted benzoic acid in the presence of coupling reagents such as EDAC and HOBt affords the compounds of the type (I1).

Reductive amination of imidazocarboxaldehyde (A1) with a N-protected amino alcohol (B1) in the presence of a suitable reducing agent, for example sodium triacetoxyborohydride, yields compound (C1). Imidazocarboxaldehydes of type (A1) are either commercially available or can be prepared by methods known in the art. Conversion of the alcohol moiety in (C1) to the chloride (D1) can be accomplished, for example, using thionyl chloride or by many methods known in the art and are described in *Comprehensive Organic Transformations: A Guide to Functional Group Preparation*, pp. 385-439, Richard C. Larock 1989 VCH Publishers, Inc. Cyclization of (D1) to the imidazo[1,5a]pyrazine scaffold (E1) is accomplished using a base, for example triethylamine, in a solvent like dioxane. For examples, where R is a hydrogen, deprotonation of (E1) using a suitable base, for example n-butyllithium, followed by quenching with bromine affords compounds of the type (F1). Suzuki type cross coupling [A. Suzuki et. al., *J. Am. Chem. Soc.*, 1989, 111, 513; A. Suzuki, *J. Organomet. Chem.*, 1999, 576, 147; and Zapf, Alexander., *Transition Metals for Organic Synthesis* (2nd Edition)

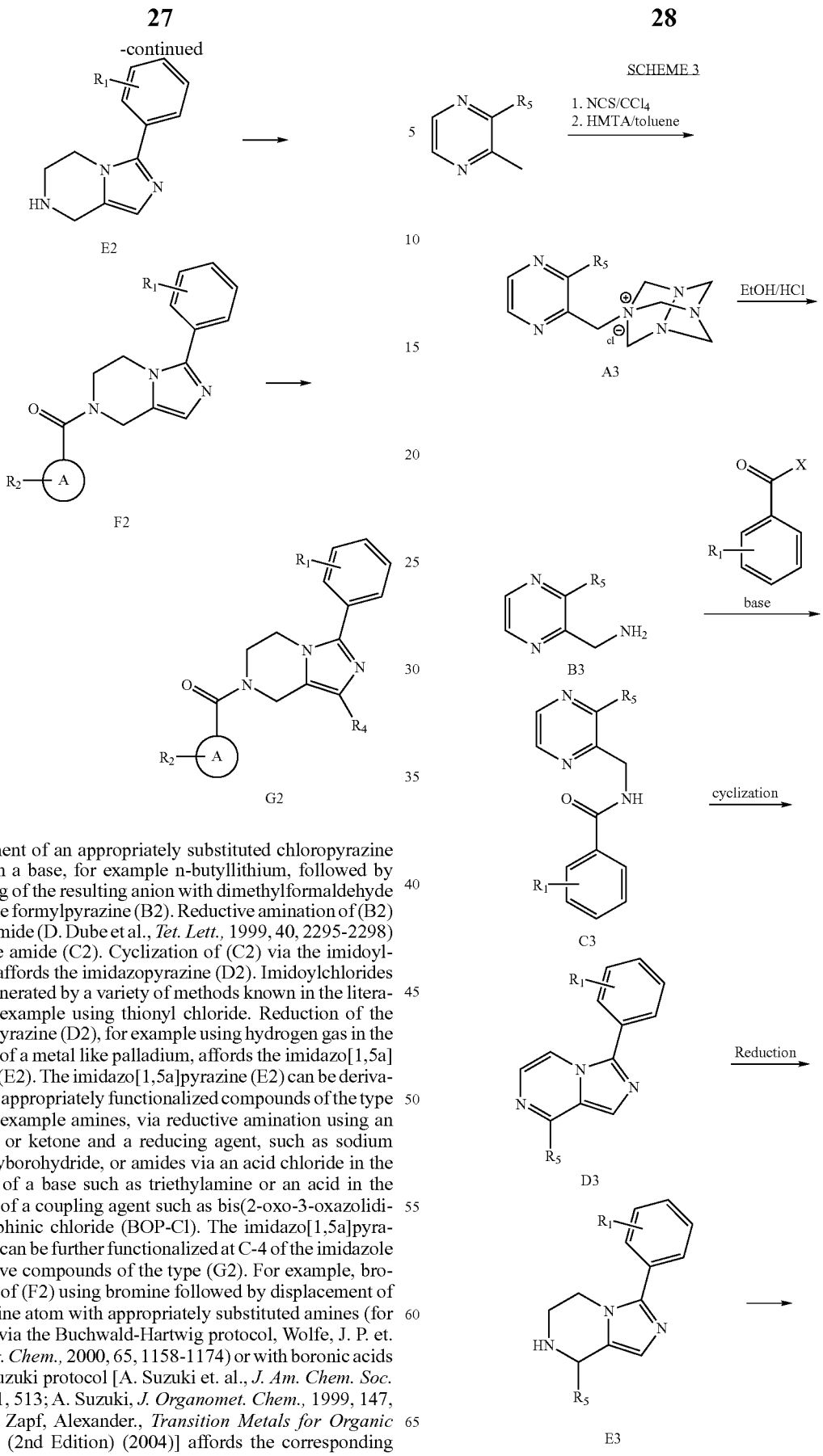

SCHEME 3

Treatment of an appropriately substituted chloropyrazine (A2) with a base, for example n-butyllithium, followed by quenching of the resulting anion with dimethylformaldehyde affords the formylpyrazine (B2). Reductive amination of (B2) with an amide (D. Dube et al., *Tet. Lett.*, 1999, 40, 2295-2298) yields the amide (C2). Cyclization of (C2) via the imidoylchloride affords the imidazopyrazine (D2). Imidoylchlorides can be generated by a variety of methods known in the literature, for example using thionyl chloride. Reduction of the imidazopyrazine (D2), for example using hydrogen gas in the presence of a metal like palladium, affords the imidazo[1,5a]pyrazine (E2). The imidazo[1,5a]pyrazine (E2) can be derivatized into appropriately functionalized compounds of the type (F2), for example amines, via reductive amination using an aldehyde or ketone and a reducing agent, such as sodium triacetoxyborohydride, or amides via an acid chloride in the presence of a base such as triethylamine or an acid in the presence of a coupling agent such as bis(2-oxo-3-oxazolidinyl)phosphinic chloride (BOP-Cl). The imidazo[1,5a]pyrazine (F2) can be further functionalized at C-4 of the imidazole ring to give compounds of the type (G2). For example, bromination of (F2) using bromine followed by displacement of the bromine atom with appropriately substituted amines (for example via the Buchwald-Hartwig protocol, Wolfe, J. P. et. al., *J. Org. Chem.*, 2000, 65, 1158-1174) or with boronic acids via the Suzuki protocol [A. Suzuki et. al., *J. Am. Chem. Soc.* 1989, 111, 513; A. Suzuki, *J. Organomet. Chem.*, 1999, 147, 576, and Zapf, Alexander., *Transition Metals for Organic Synthesis* (2nd Edition) (2004)] affords the corresponding amino substituted or alkyl/aryl/heteroaryl substituted (G2).

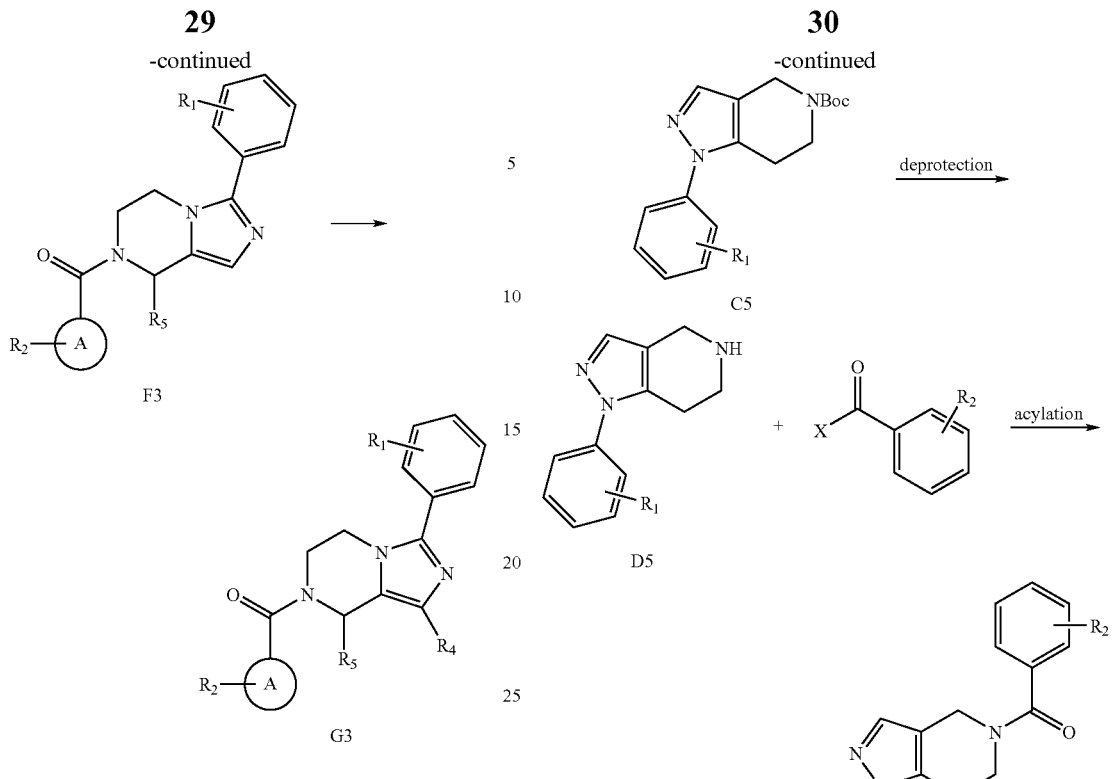

Halogenation of an appropriately substituted methylpyrazine followed by treatment with an aminating agent and hydrolysis affords the amino substituted pyrazine (B3). Halogenation of methylpyrazine can be accomplished using a variety of halogenating agents, for example N-chlorosuccinimide or N-bromosuccinimide. A variety of aminating agents are commercially available, for example hexamethyltetramine (HMTA) or di-t-butyl iminodicarboxylate. Coupling of the aminopyrazine (B3) with an appropriately substituted acid chloride in the presence of a base, for example triethylamine, or an acid in the presence of an of a coupling agent, such as bis(2-oxo-3-oxazolidinyl)phosphinic chloride (BOP-Cl) or benzotriazol-1-yloxytris(dimethylamino)phosphoniumhexafluorophosphate (BOP), affords the amide (C3). The amide (C3) can be processed in a similar fashion to that outlined for Scheme 2 to afford (G3).

Alternative Route:

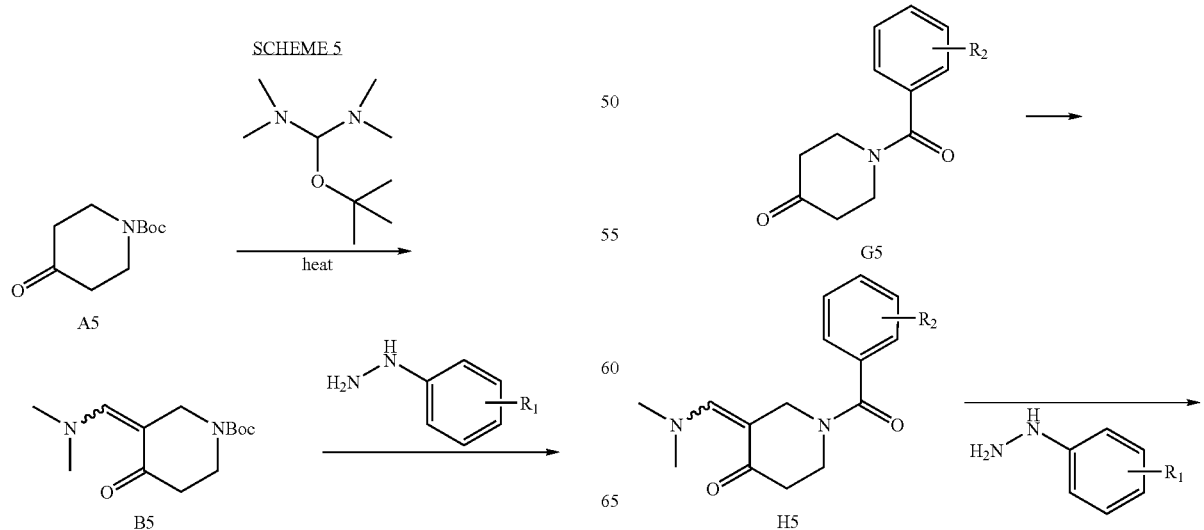

Compounds of the type (E5) can be prepared as outlined in Scheme 5. Enamination of tert-butyl-4-oxopiperidine-1-carboxylate (A5) using an appropriate enamination reagent such as Brederick's reagent [tert-butoxy-bis(dimethylamino)methane] affords the vinylogous amide (B5). Condensation of (B5) with a substituted aryl hydrazine under appropriate conditions (R. Olivera et al., *J. Org. Chem.*, 2000, 65, 7010-7019) yields the bicyclic pyrazole (C5). Deprotection of the piperidine moiety using standard conditions known in the art, for example anhydrous HCl in dioxane, affords the amine (D5). Acylation of (D5) via a substituted benzoyl chloride in the presence of a base, such as triethylamine, or a substituted benzoic acid in the presence of coupling reagents, such as EDAC and HOBt, affords the compounds of the type (E5). An alternative route to compounds of the type (E5) can be used whereby 4-piperidone hydrate hydrochloride (F5) is acylated as described above for (D5) to afford (G5). Enamination of (G5) as described above for (A5) provides (H5). Finally, condensation of (H5) with a substituted aryl hydrazine as described above for (B5) affords compounds of the type (E5).

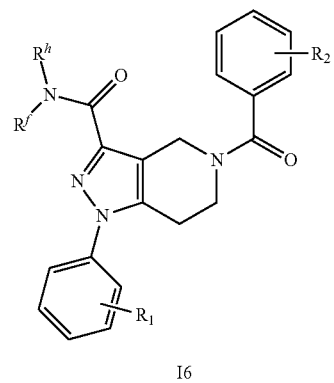

I6

Compounds of the type (I6) can be prepared similar to the methods reported in PCT Publication Number WO 03/047520 as outlined in Scheme 6. Condensation of tert-butyl-4-oxopiperidine-1-carboxylate (A6) with morpholine under dehydrating conditions, such as in the presence of para-toluenesulphonic acid, in a solvent, such as toluene, at reflux affords enamine (B6). Diazotization of a substituted aniline (C6) using suitable reagents, such as HCl and sodium nitrite, followed by condensation of ethylchloroacetoacetate in the presence of a base, such as sodium acetate, affords the chloroimidate (D6). Condensation of (B6) and (D6) in the presence of a base such as triethylamine in a solvent such as acetone yields the substituted bicyclic pyrazole (E6). Deprotection of the piperidine moiety using standard conditions known in the art, for example anhydrous HCl in dioxane, affords the amine (F6). Acylation of (F6) using a substituted benzoyl chloride in the presence of a base such as triethylamine or a substituted benzoic acid in the presence of coupling reagents such as EDAC and HOBt affords the compounds of the type (G6). Finally, hydrolysis under suitable conditions, such as aqueous sodium hydroxide in methanol, to afford (H6) followed by amide bond coupling with an amine using suitable coupling reagents such as EDAC and HOBt affords compounds of the type (I6).

SCHEME 7

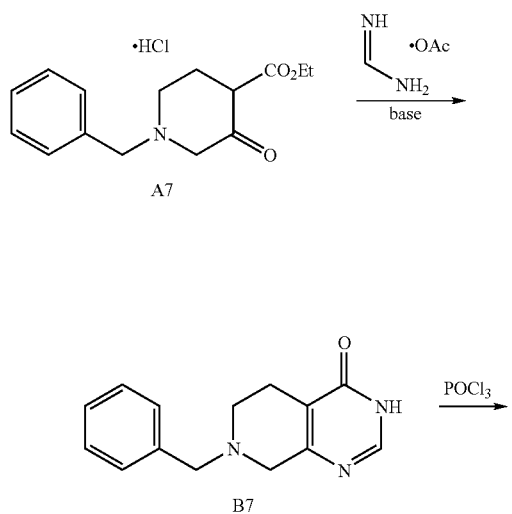

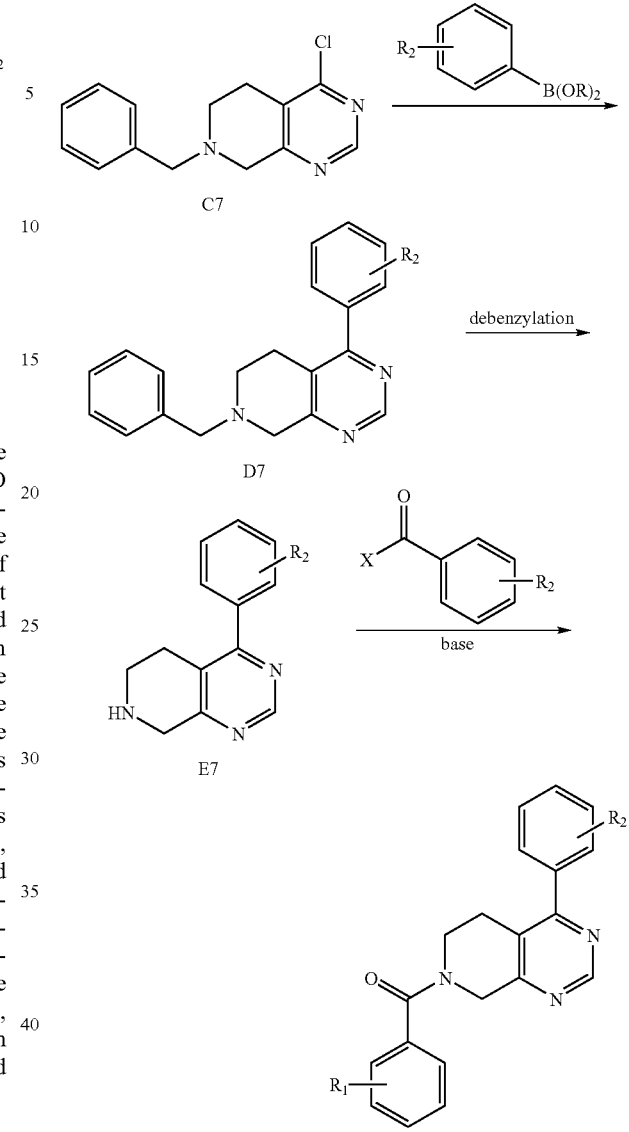

Compounds of the type (F7) can be prepared as outlined in Scheme 7. Ethyl-1-benzyl-3-oxo-4-piperidine carboxylate hydrochloride can be condensed with formamidine acetate in the presence of a base such as sodium methoxide in a solvent such as methanol to afford the bicyclic pyrimidinone (B7). Chlorination under suitable conditions such as in the presence of $POCl_3$ affords the chloride (C7). Suzuki type cross coupling [A. Suzuki et. al., *J. Am. Chem. Soc.*, 1989, 111, 513; A. Suzuki, *J. Organomet. Chem.*, 1999, 576, 147; and Zapf, Alexander., *Transition Metals for Organic Synthesis* (2nd Edition) (2004), 1 211-229] of (C7) with an aryl boronic acid or ester in the presence of a suitable catalyst such as tetrakis (triphenylphosphine) palladium affords compounds of the type (D7). After cross coupling has been performed the product is debenzylated. The choice of conditions for debenzylation will be readily apparent to one skilled in the art of organic chemistry. Such considerations and methods are, for example, described by Greene, Theodora W. and Wuts, Peter G. M. in *Protective Groups in Organic Synthesis*, 3rd Ed. (1999) (John Wiley and Sons, Inc., New York, N.Y.). A preferred method for debenzylation of (D7) uses 1-chloroethyl-chloroformate in the presence of a suitable base such as DIPEA in a suitable solvent such as dichloromethane to afford the amine (E7). Finally, acylation of (E7) using a substituted benzoyl chloride in the presence of a base, such as triethylamine, or a substituted benzoic acid in the presence of coupling reagents, such as EDAC and HOBt, affords the compounds of the type (F7).

EXAMPLES

The following Examples are offered as illustrative as a partial scope of the invention and are not meant to be limiting of the scope of the invention. Unless otherwise indicated, they have been prepared, isolated and characterized using the Schemes and other methods disclosed herein. The abbreviations used herein are defined above.

Example 1

2,4-difluorophenyl(3-(2-(trifluoromethyl)phenyl)-5,6-dihydroimidazo[1,5-a]pyrazin-7(8H)-yl)methanone

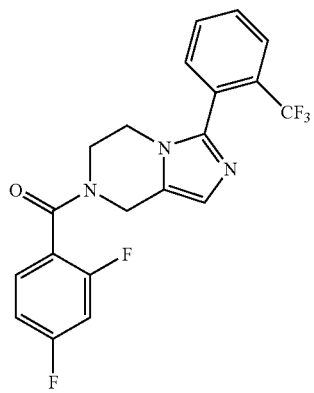

1

Step A 2-(4-methoxybenzylamino)ethanol

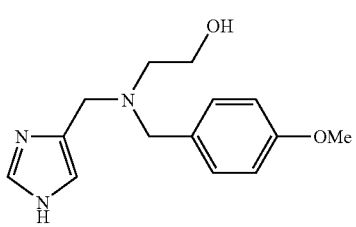

a

A 1 L round bottom flask is charged with 2-aminoethanol (29 g, 213 mmol), 4-methoxybenzaldehyde (39 g, 639 mmol), methanol (250 mL) and acetic acid (75 mL) under a nitrogen atmosphere. The contents were cooled to 0° C. and sodium triacetoxyborohydride (50 g, 234 mmol) was added over a 20 minute period. The reaction mixture was stirred at room temperature for 18 hours, concentrated under reduced pressure and partitioned between water (500 mL) and ethyl acetate (500 mL). The ethyl acetate layer was washed with 3N HCl (400 mL). The HCl layer is separated, cooled to 0° C., made basic using 6N NaOH and extracted with dichloromethane (2×100 mL). The dichloromethane layer was dried over sodium sulfate and concentrated under reduced pressure to yield the title compound a as an oil (20 g). $^1$H-NMR of the oil was consistent with the desired structure.

Step B 2-(((1H-imidazol-4-yl)methyl)(4-methoxybenzyl)amino)ethanol

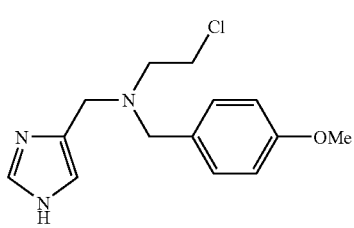

b

To a heterogeneous mixture of 1H-imidazole-4-carbaldehyde (8.0 g, 83.33 mmol) and 2-(4-methoxybenzylamino)ethanol (Step A, 18.1 g, 99.9 mmol) in anhydrous THF (100 mL) was added sodium triacetoxyborohydride (21.2 g, 99.9 mmol) over a 15 minute period at room temperature. The reaction mixture was stirred at room temperature for 18 hours, concentrated under reduced pressure and partitioned between saturated aqueous sodium bicarbonate (200 mL) and dichloromethane (2×200 mL). The dichloromethane layer was dried over sodium sulfate, concentrated under reduced pressure and purified by silica gel flash chromatography using dichloromethane and methanol (9:1, 800 mL) followed by dichloromethane:methanol:2.0M ammonia in methanol (850:100:50 mL) to afford the title compound b as an oil (14.5 g), [M+H]$^+$ 262.21.

Step C

N—((1H-imidazol-4-yl)methyl)-2-chloro-N-(4-methoxybenzyl)ethanamine c

To a solution of 2-(((1H-imidazol-4-yl)methyl)(4-methoxybenzyl)amino)ethanol (Step B, 14.5 g, 55.55 mmol) in anhydrous dioxane (100 mL) was added thionyl chloride (16.5 mL, 222.2 mmol) over a 10 minute period. The reaction mixture was heated at 60° C. for 3 hours, cooled to room temperature and partitioned under reduced pressure. The contents of the flask were azeotroped with dioxane (2×100 mL)

and toluene (2×100 mL). The white solid c that separates out is filtered and used as such for the subsequent step without further purification (19.0 g).

Step D 7-(4-methoxybenzyl)-5,6,7,8-tetrahydroimidazo[1,5-a]pyrazine

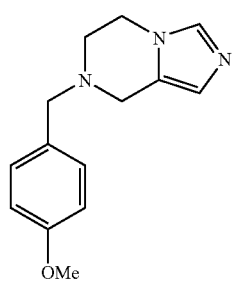

d

To N—((1H-imidazol-4-yl)methyl)-2-chloro-N-(4-methoxybenzyl)ethanamine (19.0 g, 53.97 mmol) in anhydrous dioxane (100 mL) was added triethylamine (27 mL, 194.3 mmol) over a period of 15 minutes at room temperature. The reaction mixture was heated at 90° C. for 6 hours, stirred at room temperature for 18 hours and partitioned between 1N NaOH (75 mL) and ethyl acetate (2×200 mL). The sodium hydroxide layer is reextracted with dichloromethane (100 mL). The ethyl acetate and dichloromethane layers are combined, dried over sodium sulfate, concentrated under reduced pressure and purified by silica gel flash chromatography using dichloromethane and methanol (9.5:0.5, 400 mL) to yield the title compound d (3.9 g), [M+H]$^+$ 244.25.

Step E 3-bromo-7-(4-methoxybenzyl)-5,6,7,8-tetrahydroimidazo[1,5-a]pyrazine

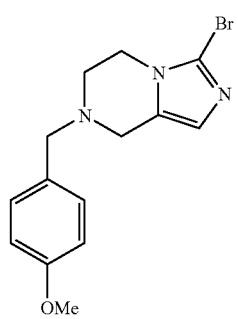

e

To a solution of 0.2 g (0.82 mmol) 7-(4-methoxybenzyl)-5,6,7,8-tetrahydroimidazo[1,5-a]pyrazine (Step D) in anhydrous THF (5 mL), cooled to −78° C. was added n-BuLi (0.36 mL, 0.90 mmol, 2.5 M solution in hexane) dropwise over a 15 minute period. The reaction mixture was stirred at −78° C. for 15 minutes, and carbontetrabromide (0.3 g, 0.9 mmol) was added dropwise over a 3 minute period. The reaction was stirred at −78° C. for 20 minutes and quenched by the addition of saturated ammonium chloride (3 mL) at −78° C. The reaction mixture was bought to room temperature and stirred at room temperature for 10 minutes and partitioned between brine (20 mL) and dichloromethane (30 mL). The dichloromethane layer was dried over sodium sulfate, concentrated under reduced pressure and purified by silica gel flash chromatography using methanol and ethyl acetate (0.5:9.5, 300 mL) to afford the title compound e (0.13 g) as an oil, [M+H]$^+$ 324.

Step F 7-(4-methoxybenzyl)-3-(2-(trifluoromethyl)phenyl)-5,6,7,8-tetrahydroimidazo[1,5-a]pyrazine

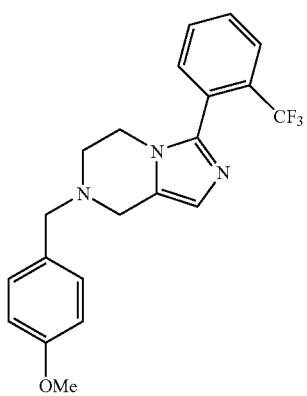

f

To 0.025 g (0.77 mmol) of 3-bromo-7-(4-methoxybenzyl)-5,6,7,8-tetrahydroimidazo[1,5-a]pyrazine (Step E) in dioxane (12 mL) and water (4 mL) are sequentially added 2-(trifluoromethyl)phenylboronic acid (0.176 g, 0.924 mmol), potassium carbonate (0.32 g, 2.31 mmol) and etrakis(triphenylphosphine)palladium(0) (0.089 g, 0.077 mmol) under a nitrogen atmosphere. The contents were heated at 100° C. for 20 hours, cooled to room temperature, concentrated under reduced pressure and partitioned between dichloromethane (50 mL) and brine (20 mL). The dichloromethane layer was dried over sodium sulfate, concentrated under reduced pressure and purified by silica gel flash chromatography using dichloromethane/methanol (9.7:0.3, 400 mL) to afford the title compound f (0.03 g), [M+H]$^+$ 388.14.

Step G 3-(2-(trifluoromethyl)phenyl)-5,6,7,8-tetrahydroimidazo[1,5-a]pyrazine

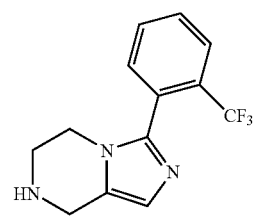

g

To a solution of 7-(4-methoxybenzyl)-3-(2-(trifluoromethyl)phenyl)-5,6,7,8-tetrahydroimidazo[1,5-a]pyrazine (Step F, 25 mg) in methanol, at 0° C. and under a nitrogen atmosphere was added palladium hydroxide on carbon (15 mg, 20 wt % Pd-Degussa type, E101) and the contents hydrogenated at 40 psi for 14 hours. The reaction mixture was filtered and the filter cake washed with methanol (2×10 mL). The filtrate was concentrated under reduced pressure and azeotroped with dichloromethane (2×20 mL) and ethyl acetate (2×20 mL). The oil that is obtained g (20 mgs) was used as such for the subsequent step without further purification.

Step H 2,4-difluorophenyl(3-(2-(trifluoromethyl)phenyl)-5,6-dihydroimidazo[1,5-a]pyrazin-7(8H)-yl)methanone

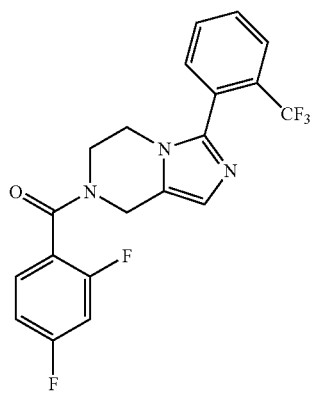

1

To a solution of 3-(2-(trifluoromethyl)phenyl)-5,6,7,8-tetrahydroimidazo[1,5-a]pyrazine (20 mgs, 0.07 mmol) in anhydrous DMF (1 mL) and diisopropylethylamine (28 µL, 0.14 mmol) was added 2,4-difluorobenzoyl chloride and the contents stirred at room temperature for 15 minutes. The reaction mixture was subjected to reverse phase preparative HPLC (YMC S5 20×100 mm, 10 min. run, solvent A: 10% MeOH: 90% H$_2$O: 0.1% TFA, solvent B: 90% MeOH, 10% H$_2$O, 0.1% TFA), the desired fractions were collected, concentrated under reduced pressure and partitioned between dichloromethane (20 mL) and saturated aqueous sodium bicarbonate (10 mL). The dichloromethane layer was dried over sodium sulfate and concentrated under reduced pressure to yield the title compound 1 (4.0 mgs), [M+H]$^+$ 408.24.

Example 2

2,4-difluorophenyl(3-(2,4-difluorophenyl)-5,6-dihydroimidazo[1,5-a]pyrazin-7(8H)-yl)methanone

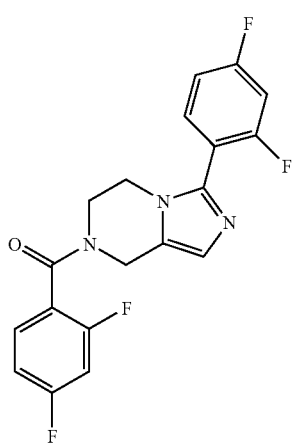

2

Step A 3-chloropyrazine-2-carbaldehyde

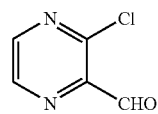

a

A flame dried and cooled 100 mL round bottom flask was charged with 2,2,6,6-tetramethylpiperidine (2.5 mL, 14.96 mmol) and anhydrous THF (25 mL) under a nitrogen atmosphere. The contents were cooled to −78° C. and n-butyllithium (2.5 M in hexane, 5.7 mL, ~14.28 mmol) was added dropwise over a 5 minute period. The reaction mixture was stirred at −78° C. for 5 minutes, bought to 0° C. and stirred at 0° C. for 25 minutes. The reaction mixture was recooled to −78° C. and 2-chloropyrazine (0.78 g, 1 mL, 6.8 mmol) was added over a 3 minute period. After 30 minutes at −78° C., anhydrous DMF (0.99 mL, 13.6 mmol) was added over 3 minutes and the contents stirred at −78° C. for a further 30 minutes. The reaction mixture was bought to 0° C., stirred at 0° C. for 15 minutes, recooled to −78° C. and quenched by the addition of acetic acid (4 mL) in THF (10 mL). The reaction mixture was stirred at room temperature for 10 minutes and partitioned between ethyl acetate (60 mL) and brine (30 mL). The ethyl acetate layer is separated, dried over sodium sulfate, concentrated under reduced pressure and purified by silica gel flash chromatography using dichloromethane and ethyl acetate (9.5:0.5, 400 mL) to yield the title compound a (950 mg). $^1$H-NMR of the compound was consistent with the desired structure.

Step B

N-((3-chloropyrazin-2-yl)methyl)-2,4-difluorobenzamide

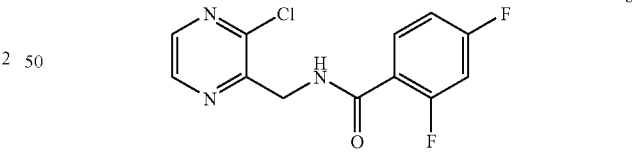

b

To 3-chloropyrazine-2-carbaldehyde (Step A, 0.95 g, 6.69 mmol) in toluene (20 mL) were sequentially added triethylsilane (3.3 mL, 20.07 mmol) and TFA (1.52 mL, 20.07 mmol) at room temperature. The reaction mixture was heated at 80° C. for 3.5 hours, cooled to room temperature and concentrated under reduced pressure. Ethyl acetate (20 mL) was added and the solid that separates out was filtered. The filtrate was concentrated under reduced pressure and purified by silica gel flash chromatography using dichloromethane and ethyl acetate (9:0.5, 300 mL to 9:1, 400 mL). The desired fractions were collected, concentrated under reduced pressure and used as b for the subsequent step.

Step C 8-chloro-3-(2,4-difluorophenyl)imidazo[1,5-a]pyrazine

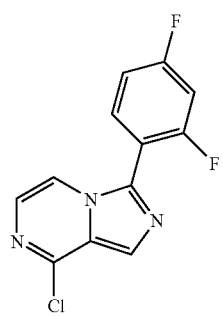

c

To N-((3-chloropyrazin-2-yl)methyl)-2,4-difluorobenzamide (Step B, 1.15 g, 4.05 mmol) in toluene (20 mL) were sequentially added phosphoryl chloride (0.5 mL, 5.26 mmol) and diisopropylethylamine (1.05 mL, 5.67 mmol) and the contents heated at 120° C. for 6 hours. The reaction mixture is cooled to room temperature, and phosphoryl chloride (1 mL) and diisopropylethylamine (2 mL) are added and the contents heated at 120° C. for an additional 4 hours. The reaction mixture was stirred at room temperature for 3½ days, concentrated under reduced pressure and partitioned between ethyl acetate (100 mL) and water (50 mL). The ethyl acetate layer was washed with saturated aqueous sodium bicarbonate (30 mL) and water (30 mL), dried over sodium sulfate and concentrated under reduced pressure. To the residue that is obtained was added 60 mL of hexane/ethyl acetate mixture (3.5:1.5). The solid that was obtained is filtered. The filtrate was concentrated under reduced pressure and purified by silica gel flash chromatography using hexane/ethyl acetate (3.5:1.5, 400 mL to 3:2, 300 mL). The desired fractions were isolated and concentrated under reduced pressure to yield the title compound c as a solid (240 mgs), [M+H]$^+$ 266.16.

Step D 3-(2,4-difluorophenyl)-5,6,7,8-tetrahydroimidazo[1,5-a]pyrazine

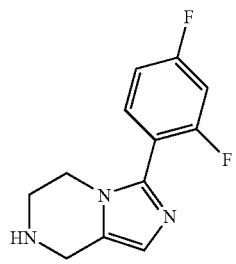

d

To a solution of 8-chloro-3-(2,4-difluorophenyl)imidazo[1,5-a]pyrazine (Step C, 200 mg) in methanol, at 0° C. and under a nitrogen atmosphere was added palladium on carbon (75 mgs, 10 wt % Pd) and the contents hydrogenated at 50 psi for 20 hours. The reaction mixture was filtered and the filter cake washed with methanol (2×10 mL). The filtrate was concentrated under reduced pressure to yield a solid d (175 mgs) that was used as such for the subsequent step without further purification.

Step E 2,4-difluorophenyl(3-(2,4-difluorophenyl)-5,6-dihydroimidazo[1,5-a]pyrazin-7(8H)-yl)methanone

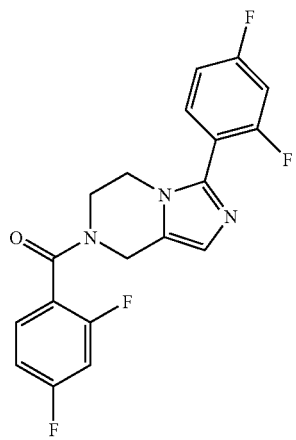

2

This compound 2 was prepared as described for Example 1 (Step H) starting from 50 mg of 3-(2,4-difluorophenyl)-5,6,7,8-tetrahydroimidazo[1,5-a]pyrazine (Step D) and 2,4-difluorobenzoyl chloride. Yield: 14 mgs, [M+H]$^+$ 376.18.

Example 3

(3-(2,4-difluorophenyl)-5,6-dihydroimidazo[1,5-a]pyrazin-7(8H)-yl)(6-methoxy-1H-pyrrolo[2,3-b]pyridin-5-yl)methanone

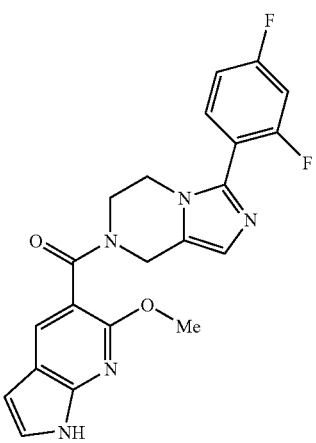

3

To 3-(2,4-difluorophenyl)-5,6,7,8-tetrahydroimidazo[1,5-a]pyrazine (Example 2, Step D, 0.29 g, 1.23 mmol) in anhydrous DMF (3 mL) were sequentially added 6-methoxy-1H-pyrrolo[2,3-b]pyridine-5-carboxylic acid (WO 04/032874, 0.237 g, 1.23 mmol), benzotriazol-1-yloxytris(dimethylamino)phosphoniumhexafluorophosphate (1.1 g, 2.46 mmol) and triethylamine (0.51 mL, 3.69 mmol) at room temperature. The reaction mixture was stirred at room temperature for 70 hours and partitioned between ethyl acetate (75 mL) and saturated aqueous sodium bicarbonate (30 mL). The ethyl acetate layer was washed with 10% lithium chloride solution (2×30 mL), dried over sodium sulfate and purified by silica gel flash chromatography using dichloromethane and methanol (9.5:0.5, 400 mL) to yield the title compound 3 (0.5 g), [M+H]+ 410.25.

Example 4

2-(5-(3-(2,4-difluorophenyl)-5,6,7,8-tetrahydroimidazo[1,5-a]pyrazine-7-carbonyl)-6-methoxy-1H-pyrrolo[2,3-b]pyridin-3-yl)-N,N-dimethyl-2-oxoacetamide

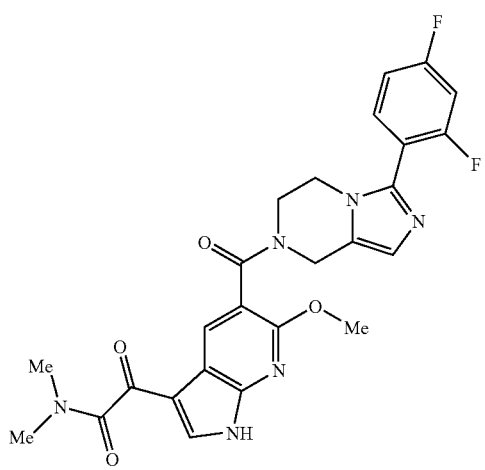

To a solution of (3-(2,4-difluorophenyl)-5,6-dihydroimidazo[1,5-a]pyrazin-7(8H)-yl)(6-methoxy-1H-pyrrolo[2,3-b]pyridin-5-yl)methanone (Example 3, 0.09 g, 0.22 mmol) in dichloromethane (2 mL) and cooled to 0° C., was added oxalyl chloride (58 μL, 0.66 mmol) over a 3 minute period. The reaction mixture was stirred at room temperature for 45 minutes, concentrated under reduced pressure, and dimethylamine (2.0M in THF, 0.66 mL, 1.32 mmol) was added over a period of 3 minutes at room temperature. The reaction mixture was stirred at room temperature for 18 hours and partitioned between dichloromethane (20 mL) and saturated aqueous sodium bicarbonate (10 mL). The dichloromethane layer is separated, dried over sodium sulfate, concentrated under reduced pressure and subjected to reverse phase preparative HPLC (YMC S5 20×100 mm, 10 min. run, solvent A: 10% MeOH: 90% H₂O: 0.1% TFA, solvent B: 90% MeOH, 10% H₂O, 0.1% TFA). The desired fractions were collected, concentrated under reduced pressure and partitioned between dichloromethane (20 mL) and saturated aqueous sodium bicarbonate (10 mL). The dichloromethane layer was dried over sodium sulfate and concentrated under reduced pressure to yield the title compound 4 (1.4 mg), [M+H]+ 509.01.

Example 5

(6-chloro-1-methyl-1H-indol-5-yl)(3-(2,4-difluorophenyl) -5,6-dihydroimidazo[1,5-a]pyrazin-7(8H)-yl)methanone

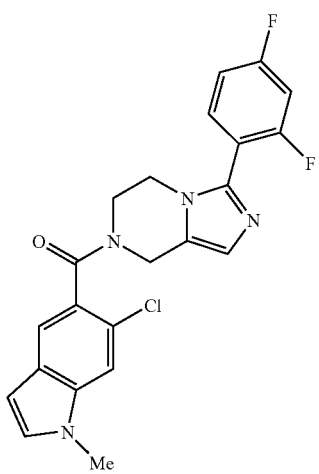

Step A

Di-tert-butylimino(pyrazin-2-ylmethyl)carbamate

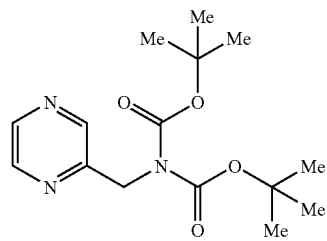

To a solution of 2-(chloromethyl)pyrazine (*Synthesis*, 1984, 676-679, 26 g, 48% pure) in DMF (260 mL) was added anhydrous potassium carbonate (41.6 g) and di-t-butyl iminodicarboxylate (26 g). The reaction mixture was heated at 85° C. for 4 h, concentrated under reduced pressure and partitioned between ethyl acetate and water. The ethyl acetate layer was separated, dried over sodium sulfate, concentrated under reduced pressure and purified by silica gel flash chromatography using petroleum ether: ethyl acetate (5% to 20%)

to afford the title compound a as a solid (27 g). $^1$H NMR (400 MHz) (CDCl$_3$) δ 1.49 (s, 18H), 4.98 (2H), 8.47 (d, J=4 Hz, 1H), 8.52 (2H).

Step B

Pyrazin-2-ylmethanamine dihydrochloride

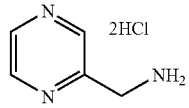
b

Di-tert-butylimino(pyrazin-2-ylmethyl)carbamate (Step A, 20 g, 6.51 mmol) was dissolved in ethyl acetate (100 mL), and a solution of HCl in ethyl acetate (2 N, 100 mL) was added at room temperature. After 3 h, the reaction mixture was filtered, washed with ethyl acetate under a N$_2$ atmosphere and dried to yield the title compound b as a hygroscopic solid (9.7 g), [M+H]$^+$ 110.

Alternate Method

An alternate approach to the title compound b involves the reaction of 2-(chloromethyl)pyrazine with hexamethylenetetramine followed by hydrolysis of the salt with concentrated hydrochloric acid in ethanol (as shown in scheme 3)

Step C 2,4-difluoro-N-(pyrazin-2-ylmethyl)benzamide

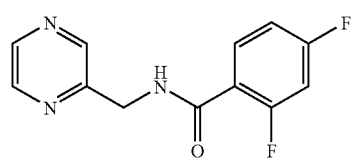
c

To pyrazin-2-ylmethanamine dihydrochloride (Step B, 18.0 g, 98.9 mmol) was added dioxane (180 mL) followed by disopropylethylamine (40.4 g, 316 mmol) and the mixture stirred at room temperature for 0.25 hours. 2,4-Difluorobenzoyl chloride (21.45 g, 118.68 mmol) was added dropwise at 0° C. The reaction mixture was stirred at room temperature overnight, concentrated under reduced pressure and partitioned between ethyl acetate and aq. NaOH solution. The ethyl acetate layer was washed with brine, dried over sodium sulfate concentrated under reduced pressure and purified by silica gel flash chromatography using petroleum ether: ethyl acetate system (5% to 40%) to afford the title compound c as a solid. (14.0 g), [M+H]$^+$ 249.9.

Step D 3-(2,4-difluorophenyl)imidazo[1,5-a]pyrazine

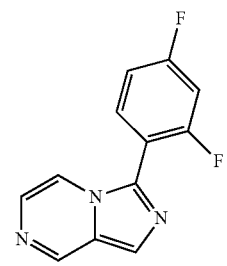
d

To a suspension of 2,4-difluoro-N-(pyrazin-2-ylmethyl)benzamide (Step C, 13.0 g, 52.2 mmol) in dry toluene (140 mL) was added distilled phosphoryl chloride (10.4 mL) dropwise at 0° C. The reaction mixture was refluxed for 2.5 hours, concentrated under reduced pressure and partitioned between ethyl acetate and water. The ethyl acetate layer is washed with saturated aqueous sodium bicarbonate and brine, dried over sodium sulfate, concentrated under reduced pressure and purified by silica gel flash chromatography using chloroform: methanol system (0% to 1% of methanol). The desired fractions collected and concentrated under reduced pressure to afford the title compound d as a solid. (Yield 4.5 g), [M+H]$^+$ 231.9.

Step E 3-(2,4-difluorophenyl)-5,6,7,8-tetrahydroimidazo[1,5-a]pyrazine

Also See Example 2, Step D

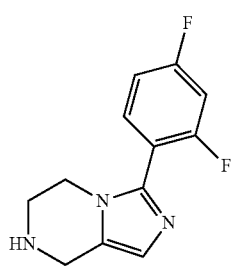
e 3-(2,4-difluorophenyl)imidazo[1,5-a]pyrazine (Step D, 5.0 g) was dissolved in methanol (50 mL), and 10% palladium hydroxide (2.0 g) was added under N₂ atmosphere. The contents were hydrogenated at 5 kg/cm⁻² pressure over night, concentrated under reduced pressure and purified by silica gel flash chromatography using chloroform:methanol (0% to 9% of methanol). The desired fractions were collected, concentrated under reduced pressure and redissolved in a mixture of ethyl acetate and hydrochloric acid in dioxane. The solid that precipitates out was filtered and triturated repeatedly with ethyl acetate. The hydrochloric acid salt was dissolved in sat. bicarbonate solution and extracted in ethyl acetate. The ethyl acetate layer was dried over sodium sulfate and concentrated to afford the title compound e (1.9 g), [M+H]⁺ 235.9.

Step F (6-chloro-1H-indol-5-yl)(3-(2,4-difluorophenyl)-5,6-dihydroimidazo[1,5-a]pyrazin-7(8H)-yl)methanone This compound was prepared in a similar fashion to that outlined in Example 3, starting from 3-(2,4-difluorophenyl)-5,6,7,8-tetrahydroimidazo[1,5-a]pyrazine (Step F, 0.1 g) and 6-chloro-1-methyl-1H-indole-5-carboxylic acid (WO 04/022712) to yield the title compound 5 (0.15 g), [M+H]⁺ 427.09.

Example 6

2-(6-chloro-5-(3-(2,4-difluorophenyl)-5,6,7,8-tetrahydroimidazo[1,5-a]pyrazine-7-carbonyl)-1-methyl-1H-indol-3-yl)-N,N-dimethyl-2-oxoacetamide

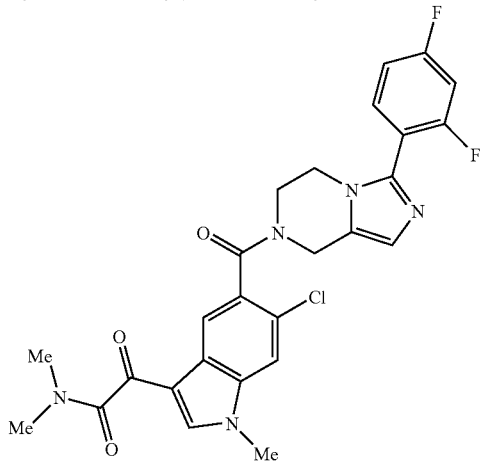

This compound was prepared in a similar fashion to that outlined in Example 4 starting from (6-chloro-1H-indol-5-yl)(3-(2,4-difluorophenyl)-5,6-dihydroimidazo[1,5-a]pyrazin-7(8H)-yl)methanone (Example 5, 0.15 g) to afford the title compound 6 as a solid (0.093 g), [M+H]⁺ 526.12.

Examples 7 to 41

Compounds listed in Tables 1 and 2 were prepared using methods described in Examples 1 to 6.

TABLE 1

| Ex. No. | G | HPLC ret. Time, min. (column conditions)* | [M + H]⁺ |
|---|---|---|---|
| 7(±)¹ | 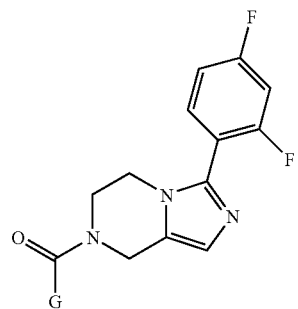 | 1.39 (A) | 551.17 |

TABLE 1-continued
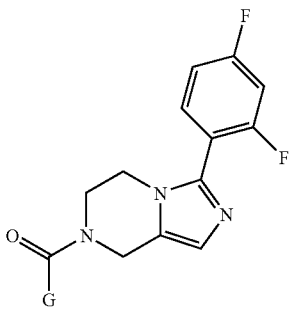
| Ex. No. | G | HPLC ret. Time, min. (column conditions)* | [M + H]⁺ |
|---|---|---|---|
| 8(±) | 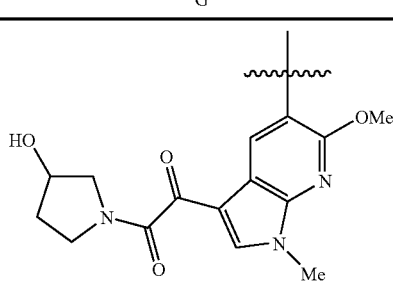 | 1.98 (B) | 565.34 |
| 9 | 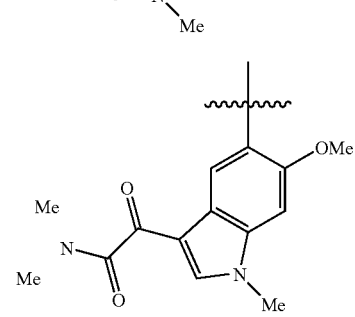 | 1.99 (A) | 423.39 |
| 10 | 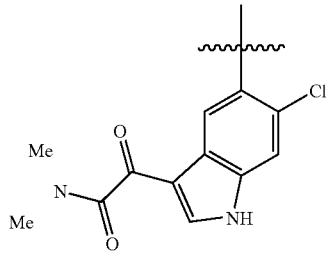 | 1.64 (A) | 522.34 |
| 11 | 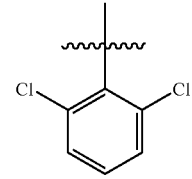 | 1.78 (A) | 512.36 |
| 12 |  | 1.85 (A) | 408.24 |

TABLE 1-continued
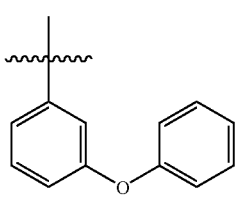
| Ex. No. | G | HPLC ret. Time, min. (column conditions)* | [M + H]+ |
|---|---|---|---|
| 13 | 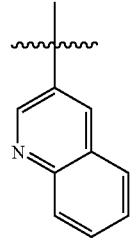 | 2.63 (C) | 432.27 |
| 14 | 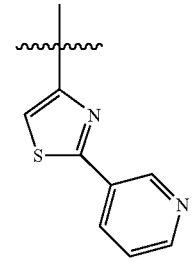 | 1.50 (C) | 391.31 |
| 15 | 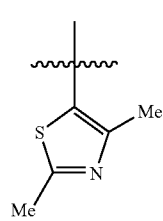 | 1.46 (C) | 424.24 |
| 16 | 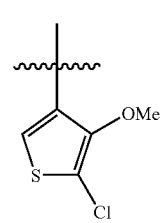 | 1.41 (C) | 375.28 |
| 17 |  | 2.15 (C) | 410.18 |

TABLE 1-continued

[Structure: 3-(2,4-difluorophenyl)-5,6,7,8-tetrahydroimidazo[1,5-a]pyrazine with N-C(=O)-G substituent]

| Ex. No. | G | HPLC ret. Time, min. (column conditions)* | [M + H]⁺ |
|---|---|---|---|
| 18 | 2,6-dimethylphenyl | 2.02 (C) | 368.28 |
| 19 | 2-chloro-4-fluorophenyl | 1.96 (C) | 392.20 |
| 20 | 3-methylthiophen-2-yl | 1.70 (C) | 360.24 |
| 21 | benzothiazol-2-yl | 2.38 (C) | 397.20 |
| 22 | benzofuran-2-yl | 2.21 (C) | 380.22 |

TABLE 1-continued
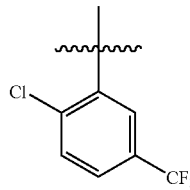
| Ex. No. | G | HPLC ret. Time, min. (column conditions)* | [M + H]+ |
|---|---|---|---|
| 23 | 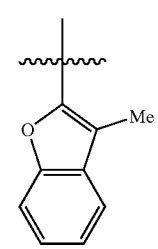 | 2.28 (C) | 442.11 |
| 24 | 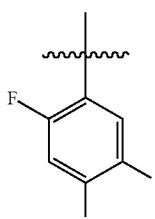 | 2.48 (C) | 394.24 |
| 25 | 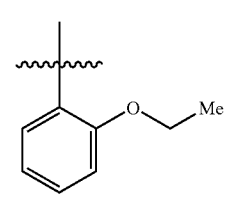 | 2.07 (C) | 390.24 |
| 26 | 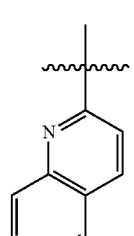 | 1.90 (C) | 384.26 |
| 27 | | 2.04 (C) | 391.24 |

TABLE 1-continued

| Ex. No. | G | HPLC ret. Time, min. (column conditions)* | [M + H]⁺ |
|---|---|---|---|
| 28 | (2,6-difluorophenyl) | 1.64 (C) | 376.26 |

¹(±)denotes a racemic compound.
*(A): YMC S5 Combiscreen ODS; 4.6 × 50 mm (4 min. gradient); Solvent A = 10% MeOH, 90% H₂O, 0.2% H₃PO₄; solvent B = 90% MeOH, 10% H₂O, 0.2% H₃PO₄.
(B): YMC C18 S; 4.6 × 50 mm (4 min. gradient); Solvent A = 10% MeOH, 90% H₂O, 0.2% H₃PO₄; solvent B = 90% MeOH, 10% H₂O, 0.2% H₃PO₄.
(C): Waters SunFire C18, 4.6 × 50 mm × 5 µM; Solvent A = 10% MeOH, 90% H₂O, 0.1% TFA; solvent B = 90% MeOH, 10% H₂O, 0.1% TFA.

TABLE 2

| Ex. No. | Structure | HPLC ret. Time, min. (column conditions)* | [M + H]⁺ |
|---|---|---|---|
| 29(±) | (structure) | 1.6 | 384.28 |
| 30(±) | (structure) | 1.89 | 416.26 |

TABLE 2-continued

| Ex. No. | Structure | HPLC ret. Time, min. (column conditions)* | [M + H]+ |
|---|---|---|---|
| 31 | 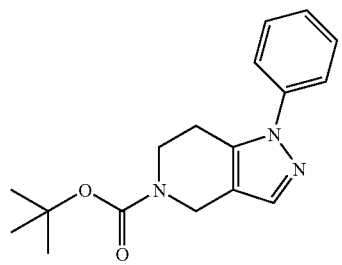 | 1.74 | 402.14 |

*(A): YMC S5 Combiscreen ODS; 4.6 × 50 mm (4 min. gradient); Solvent A = 10% MeOH, 90% H₂O, 0.2% H₃PO₄; solvent B = 90% MeOH, 10% H₂O, 0.2% H₃PO₄.

Example 32

2,6-Difluorophenyl(1-phenyl-6,7-dihydro-1H-pyrazolo[4,3-c]pyridin-5(4H)-yl)-methanone

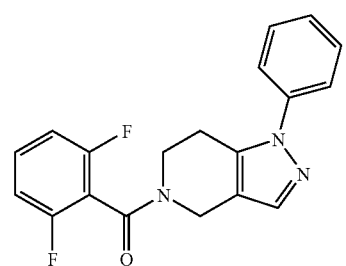

32

Step A

Tert-butyl 3-((dimethylamino)methylene)-4-oxopiperidine-1-carboxylate

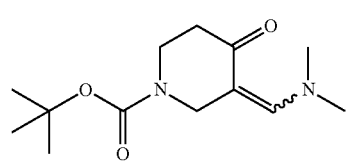

a

To tert-butoxy bis(dimethylamino)methane (20.8 mL) was added tert-butyl 4-oxopiperidine-1-carboxylate (20.0 g) and the resulting mixture was heated at 110° C. for 16 h. After cooling to rt, the mixture was purified by flash chromatography on silica gel using a gradient elution of 5% methanol in methylene chloride to 10% methanol in methylene chloride. Concentration of the combined fractions containing the major product afforded the desired product a (11.8 g) as a dark orange oil which was used in the next step without any further purification.

Step B

Tert-butyl 1-phenyl-6,7-dihydro-1H-pyrazolo[4,3-c]pyridine-5(4H)-carboxylate b

Tert-butyl 3-((dimethylamino)methylene)-4-oxopiperidine-1-carboxylate (Step A, 2.1 g, 8.3 mmol) was dissolved in 100 mL methanol, and water (50 mL) was added followed by the addition of sodium carbonate (0.53 g, 5.0 mmol) and phenyl hydrazine hydrochloride (1.43 g, 9.9 mmol). Finally, acetic acid (1 mL) was added and the resulting mixture was stirred at rt for 1 h. The mixture was made basic by adding saturated aq. sodium bicarbonate (ca. 20 mL) and the methanol was removed on a rotary evaporator. The resulting mixture was extracted with methylene chloride (3×40 mL) and the combined extracts were dried over anhyd. sodium sulfate, filtered, and concentrated to afford the crude product. Purification by flash chromatography on silica gel using 20% ethyl acetate in hexanes as the eluant afforded fractions containing the desired product. Concentration of the combined fractions afforded the desired product b as a yellow oil (1.63 g, 66%).

$^1$H NMR (400 MHz, d$^3$-MeOD): δ 7.73 (s, 1H), 7.60-7.47 (m, 5H), 4.37 (s, 2H), 3.57 (t, J=6.1 Hz, 2H), 3.17 (t, J=6.0 Hz, 2H).

Step C 1-phenyl-4,5,6,7-tetrahydro-1H-pyrazolo[4,3-c]pyridine hydrochloride

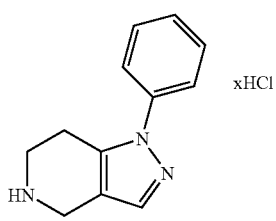

c

Tert-butyl 1-phenyl-6,7-dihydro-1H-pyrazolo[4,3-c]pyridine-5(4H)-carboxylate (Step B, 1.6 g, 5.4 mmol) was dissolved in anhyd dioxane (10 mL) and 4 N anhyd HCl in dioxane (10 mL) was added. After heating the resulting solution at 40° C. for 1.5 h, the mixture was cooled to rt and the precipitated solid was collected by vacuum filtration and rinsed with additional dioxane (10 mL). The resulting hygroscopic solid was then dissolved in methanol (~75 mL) and reconcentrated to initially yield a oil which foamed and solidified under vacuum to provide the desired product c as a light tan colored solid (1.45 g, ~100%). $^1$H NMR (400 MHz, d$^3$-MeOD): δ 7.55 (s, 1H), 7.53-7.50 (m, 4H), 7.48 (m, 1H), 4.52 (s, 2H), 3.70 (t, J=5.7 Hz, 2H), 2.83 (t, J=5.7 Hz, 2H), 1.51 (s, 9H).

Step D 2,6-difluorophenyl(1-phenyl-6,7-dihydro-1H-pyrazolo[4,3-c]pyridin-5(4H)-yl)methanone

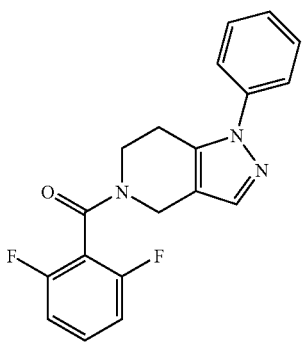

32

To a slurry of 1-phenyl-4,5,6,7-tetrahydro-1H-pyrazolo[4,3-c]pyridine hydrochloride (Step C, 50 mg, 0.18 mmol) in methylene chloride (0.5 mL) were successively added diisopropylethylamine (0.07 mL, 0.41 mmol) and 2,6-difluorobenzoyl chloride. After stirring at rt for 30 min, the mixture was partitioned between methylene chloride (5 mL) and water (1 mL). The organic layer was collected and concentrated in vacuo to afford an oil which was purified by reverse-phase preparative HPLC (YMC S5 20×100 mm, 10 min. run, solvent A: 10% MeOH, 90% H$_2$O, 0.1% TFA; solvent B: 90% MeOH, 10% H$_2$O, 0.1% TFA). Fractions containing the major product were collected and concentrated on a rotary evaporator to remove the methanol followed by lyophilization of the remaining aqueous solution to afford the desired product 32 as a pale yellow semi-solid (33 mg, 53%). HPLC Ret. time=2.83 min (HPLC conditions: Ballistic YMC S5 ODS 4.6×50 mm column with a binary solvent system where solvent A=10% methanol, 90% water, 0.2% phosphoric acid and solvent B=90% methanol, 10% water, and 0.2% phosphoric acid, flow rate=4 mL/min, linear gradient time=4 min, start % B=0, final % B=100), LCMS [M+H]$^+$ 340.1.

Examples 33 to 37

Compounds listed in Table 3 were prepared using methods described in Example 32.

TABLE 3

| Ex. No. | G | HPLC ret. Time, min. (column conditions)* | [M + H]$^+$ |
|---|---|---|---|
| 33 | phenyl | 2.88 | 304.17 |
| 34 | 2-fluorophenyl | 2.89 | 322.13 |
| 35 | 4-fluorophenyl | 2.95 | 322.14 |
| 36 | 2-methylphenyl | 3.02 | 318.17 |

TABLE 3-continued

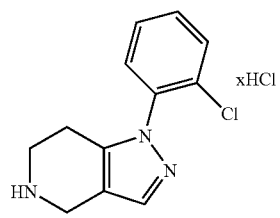

| Ex. No. | G | HPLC ret. Time, min. (column conditions)* | [M + H]+ |
|---|---|---|---|
| 37 | 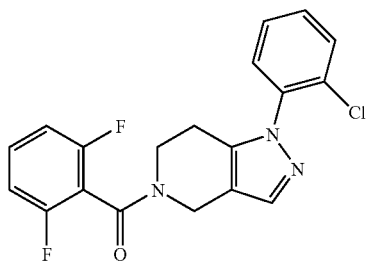 | 2.90 | 343.17 |

*Ballistic YMC S5 ODS 4.6 × 50 mm column with a binary solvent system where solvent A = 10% methanol, 90% water and 0.2% phosphoric acid, and solvent B = 90% methanol, 10% water and 0.2% phosphoric acid, flow rate = 4 mL/min, linear gradient time = 4 min, start % B = 0, final % B = 100.

Example 38

(1-(2-chlorophenyl)-6,7-dihydro-1H-pyrazolo[4,3-c]pyridin-5(4H)-yl)(2,6-difluorophenyl)methanone

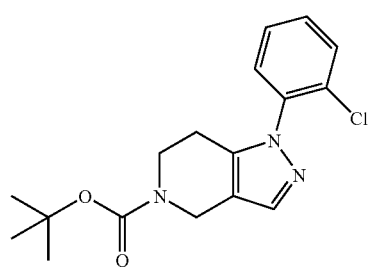

Step A

Tert-butyl 1-(2-chlorophenyl)-6,7-dihydro-1H-pyrazolo[4,3-c]pyridine-5(4H)-carboxylate

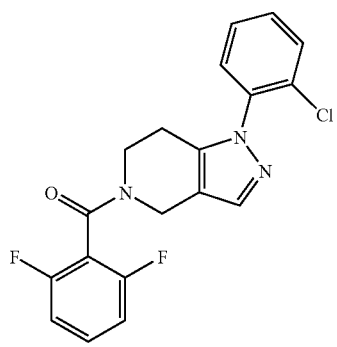

Tert-butyl 3-((dimethylamino)methylene)-4-oxopiperidine-1-carboxylate (Example 32, Step A, 2.0 g) was reacted with 2-chlorophenyl hydrazine hydrochloride as described for Example 32, Step B to yield the title compound a as a yellow oil (1.39 g, 53%). $^1$H NMR (400 MHz, CDCl$_3$): δ 7.56-7.54 (m, 2H), 7.45-7.40 (m, 3H), 4.54 (s, 2H), 3.72 (br s, 2H), 2.58 (br s, 2H), 1.51 (s, 9H).

Step B 1-(2-chlorophenyl)-4,5,6,7-tetrahydro-1H-pyrazolo[4,3-c]pyridine

Tert-butyl 1-(2-chlorophenyl)-6,7-dihydro-1H-pyrazolo[4,3-c]pyridine-5(4H)-carboxylate (Step A, 0.65 g) was prepared as described for Example 32, Step C to yield the title compound b as a pale yellow solid (0.55 g, 92%). $^1$H NMR (400 MHz, d$^3$-MeOD): δ 7.74 (s, 1H), 7.69 (d, J=8.1 Hz, 1H), 7.62-7.50 (m, 3H), 4.38 (s, 2H), 3.58-3.55 (m, 2H), 2.92-2.89 (m, 2H).

Step C (1-(2-chlorophenyl)-6,7-dihydro-1H-pyrazolo[4,3-c]pyridin-5(4H)-yl)(2,6-difluorophenyl)methanone 1-(2-chlorophenyl)-4,5,6,7-tetrahydro-1H-pyrazolo[4,3-c]pyridine (Step B, 50 mg) was reacted with 2,6-difluorobenzoyl chloride as described for Example 32, Step D to afford the crude product, which was purified by reverse-phase preparative (YMC S5 20×100 mm, 10 min. run, solvent A: 10% MeOH, 90% H$_2$O, 0.1% TFA; solvent B: 90% MeOH, 10% H$_2$O, 0.1% TFA). Fractions containing the major product were collected and neutralized by adding satd aq. sodium barcarbonate (~1 mL) and concentrated on a rotary evaporator to remove the methanol. The resulting aqueous slurry was filtered to collect the solid. The solid was washed and rinsed with additional water (~1 mL) and dried under vacuum to afford the title compound 38 as a white solid (35 mg, 54%). HPLC Ret. Time=2.82 min (HPLC conditions: Ballistic YMC S5 ODS 4.6×50 mm column with a binary solvent system where solvent A=10% methanol, 90% water, 0.2% phosphoric acid and solvent B=90% methanol, 10% water, and 0.2% phosphoric acid, flow rate=4 mL/min, linear gradient time=4 min, start % B=0, final % B=100). LCMS [M+H]$^+$ 374.10.

Example 39

(1-(2-chlorophenyl)-6,7-dihydro-1H-pyrazolo[4,3-c]pyridin-5(4H)-yl)(2,6-dichlorophenyl)methanone

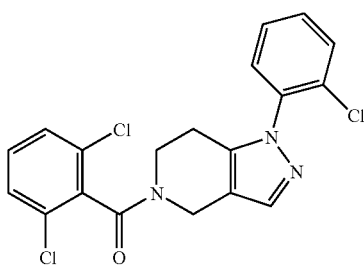

39

1-(2-chlorophenyl)-4,5,6,7-tetrahydro-1H-pyrazolo[4,3-c]pyridine (Example 38, Step B, 50 mg) was reacted with 2,6-difluorobenzoyl chloride as described for Example 38 to afford the title compound 39 as an off-white solid (42 mg, 62%). HPLC Ret. Time=2.99 and 3.07 min (1:1 mixture of apparent atropisomers) (HPLC conditions: Ballistic YMC S5 ODS 4.6×50 mm column with a binary solvent system where solvent A=10% methanol, 90% water, 0.2% phosphoric acid and solvent B=90% methanol, 10% water, and 0.2% phosphoric acid, flow rate=4 mL/min, linear gradient time=4 min, start % B=0, final % B=100). LCMS [M+H]$^+$ 406.02.

Example 40

(1-(2-chlorophenyl)-6,7-dihydro-1H-pyrazolo[4,3-c]pyridin-5(4H)-yl)(1H-indol-5-yl)methanone

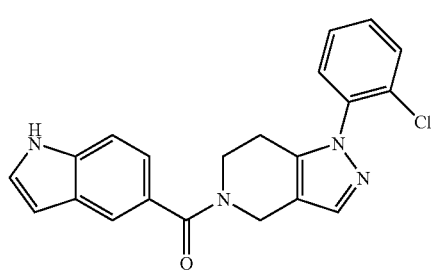

40

1H-indole-5-carboxylic acid (63 mg, 0.39 mmol), EDAC (82 mg, 0.43 mmol) and HOBt (58 mg, 0.43 mmol) were dissolved in DMF (1 mL) and the resulting solution was stirred at rt for 1 h. At this time, 1-(2-chlorophenyl)-4,5,6,7-tetrahydro-1H-pyrazolo[4,3-c]pyridine (Example 38, Step B, 100 mg, 0.33 mmol) and DIPEA (0.18 mL, 1.0 mmol) were successively added and the mixture was heated at 60° C. for 3 h. After cooling to rt, water (~20 mL) was added and the mixture was extracted with ethyl acetate (3×10 mL). The combined extracts were washed with brine and concentrated and the resulting material was purified by flash chromatography on silica gel using 70-80% ethyl acetate in hexanes mixture as the eluant. Fractions containing the major product were combined and concentrated under vacuum to afford the title compound 40 as a white solid (104 mg, 84%). HPLC Ret. Time=2.88 min (HPLC conditions: Ballistic YMC S5 ODS 4.6×50 mm column with a binary solvent system where solvent A=10% methanol, 90% water, 0.2% phosphoric acid and solvent B=90% methanol, 10% water, and 0.2% phosphoric acid, flow rate=4 mL/min, linear gradient time=4 min, start % B=0, final % B=100). LCMS [M+H]$^+$ 377.14.

Examples 41 to 50

Compounds listed in Table 4 were prepared using methods described in Example 40.

TABLE 4

| Ex. No. | G | HPLC ret. Time, min. (column conditions)* | [M + H]$^+$ |
|---|---|---|---|
| 41 | 1H-indol-2-yl | 3.27 | 377.12 |
| 42 | 1H-indol-4-yl | 2.80 | 377.12 |
| 43 | 1H-indol-6-yl | 3.07 | 377.12 |
| 44 | 1H-indol-3-yl | 3.01 | 377.12 |

TABLE 4-continued

| Ex. No. | G | HPLC ret. Time, min. (column conditions)* | [M + H]+ |
|---|---|---|---|
| 45 | (1H-indazol-3-yl) | 2.98 | 378.11 |
| 46 | (1H-benzimidazol-2-yl) | 3.06 | 378.11 |
| 47 | (1H-benzimidazol-5-yl) | 1.83 | 378.10 |
| 48 | (2-methyl-1H-indol-3-yl) | 3.08 | 391.05 |
| 49 | (1-methyl-1H-indol-3-yl) | 3.16 | 391.06 |
| 50 | (1H-indol-7-yl) | 3.20 | 377.06 |

*Ballistic YMC S5 ODS 4.6 × 50 mm column with a binary solvent system where solvent A = 10% methanol, 90% water, 0.2% phosphoric acid and solvent B = 90% methanol, 10% water, and 0.2% phosphoric acid, flow rate = 4 mL/min, linear gradient time = 4 min, start % B = 0, final % B = 100.

Example 51

2-(5-(1-(2-chlorophenyl)-4,5,6,7-tetrahydro-1H-pyrazolo[4,3-c]pyridine-5-carbonyl)-1H-indol-3-yl)-N,N-dimethyl-2-oxoacetamide

51

To a solution of (1-(2-chlorophenyl)-6,7-dihydro-1H-pyrazolo[4,3-c]pyridin-5(4H)-yl)(1H-indol-5-yl)methanone (Example 40, 83 mg, 0.22 mmol) in methylene chloride (2 mL) at 0° C. was added a 2 M solution of oxalyl chloride (0.13 mL, 0.26 mmol) and the resulting mixture stirred at 0° C. for 15 min, then allowed to warm to rt and stirred for an additional 1.5 h. The mixture was concentrated and the resulting residue was slurried in methylene chloride (1 mL) and a 2 M solution of dimethylamine in THF (0.3 mL) was added. After stirring at rt for 15 min, the clear solution was concentrated and the residue was purified by reverse phase preparative HPLC (HPLC conditions: YMC S5 20×100 mm, 10 min. run, solvent A: 10% MeOH, 90% H$_2$O, 0.1% TFA; solvent B: 90% MeOH, 10% H$_2$O, 0.1% TFA). Fractions containing the desired product were collected and concentrated to remove the methanol, and satd. aq. sodium bicarbonate (~1 mL) was added. The mixture was extracted with ethyl acetate (3×5 mL) and the combined extracts were washed with brine, dried over anhyd. sodium sulfate and concentrated to afford the title compound 51 as a tan colored solid (33 mg, 31%). HPLC Ret. Time=2.55 min (HPLC conditions: Ballistic YMC S5 ODS 4.6×50 mm column with a binary solvent system where solvent A=10% methanol, 90% water, 0.2% phosphoric acid and solvent B=90% methanol, 10% water, and 0.2% phosphoric acid, flow rate=4 mL/min, linear gradient time=4 min, start % B=0, final % B=100). LCMS [M+H]+ 476.14.

Examples 52-53

(1-(2-chlorophenyl)-6,7-dihydro-1H-pyrazolo[4,3-c]pyridin-5(4H)-yl)(2,3,4,9-tetrahydro-1H-pyrido[3,4-b]indol-6-yl)methanone

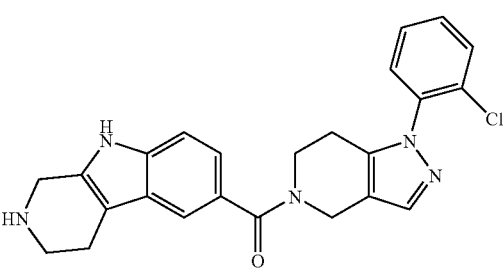

52

Step A

Example 53

Tert-butyl 6-(1-(2-chlorophenyl)-4,5,6,7-tetrahydro-1H-pyrazolo[4,3-c]pyridine-5-carbonyl)-3,4-dihydro-1H-pyrido[3,4-b]indole-2(9H)-carboxylate

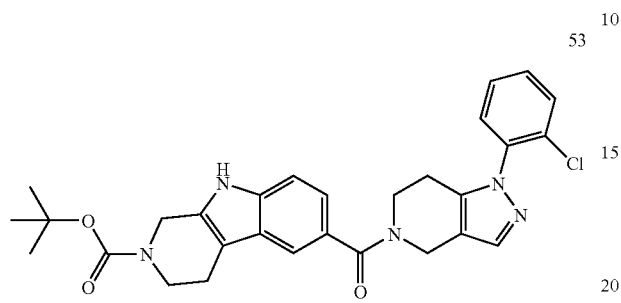

53

2-(tert-butoxycarbonyl)-2,3,4,9-tetrahydro-1H-pyrido[3,4-b]indole-6-carboxylic acid (WO 2000/059904, 60 mg, 0.19 mmol) was coupled to 1-(2-chlorophenyl)-4,5,6,7-tetrahydro-1H-pyrazolo[4,3-c]pyridine (Example 38, Step B, 53 mg, 0.17 mmol) as described for Example 40 to afford the title compound 53 as a light tan colored solid (95 mg, 94%). LCMS [M+H]$^+$ 532.18.

Step B (1-(2-chlorophenyl)-6,7-dihydro-1H-pyrazolo[4,3-c]pyridin-5(4H)-yl)(2,3,4,9-tetrahydro-1H-pyrido[3,4-b]indol-6-yl)methanone

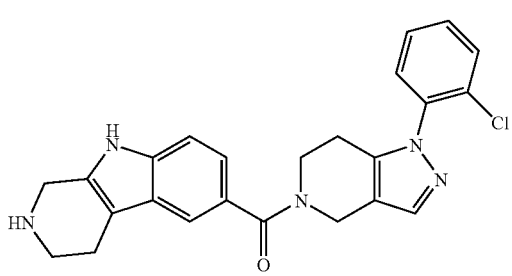

52

To a solution of tert-butyl 6-(1-(2-chlorophenyl)-4,5,6,7-tetrahydro-1H-pyrazolo[4,3-c]pyridine-5-carbonyl)-3,4-dihydro-1H-pyrido[3,4-b]indole-2(9H)-carboxylate (Step A, 95 mg, 0.18 mmol) in dioxane (1 mL) was added a 4 N solution of anhyd. HCl in dioxane (0.5 mL). After stirring at rt for 30 min, hexane (1 mL) was added and the precipitated solid was collected by vacuum filtration. The resulting hygroscopic solid was purified by reverse phase preparative HPLC (HPLC conditions: YMC S5 20×100 mm, 10 min. run, solvent A: 10% MeOH, 90% H$_2$O, 0.1% TFA; solvent B: 90% MeOH, 10% H$_2$O, 0.1% TFA). Fractions containing the desired product were collected and concentrated to remove the methanol and the remaining aqueous portion was neutralized by the addition of satd. aq. sodium bicarbonate. The resulting solid was collected by vacuum filtration and dried under vacuum to afford the title compound 52 as a cream colored solid (41 mg, 53%).

HPLC Ret. Time=2.08 min (HPLC conditions: Ballistic YMC S5 ODS 4.6×50 mm column with a binary solvent system where solvent A=10% methanol, 90% water, 0.2% phosphoric acid and solvent B=90% methanol, 10% water, and 0.2% phosphoric acid, flow rate=4 mL/min, linear gradient time=4 min, start % B=0, final % B=100). LCMS [M+H]$^+$ 432.13.

Example 54

(6-chloro-1-methyl-1H-indol-5-yl)(1-(2-chlorophenyl)-6,7-dihydro-1H-pyrazolo[4,3-c]pyridin-5(4H)-yl)methanone

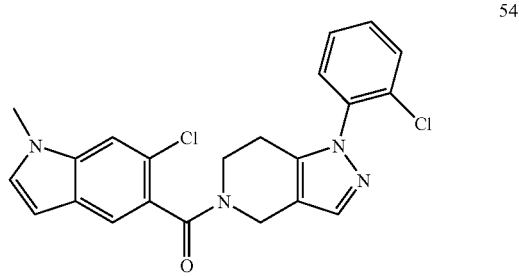

54

6-chloro-1-methyl-1H-indole-5-carboxylic acid (WO 04/022712) was coupled to 1-(2-chlorophenyl)-4,5,6,7-tetrahydro-1H-pyrazolo[4,3-c]pyridine (Example 38, Step B) as described in Example 40 to afford the title compound 54 as clear oil (2 mg). HPLC Ret. Time=3.24 min. (HPLC conditions: YMC S5 Combiscreen ODS; 4.6×50 mm (4 min. gradient); Solvent A=10% MeOH, 90% H$_2$O, 0.2% H$_3$PO$_4$; solvent B=90% MeOH, 10% H$_2$O, 0.2% H$_3$PO$_4$). LCMS [M+H]$^+$ 425.03.

Example 55

2-(6-chloro-5-(1-(2-chlorophenyl)-4,5,6,7-tetrahydro-1H-pyrazolo[4,3-c]pyridine-5-carbonyl)-1-methyl-1H-indol-3-yl)-N,N-dimethyl-2-oxoacetamide

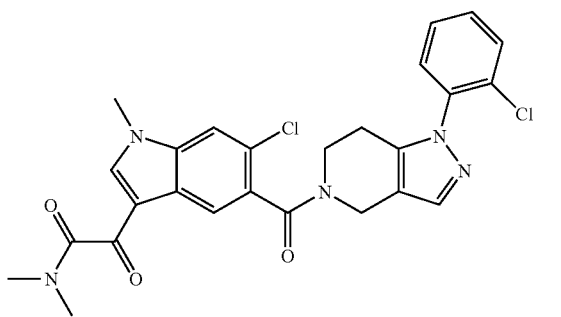

55

The title compound 55 was prepared from (6-chloro-1-methyl-1H-indol-5-yl)(1-(2-chlorophenyl)-6,7-dihydro-1H-pyrazolo[4,3-c]pyridin-5(4H)-yl)methanone (Example 54) as described in Example 51 to afford the title compound 55 as a white solid (2 mg). HPLC Ret. Time=2.80 min. (HPLC conditions: YMC S5 Combiscreen ODS; 4.6×50 mm (4 min.

gradient); Solvent A=10% MeOH, 90% H₂O, 0.2% H₃PO₄; solvent B=90% MeOH, 10% H₂O, 0.2% H₃PO₄). LCMS [M+H]⁺ 524.08.

Example 56

(1-(2-chlorophenyl)-6,7-dihydro-1H-pyrazolo[4,3-c]pyridin-5(4H)-yl)(6-methoxy-1H-pyrrolo[2,3-b]pyridin-5-yl)methanone

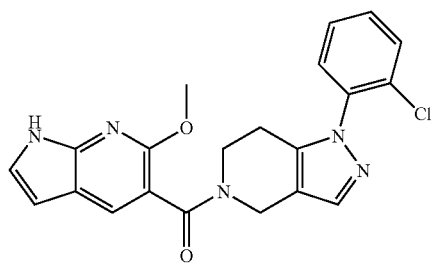

6-methoxy-1H-pyrrolo[2,3-b]pyridine-5-carboxylic acid (PCT Publication Number WO 04/032874) was coupled to 1-(2-chlorophenyl)-4,5,6,7-tetrahydro-1H-pyrazolo[4,3-c]pyridine (Example 38, Step B) as described in Example 40 to afford the title compound 56 as a white solid. HPLC Ret. Time=2.80 min (HPLC conditions: Ballistic YMC S5 ODS 4.6×50 mm column with a binary solvent system where solvent A=10% methanol, 90% water, 0.2% phosphoric acid and solvent B=90% methanol, 10% water, and 0.2% phosphoric acid, flow rate=4 mL/min, linear gradient time=4 min, start % B=0, final % B=100). LCMS [M+H]⁺ 408.15.

Example 57

2-(5-(1-(2-chlorophenyl)-4,5,6,7-tetrahydro-1H-pyrazolo[4,3-c]pyridine-5-carbonyl)-6-methoxy-1H-pyrrolo[2,3-b]pyridin-3-yl)-N,N-dimethyl-2-oxoacetamide

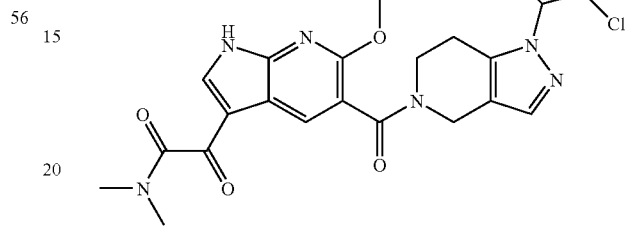

The title compound 57 was prepared from (1-(2-chlorophenyl)-6,7-dihydro-1H-pyrazolo[4,3-c]pyridin-5(4H)-yl)(6-methoxy-1H-pyrrolo[2,3-b]pyridin-5-yl)methanone (Example 56, 30 mg) as described in Example 51 to afford the title compound 57 as a white solid (13.8 mg, 37%). HPLC Ret. Time=2.60 min (HPLC conditions: Ballistic YMC S5 ODS 4.6×50 mm column with a binary solvent system where solvent A=10% methanol, 90% water, 0.2% phosphoric acid and solvent B=90% methanol, 10% water, and 0.2% phosphoric acid, flow rate=4 mL/min, linear gradient time=4 min, start % B=0, final % B=100). LCMS [M+H]⁺ 507.30.

Examples 58 to 60

Compounds listed in Table 5 were prepared as in Example 57 using the methods described in Example 57.

TABLE 5

| Ex. No. | G | HPLC ret. Time, min. (column conditions)* | [M + H]⁺ |
|---|---|---|---|
| 58 | (pyrrolidine-N-C(O)-C(O)- attached to 6-methoxy-1H-pyrrolo[2,3-b]pyridin-3-yl) | 2.82 | 533.32 |

TABLE 5-continued

| Ex. No. | G | HPLC ret. Time, min. (column conditions)* | [M + H]+ |
|---|---|---|---|
| 59 | | 2.61 | 479.28 |
| 60 | | 2.53 | 549.35 |

*Ballistic YMC S5 ODS 4.6 × 50 mm column with a binary solvent system where solvent A = 10% methanol, 90% water, 0.2% phosphoric acid and solvent B = 90% methanol, 10% water, and 0.2% phosphoric acid, flow rate = 4 mL/min, linear gradient time = 4 min, start % B = 0, final % B = 100.

Example 61

(1-(2-chlorophenyl)-6,7-dihydro-1H-pyrazolo[4,3-c]pyridin-5(4H)-yl)(1-(2-(diethylamino)ethyl)-1H-indol-5-yl)methanone

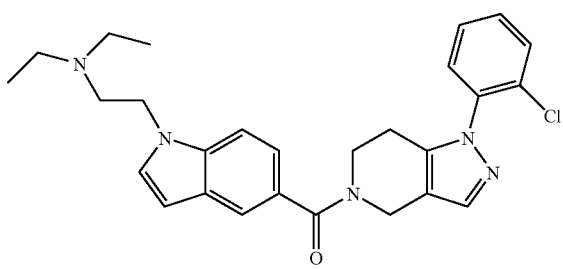

To a solution of (1-(2-chlorophenyl)-6,7-dihydro-1H-pyazolo[4,3-c]pyridin-5(4H)-yl)(1H-indol-5-yl)methanone (Example 40, 40 mg, 0.11 mmol) in DMF (0.3 mL) at rt was added sodium hydride (60% dispersion, 25 mg, 0.64 mmol) and the resulting mixture was stirred at rt for 15 min., then 2-chloro-N, N-dimethylethylamine hydrochloride (36 mg, 0.21 mmol) was added and the mixture was stirred at rt for 16 h. The resulting reaction mixture was directly subjected to purification by reverse phase preparative HPLC (HPLC conditions: YMC S5 20×100 mm, 10 min. run, solvent A: 10% MeOH, 90% H$_2$O, 0.1% TFA; solvent B: 90% MeOH, 10% H$_2$O, 0.1% TFA). Fractions containing the desired product were collected and concentrated to remove the methanol and the remaining aqueous portion was lyophilized to afford the trifluoroacetic acid salt of the title compound 61 as an off-white solid (40 mg, 64%). HPLC Ret. Time=2.23 min (HPLC conditions: Ballistic YMC S5 ODS 4.6×50 mm column with a binary solvent system where solvent A=10% methanol, 90% water, 0.2% phosphoric acid and solvent B=90% methanol, 10% water, and 0.2% phosphoric acid, flow rate=4 mL/min, linear gradient time=4 min, start % B=0, final % B=100). LCMS [M+H]+ 476.24.

Examples 62 to 66

Compounds listed in Table 6 were prepared using the methods described in Example 61.

TABLE 6

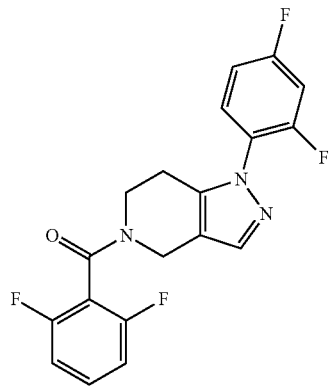

| Ex. No. | G | HPLC ret. Time, min. (column conditions)* | [M + H]+ |
|---|---|---|---|
| 62 | H₃C— | 3.07 | 391.13 |
| 63 | isopropyl | 3.41 | 419.12 |
| 64 | -CH₂CH₂CH₂N(CH₃)₂ | 2.16 | 448.19 |
| 65 | -CH₂CH₂CH₂-morpholino | 2.19 | 490.20 |
| 66 | -CH₂CH₂CH₂CH₂N(CH₃)₂ | 2.28 | 462.24 |

*Ballistic YMC S5 ODS 4.6 × 50 mm column with a binary solvent system where solvent A = 10% methanol, 90% water, 0.2% phosphoric acid and solvent B = 90% methanol, 10% water, and 0.2% phosphoric acid, flow rate = 4 mL/min, linear gradient time = 4 min, start % B = 0, final % B = 100.

Example 67

2,6-difluorophenyl(1-(2,4-difluorophenyl)-6,7-dihydro-1H-pyrazolo[4,3-c]pyridin-5(4H)-yl)methanone

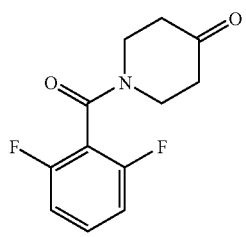

67

Step A 1-(2,6-difluorobenzoyl)piperidin-4-one

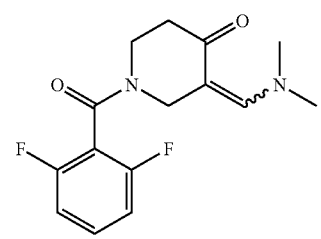

a

To a solution of 4-piperidone monohydrate hydrochloride (1.0 g, 6.5 mmol) in methylene chloride (32 mL) at rt were successively added DIPEA (1.4 mL, 7.8 mmol) and 2,6-difluorobenzoyl chloride (0.82 mL, 6.5 mmol). The resulting heterogeneous mixture was stirred at rt for 2 d. The resulting mixture was washed with 1 N aq. sodium hydroxide (3×10 mL) and the combined basic aqueous portion was back-extracted with methylene chloride (2×10 mL). The organic extracts were combined and washed with 10% aq. citric acid (2×10 mL), brine (20 mL), and dried over anhyd sodium sulfate. Concentration under vacuum afforded the title compound a as a pale yellow solid (1.29 g, 83%). $^1$H NMR (400 MHz, d$^3$-MeOD): δ 7.60 (m, 1H), 7.18-7.09 (m, 2H), 4.09 (t, J=6.4 Hz, 2H), 3.70 (t, J=6.3 Hz, 2H), 2.62 (t, J=6.4 Hz, 2H), 2.48 (t, J=6.3 Hz, 2H).

Step B 1-(2,6-difluorobenzoyl)-3-((dimethylamino)methylene)piperidin-4-one b A mixture of 1-(2,6-difluorobenzoyl)piperidin-4-one (Step A, 0.94 g, 3.9 mmol) and tert-butoxy bis(dimethylamino) methane (0.86 mL, 3.9 mmol) was heated at 110° C. for 3 h then cooled to rt. Purification of the resulting mixture by flash chromatography on silica gel initially eluting with 100% ethyl acetate then finally eluting with 5% methanol in ethyl acetate afforded fractions containing the desired product. Concentration of these fractions afforded the title compound b as a pale yellow solid (1.09 g, 60%). LCMS [M+H]+ 295.1.

Step C 2,6-difluorophenyl(1-(2,4-difluorophenyl)-6,7-dihydro-1H-pyrazolo[4,3-c]pyridin-5(4H)-yl)methanone

67

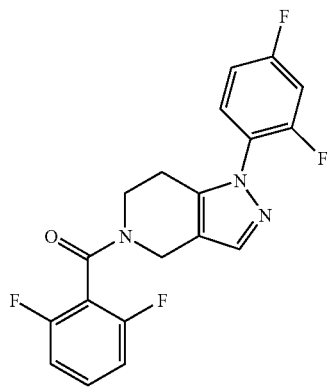

To 1-(2,6-difluorobenzoyl)-3-((dimethylamino)methylene)piperidin-4-one (Step B, 0.10 g, 0.34 mmol) was reacted with 2,4-difluorophenyl hydrazine hydrochloride as described in Example 32, Step B, to yield the title compound 67 as a white solid (36 mg, 28%). HPLC Ret. time=2.81 min (HPLC conditions: Ballistic YMC S5 ODS 4.6×50 mm column with a binary solvent system where solvent A=10% methanol, 90% water, 0.2% phosphoric acid and solvent B=90% methanol, 10% water, and 0.2% phosphoric acid, flow rate=4 mL/min, linear gradient time=4 min, start % B=0, final % B=100). LCMS [M+H]+ 376.18.

Examples 68 to 73

Compounds listed in Table 7 were prepared using methods described in Example 67.

TABLE 7

| Ex. No. | G | HPLC ret. Time, min. (column conditions)* | [M + H]+ |
|---|---|---|---|
| 68 | 3-chloro-4-fluorophenyl | 2.92 | 392.09 |
| 69 | 2-fluorophenyl | 2.74 | 358.13 |
| 70 | 3-chlorophenyl | 3.19 | 374.12 |
| 71 | 2,5-difluorophenyl | 2.81 | 376.14 |
| 72 | 2-methylphenyl | 2.88 | 354.15 |
| 73 | 3-trifluoromethylphenyl | 3.28 | 408.11 |

*Ballistic YMC S5 ODS 4.6 × 50 mm column with a binary solvent system where solvent A = 10% methanol, 90% water, 0.2% phosphoric acid and solvent B = 90% methanol, 10% water, and 0.2% phosphoric acid, flow rate = 4 mL/min, linear gradient time = 4 min, start % B = 0, final % B = 100

Examples 74-76

1-(2-chloro-4-fluorophenyl)-5-(1H-indole-3-carbonyl)-4,5,6,7-tetrahydro-1H-pyrazolo[4,3-c]pyridine-3-carboxamide

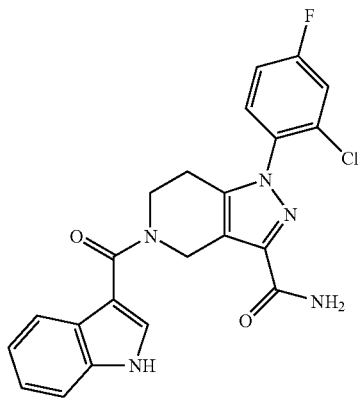

74

Step A

Tert-butyl 4-morpholino-5,6-dihydropyridine-1(2H)-carboxylate

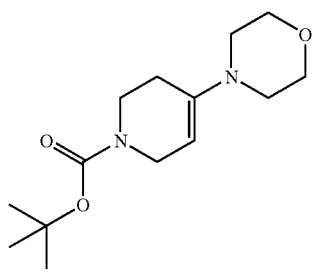

a

To a solution of tert-butyl-4-oxo-1-piperidine carboxylate (8.0 g, 40 mmol) and morpholine (3.6 g, 42 mmol) in benzene (16 mL) was added p-toluenesulfonic acid (40 mg) and the resulting solution was refluxed using a Dean-Stark trap for 24 h. After cooling to rt, the solution was concentrated under vacuum to afford the title compound a as a thick reddish-orange oil which was used without any further purification (11.1 g, ~quant). $^1$H NMR (400 MHz, CDCl$_3$): δ 7.36 (s, 1H), 3.94 (br s, 2H), 3.74 (m, 4H), 3.54 (m, 2H), 2.80 (m, 4H), 2.16 (br s, 2H), 1.47 (s, 9H).

Step B

Ethyl 2-chloro-2-(2-(2-chloro-4-fluorophenyl)hydrazono)acetate

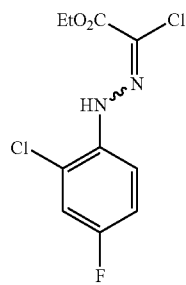

b

To a slurry of 2-chloro-4-fluoroaniline (5.0 g, 34.3 mmol) in water (20 mL) was added conc. HCl (9.5 mL) and the slurry was cooled in an ice bath. To this mixture was then added dropwise a mixture of sodium nitrite (2.43 g, 35.3 mmol) in water (20 mL) over ~20 min and the mixture was stirred at 0° C. for an additional 1 h. The resulting solution was then added to a mixture of ethyl-2-chloroacetoacetate (4.6 mL, 33.3 mmol) and sodium acetate (6.28 g, 76.6 mmol) in acetone (50 mL) at rt followed by stirring at rt for 16 h. The resulting heterogeneous mixture was briefly sonicated to give a uniform suspension and the mixture was diluted with water (150 mL) and stirred vigorously for 1 h. The solid was collected by vacuum filtration, rinsed with additional water (3×100 mL portions) and dried under vacuum to afford the title compound b as a yellow solid (8.7 g, 94%). $^1$H NMR (400 MHz, CDCl$_3$): δ 8.69 (s, 1H), 7.61-7.58 (m, 1H), 7.13-7.11 (m, 1H), 7.05-7.00 (m, 1H), 4.40 (q, J=7.1 Hz, 2H), 1.41 (t, J=7.1 Hz, 3H).

Step C 5-tert-butyl 3-ethyl 1-(2-chloro-4-fluorophenyl)-6,7-dihydro-1H-pyrazolo[4,3-c]pyridine-3,5(4H)-dicarboxylate

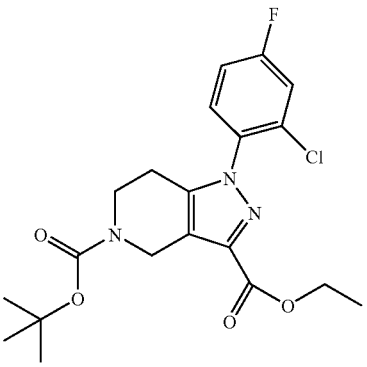

c

To a solution of tert-butyl 4-morpholino-5,6-dihydropyridine-1(2H)-carboxylate (Step A, 9.3 g, 31.3 mmol) in ethyl acetate (70 mL) at rt were successively added triethylamine (8.7 mL) and ethyl 2-chloro-2-(2-(2-chloro-4-fluorophenyl)-hydrazono)acetate (Step B, 8.7 g, 31.3 mmol) and the resulting solution was stirred at rt for 16 h. The mixture was filtered to remove the solids and the resulting clear filtrate was washed with water (3×60 mL), and brine (50 mL), then dried over anhyd.sodium sulfate. Concentration under vacuum afforded a dark red oil which was redissolved in diethyl ether and reconcentrated under vacuum to initially afford an oil which solidified upon drying under vacuum to provide 16.5 g of an orange solid. This material was dissolved in ethanol (100 mL), and 20% aq HCl (10 mL) was added followed by stirring at rt for 1 h. Saturated aq. sodium bicarbonate was then slowly added and the mixture was stirred vigorously for 2 h. The precipitated solid was collected by vacuum filtration,

Step D

Ethyl 1-(2-chloro-4-fluorophenyl)-4,5,6,7-tetrahydro-1H-pyrazolo[4,3-c]pyridine-3-carboxylate hydrochloride

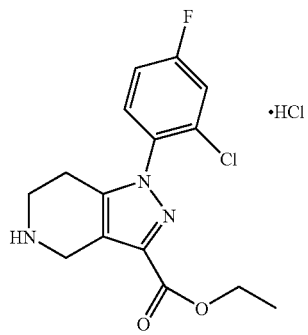

d

To a solution of 5-tert-butyl 3-ethyl 1-(2-chloro-4-fluorophenyl)-6,7-dihydro-1H-pyrazolo[4,3-c]pyridine-3,5(4H)-dicarboxylate (Step C, 10.68 g, 25.2 mmol) in anhyd. dioxane (110 mL) at rt was added 4 N anhyd.HCl in dioxane (20 mL) and the resulting mixture was stirred at 50° C. for 3 h. At this time, hexane (125 mL) was slowly added and the precipitated solid was collected by vacuum filtration and dried under vacuum to provide the title compound d as a light tan-colored solid (8.23 g, 91%). LCMS [M+H]+ 324.06.

Step E

Example 75

Ethyl 1-(2-chloro-4-fluorophenyl)-5-(1H-indole-3-carbonyl)-4,5,6,7-tetrahydro-1H-pyrazolo[4,3-c]pyridine-3-carboxylate

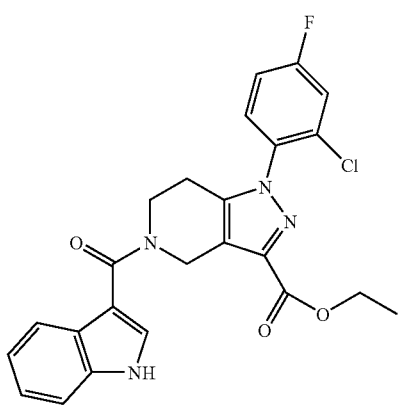

75

A mixture of 1H-indole-3-carboxylic acid (0.99 g, 6.13 mmol), EDAC (1.28 g, 6.68 mmol) and HOBt (0.83 g, 6.13 mmol) in DMF (6 mL) was stirred at rt for 2.5 h and the resulting slurry was transferred into a slurry of ethyl 1-(2-chloro-4-fluorophenyl)-4,5,6,7-tetrahydro-1H-pyrazolo[4,3-c]pyridine-3-carboxylate hydrochloride (Step D, 2.0 g, 5.57 mmol) and DIPEA (2.3 mL) in DMF (6 mL) at rt. After stirring for 1 h, the resulting mixture was slowly added with stirring to a mixture of satd. aq sodium bicarbonate (~25 mL) and water (100 mL). The solid was collected by vacuum filtration and partially air-dried in the funnel. The solid was then dissolved in ethyl acetate (~150 mL), washed with brine, dried over anhyd sodium sulfate, filtered and concentrated under vacuum to afford the title compound 75 as an off-white solid (2.53 g, 98%).

Step F

Example 76

1-(2-chloro-4-fluorophenyl)-5-(1H-indole-3-carbonyl)-4,5,6,7-tetrahydro-1H-pyrazolo[4,3-c]pyridine-3-carboxylic acid

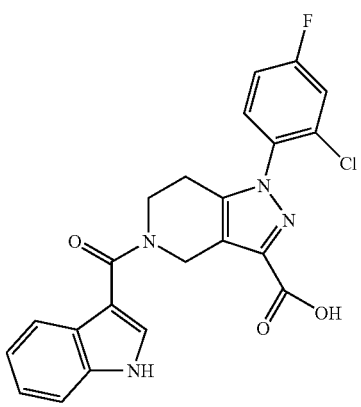

76

To a slurry of ethyl 1-(2-chloro-4-fluorophenyl)-5-(1H-indole-3-carbonyl)-4,5,6,7-tetrahydro-1H-pyrazolo[4,3-c]pyridine-3-carboxylate (Step E, 2.45 g, 5.3 mmol) in methanol (30 mL) at rt was added 3 N aq sodium hydroxide (6 mL) and the resulting slurry was heated to 55° C. and stirred for 1.5 h. The clear solution was concentrated under vacuum to remove the methanol and the resulting solids were dissolved in water (100 mL) and the aqueous solution was made acidic to pH ~1 by slowly adding 1 N aq HCl. The precipitated solid was collected by vacuum filtration and dried overnight to afford the title compound 76 as an off-white solid (2.23 g, 97%). LCMS [M+H]+ 439.53.

Step G 1-(2-chloro-4-fluorophenyl)-5-(1H-indole-3-carbonyl)-4,5,6,7-tetrahydro-1H-pyrazolo[4,3-c]pyridine-3-carboxamide A mixture of 1-(2-chloro-4-fluorophenyl)-5-(1H-indole-3-carbonyl)-4,5,6,7-tetrahydro-1H-pyrazolo[4,3-c]pyridine-3-carboxylic acid (Step F, 40 mg, 0.09 mmol), EDAC (21 mg, 0.11 mmol) and HOBt (14 mg, 0.10 mmol) in DMF (0.25 mL) was stirred at rt for 2.5 h. To this mixture was then added ammonia as a 20% solution in methanol (0.030 mL) followed by stirring at rt for 16 h. Water was added (~4 mL) followed by the addition of saturated aq. sodium bicarbonate (~1 mL), and the precipitated solid was collected by vacuum filtration and rinsed with water (~5 mL) and dried to afford the title compound 74 as an off-white solid (35 mg, 87%) LCMS [M+H]+ 438.18.

Examples 77 to 86

Compounds listed in Table 8 were prepared using methods described in Example 74.

TABLE 8

| Ex. No. | G | HPLC ret. Time, min. (column conditions)* | [M + H]+ |
|---|---|---|---|
| 77 | -NH-CH₃ | 3.13 | 452.22 |
| 78 | -N(CH₃)₂ | 3.36 | 466.24 |
| 79 | -NH-iPr | 3.63 | 480.26 |
| 80 | -NH-CH₂CH₂-N(CH₃)₂ | 2.64 | 509.23 |
| 81 | -NH-CH₂CH₂CH₂-N(CH₃)₂ | 2.72 | 523.26 |
| 82 | morpholino | 3.37 | 508.21 |
| 83 | -NH-CH₂CH₂-OH | 3.20 | 482.23 |
| 84 | 4-methylpiperazin-1-yl | 2.72 | 535.56 |
| 85 | -N(CH₂CH₂OH)₂ | 3.06 | 512.47 |
| 86 | -NH-CH(CH₂OH)- (chiral) | 3.31 | 496.51 |

*Ballistic YMC S5 ODS 4.6 × 50 mm column with a binary solvent system where solvent A = 10% methanol, 90% water, 0.2% phosphoric acid and solvent B = 90% methanol, 10% water, and 0.2% phosphoric acid, flow rate = 4 mL/min, linear gradient time = 4 min, start % B = 0, final % B = 100.

Example 87

1-(2-chloro-4-fluorophenyl)-5-(1H-indole-3-carbonyl)-N-(piperidin-4-yl)-4,5,6,7-tetrahydro-1H-pyrazolo[4,3-c]pyridine-3-carboxamide 1-(2-chloro-4-fluorophenyl)-5-(1H-indole-3-carbonyl)-4,5,6,7-tetrahydro-1H-pyrazolo[4,3-c]pyridine-3-carboxylic acid (Example 76, 40 mg) was coupled to tert-butyl 4-aminopiperidine-1-carboxylate using the method described in Example 74, Step G, to afford the Boc-protected intermediate as a white solid which was then dissolved in dioxane (1 mL), and 4 N anhyd.HCl in dioxane (1 mL) was added. After stirring at rt for 3 h, the solvent was removed under vacuum and the residue was purified by reverse phase preparative HPLC (HPLC conditions: YMC S5 20×100 mm, 10 min. run, solvent A: 10% MeOH, 90% H₂O, 0.1% TFA; solvent B: 90% MeOH, 10% H₂O, 0.1% TFA). Fractions containing the desired product were collected and concentrated to remove the methanol and the remaining aqueous portion was neutralized by the addition of satd. aq. sodium bicarbonate. The resulting solid was collected by vacuum filtration and dried under vacuum to afford the title compound 87 as a white solid (46 mg, 99%). HPLC Ret. Time=2.72 min (HPLC conditions: Ballistic YMC S5 ODS 4.6×50 mm column with a binary solvent system where solvent A=10% methanol, 90% water, 0.2% phosphoric acid and solvent B=90% methanol, 10% water, and 0.2% phosphoric acid, flow rate=4 mL/min, linear gradient time=4 min, start % B=0, final % B=100). LCMS [M+H]⁺ 521.63.

Example 88

(4-(2,4-difluorophenyl)-5,6-dihydropyrido[3,4-d]pyrimidin-7(8H)-yl)(2-methoxyphenyl)methanone

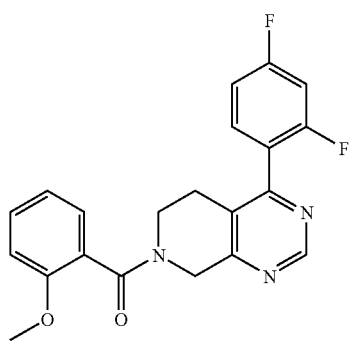

88

Step A 7-benzyl-5,6,7,8-tetrahydropyrido[3,4-d]pyrimidin-4(3H)-one

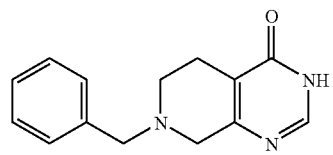

a

To a solution of sodium methoxide (1.67 g, 30.9 mmol) in anhydrous MeOH (10 mL) at room temperature was added formamidine acetate (1.15 g, 11 mmol) in one portion as solid followed by ethyl-1-benzyl-3-oxo-4-piperidine carboxylate hydrochloride (2.63 g, 8.83 mmol) in one portion. The reaction mixture was stirred at rt for 20 h. The reaction was cooled at 0° C., and water (6 mL) was added followed by acetic acid (0.63 mL, 11 mmol) and the mixture was stirred at rt for 1 h. The mixture was concentrated under vacuum to remove the methanol and then stirred at rt overnight. The resulting solid was collected by filtration and washed with water (5 mL×3) and dried on filter to afford the title compound a (1.50 g, 70%) as an orange solid. LCMS [M+H]⁺ 242.16.

Step B 7-benzyl-4-chloro-5,6,7,8-tetrahydropyrido[3,4-d]pyrimidine

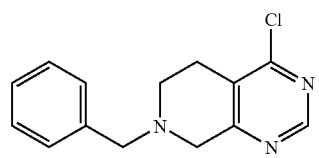

b

To 7-benzyl-5,6,7,8-tetrahydropyrido[3,4-d]pyrimidin-4(3H)-one (Step A, 1.50 g, 6.22 mmol) in toluene (25 mL) were sequentially added DIPEA (0.87 mL, 5.0 mmol) and POCl₃ (0.70 mL, 7.46 mmol). The contents were heated at 105° C. for 2 hour, cooled to rt, diluted with dichloromethane (100 mL) and stirred with cold aq. sat'd NaHCO₃ (150 mL) for 1 h. The dichloromethane layer was dried over sodium sulfate and concentrated under reduced pressure to afford the title compound b (1.61 g) as a dark oil. LCMS [M+H]⁺ 260.08.

Step C 7-benzyl-4-(2,4-difluorophenyl)-5,6,7,8-tetrahydro-pyrido[3,4-d]pyrimidine

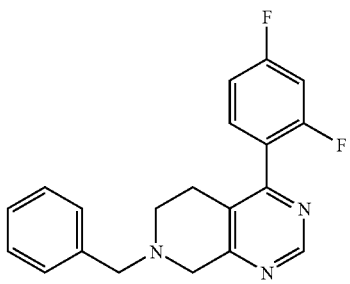

c

To 7-benzyl-4-chloro-5,6,7,8-tetrahydropyrido[3,4-d]pyrimidine (Step B, 1.61 g, 6.22 mmol) in toluene (25 mL) were sequentially added 2,4-difluorophenylboronic acid (1.18 g, 7.46 mmol), 2M aq potassium carbonate (6.2 mL, 12.4 mmol), ethanol (3.1 mL) and tetrakis(triphenylphosphine) palladium (0.36 g, 0.31 mmol) under an argon atmosphere. The contents were heated at 110° C. for 10 hour, cooled to room temperature, concentrated under reduced pressure and partitioned between ethyl acetate (2×150 mL) and water (50 mL). The ethyl acetate layer was extracted with aq. HCl (1N, 100 mL×3) and the aqueous portion was cooled with ice bath and neutralized with aq. NaOH (10N) to pH ~12, saturated with NaCl and extracted with dichloromethane (4×100 mL). The dichloromethane layer was dried over sodium sulfate and concentrated under reduced pressure to afford the title compound c (0.81 g, 38% two steps) as a dark oil. LCMS [M+H]⁺ 338.11.

Step D 4-(2,4-difluorophenyl)-5,6,7,8-tetrahydropyrido[3,4-d]pyrimidine hydrochloride

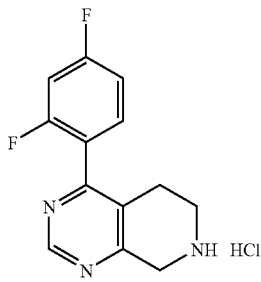

d

To 7-benzyl-4-(2,4-difluorophenyl)-5,6,7,8-tetrahydropyrido[3,4-d]pyrimidine (Step C, 0.81 g, 2.4 mmol) in dichloromethane (10 mL) at 0° C. was added DIPEA (0.75 mL, 4.3 mmol) and 1-chloroethylchloroformate (0.34 mL, 3.1 mmol). The contents were stirred at 0° C. for 1 hour and at room temperature for 20 hours. The reaction was stirred with cold aq. sat'd NaHCO³ (50 mL) for 1 hour and extracted with dichloromethane (2×100 mL). The dichloromethane layer was dried over sodium sulfate and concentrated under reduced pressure dryness. The resulting intermediate was dissolved in methanol (9 mL) and heated at reflux for 1 hour and concentrated under reduced pressure to give dark oil, which was triturated with hot ethyl acetate and recrystallized from dichloromethane and ethyl acetate to give the title compound d as a dark solid.

Step E (4-(2,4-difluorophenyl)-5,6-dihydropyrido[3,4-d]pyrimidin-7(8H)-yl)(2-methoxyphenyl)methanone To a solution of 4-(2,4-difluorophenyl)-5,6,7,8-tetrahydropyrido[3,4-d]pyrimidine hydrochloride (Step D, 20 mg, 0.07 mmol) in anhydrous dichloromethane (0.3 mL) and diisopropylethylamine (37 μL, 0.21 mmol) were added 2-methoxybenzoyl chloride, and the contents were stirred at rt for 15 minutes. The reaction mixture was concentrated to remove the solvent and the residue was subjected to reverse phase preparative HPLC (YMC S5 20×100 mm, 10 min. run, solvent A: 10% MeOH, 90% H₂O, 0.1% TFA; solvent B: 90% MeOH, 10% H₂O, 0.1% TFA). The desired fractions were collected, concentrated under reduced pressure and lyophilized to yield the trifluoroacetic acid salt of the title compound 88 (12 mgs) as a tan solid. HPLC Ret. Time=2.76 min (HPLC conditions: Ballistic YMC S5 ODS 4.6×50 mm column with a binary solvent system where solvent A=10% methanol, 90% water, 0.2% phosphoric acid and solvent B=90% methanol, 10% water, and 0.2% phosphoric acid, flow rate=4 mL/min, linear gradient time=4 min, start % B=0, final % B=100). LCMS [M+H]⁺ 382.14.

Examples 89 to 96

Compounds listed in Table 9 were prepared using methods described in Example 88.

TABLE 9

| Ex. No. | G | HPLC ret. Time, min. (column conditions)* | [M + H]⁺ |
|---|---|---|---|
| 89 | phenyl | 2.81 | 352.12 |
| 90 | 2-methylphenyl (CH₃) | 2.95 | 366.17 |
| 91 | 2-fluorophenyl (F) | 2.81 | 370.15 |
| 92 | 4-fluorophenyl (F) | 2.86 | 370.14 |
| 93 | 2-chlorophenyl (Cl) | 2.92 | 386.07 |
| 94 | 2,6-difluorophenyl (F, F) | 2.76 | 388.11 |

TABLE 9-continued

| Ex. No. | G | HPLC ret. Time, min. (column conditions)* | [M + H]+ |
|---|---|---|---|
| 95 | 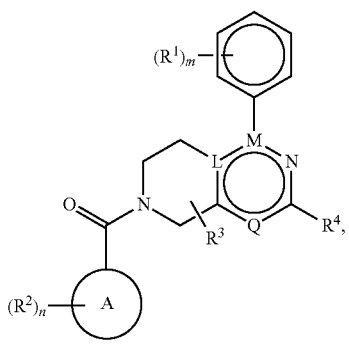 | 2.79 | 412.13 |
| 96 | | 2.83 | 538.32 |

*Ballistic YMC S5 ODS 4.6 × 50 mm column with a binary solvent system where solvent A = 10% methanol, 90% water, 0.2% phosphoric acid and solvent B = 90% methanol, 10% water, and 0.2% phosphoric acid, flow rate = 4 mL/min, linear gradient time = 4 min, start % B = 0, final % B = 100.

What is claimed is:

1. A compound of Formula (I):

(I)

or an enantiomer, diastereomer or a pharmaceutically-acceptable salt thereof, wherein:
Q is a bond, L is —N— and M is —C═;
$R^1$ is selected from the group consisting of halo, halo-$C_1$-$C_3$ alkyl and optionally substituted $C_{1-3}$ alkyl;
$R^2$ is selected from the group consisting of halo, halo-$C_1$-$C_3$ alkyl, optionally substituted $C_{1-3}$ alkyl, $C_1$-$C_3$ alkoxy and —[C(O)]$_2$NR$^7$R$^8$ wherein each of $R_7$ and $R_8$ is independently an optionally substituted $C_1$-$C_3$ alkyl, and further wherein $R_7$ and $R_8$ can be taken together with the atoms to which they are attached to form an optionally substituted 5-6 membered ring;
$R^3$ and $R^4$ are each hydrogen;
ring A is selected from the group consisting of phenyl, indole and pyrrolo[2, 3-b] pyridine;
m is 1 or 2; and
n is 1 or 3;
wherein the optional substituents for $C_1$-$C_6$ alkyl groups are 1-4 groups selected from halo nitro, cyano, hydroxy, alkoxy, haloalkoxy, —O-aryl, —O-heterocyclo, —O-alkylene-aryl, —O-haloalkyl, alkylthio, carboxy, alkoxycarbonyl, alkylcarbonyloxy, carbamoyl, substituted carbamoyl, carbamate, substituted carbamate, urea, substituted urea, amidinyl, substituted amindinyl, aryl, heterocycle, cycloalkyl, —NR$^c$R$^d$, —OC(═O)NR$^c$R$^d$, —C(═O)NR$^c$R$^d$, —NR$^e$C(═O)NR$^c$R$^d$, —NR$^e$C(O)$^2$—NR$^c$R$^d$, —N(R$^e$)S(O)$_2$NR$^c$R$^d$, —N(R$^e$)P(O)$_2$NR$^c$R$^d$, (wherein each of R$^c$ and R$^d$ is independently selected from hydrogen, alkyl, and heterocyclo, and R$^e$ is hydrogen, alky, or phenyl); and —SR$^f$, —S(═O)R$^g$,—S(O)$_2$R$^g$, —NR$^e$S(O)$_2$—R$^g$,—P(O)$_2$—R$^g$,—NR$^e$P(O)$_2$—R$^g$, —NR$^e$C(═O)R$^f$, —NR$^e$C(O)$_2$R$^f$, —OC(═O)R$^f$, —OC(═O)OR$^f$, —C(═O)OR$^f$ or —C(═O)R$^f$ (wherein R$^e$ is defined as immediately above, R$^f$ hydrogen, alkyl, aryl or heterocyclo, and R$^g$ is alkyl, aryl, or heterocyclo); in the aforementioned substituents, in each instance, the alkyl, aryl, heterocyclo or cycloalkyl groups (R$^c$, R$^d$, R$^e$, R$^f$, and R$^g$) in turn an be optionally substituted with one to four, preferably one to three further groups, selected from R$^k$, —O—R$^k$, cyano, nitro, haloalkyl, haloalkoxy, halo, —NR$^k$R$^x$, —OC(═O)NR$^k$R$^x$, —C(═O)NR$^k$R$^x$, —NR$^k$C(═O)R$^x$, —SR$^k$, —S(═O)R$^y$, —S(O)$_2$R$^y$, —OC(═O)R$^k$, —C(═O)OR$^k$, —C(═O)R$^k$, phenyl, benzyl, phenyloxy, or benzyloxy, or a lower alkyl substituted with one to two of —O—R$^k$, cyano, nitro, haloalkyl, haloalkoxy, halo, —NR$^k$R$^x$, —OC(═O)NR$^k$R$^x$, —C(═O)NR$^k$R$^x$, —NR$^k$C(═O)R$^x$, —SR$^k$, —S(═O)R$^y$, —S(O)$_2$R$^y$, —OC(═O)R$^k$, —C(═O)OR$^k$, —C(═O)R$^k$, phenyl, benzyl, phenyloxy, or benzyloxy, wherein R$^k$ and R$^x$ are selected from hydrogen, lower alkyl, hydroxy(lower alkyl), halo (lower alkyl), cyano(lower alkyl), and amino(lower alkyl), and R$^y$ is lower alkyl; and
wherein the optional substituents for an optionally substituted 5-6 membered ring are 1-4 groups selected from alkyl; substituted alkyl; the substituents recited above for substituted alkyl groups, and additionally, in the case of a 5-6 membered heterocyclo, oxo (═O).

2. A compound, or an enantiomer or phamaceutically acceptable salt thereof, selected from:

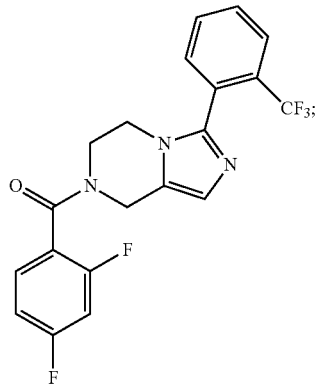

91
-continued
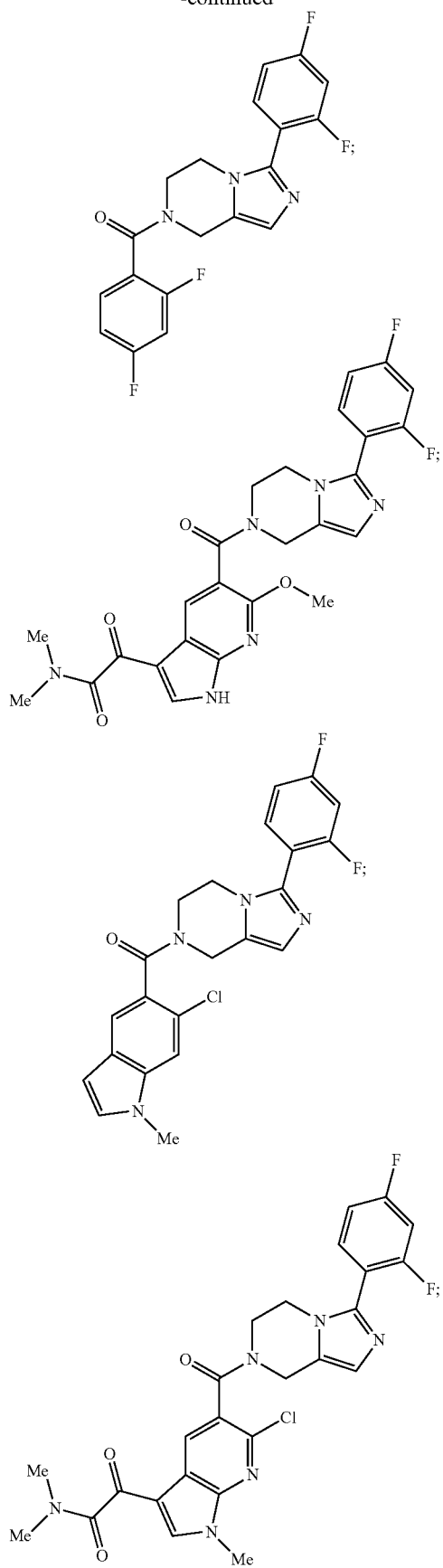
92
-continued
where G is selected from
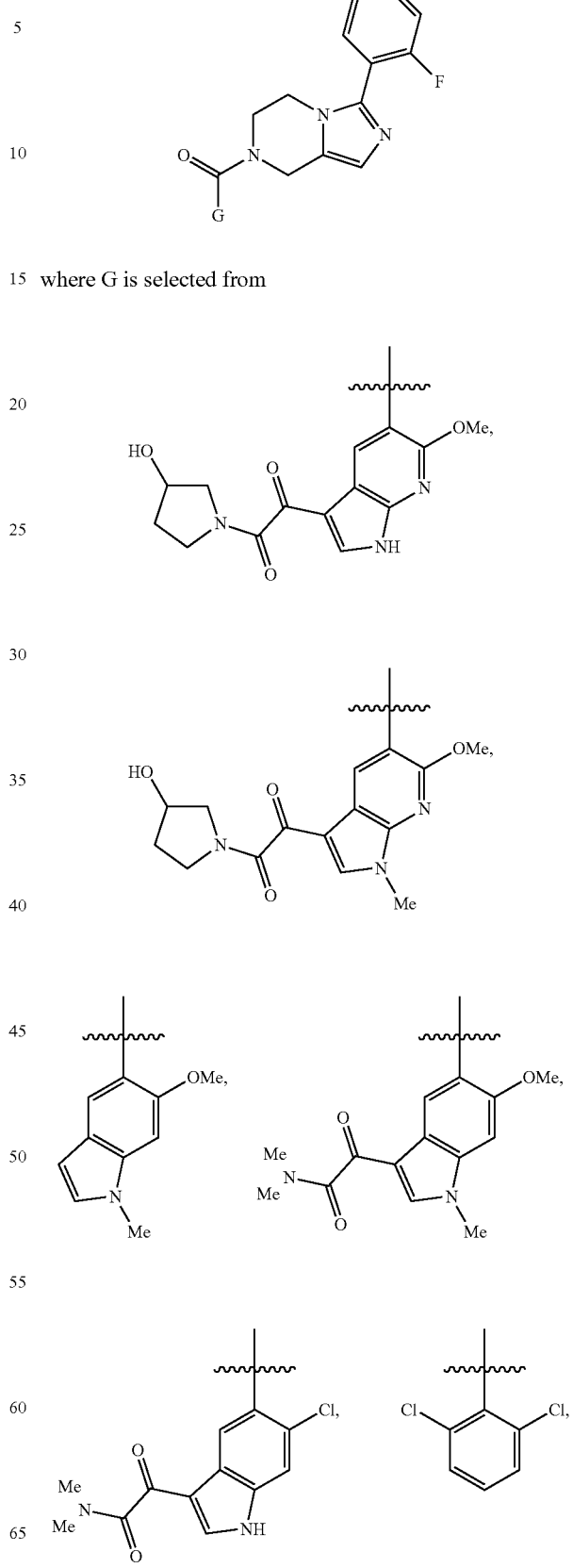

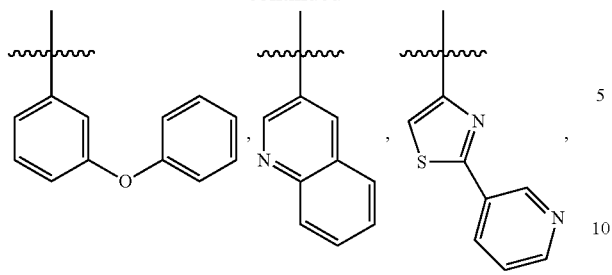
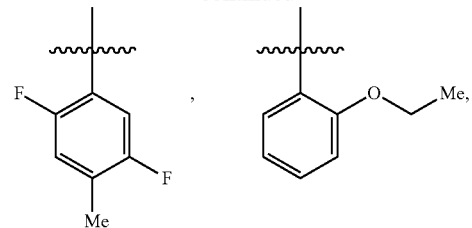
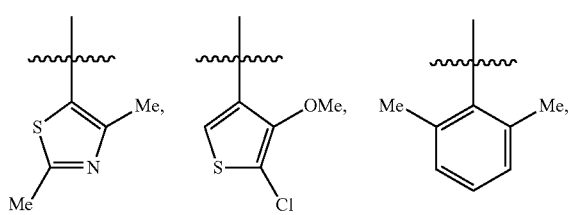
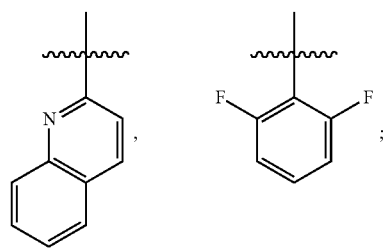
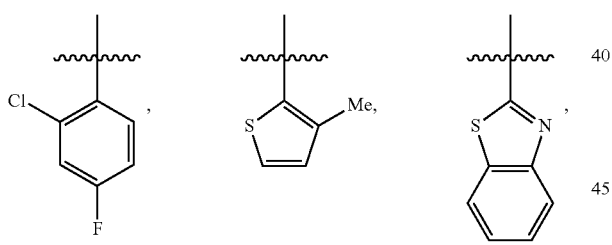
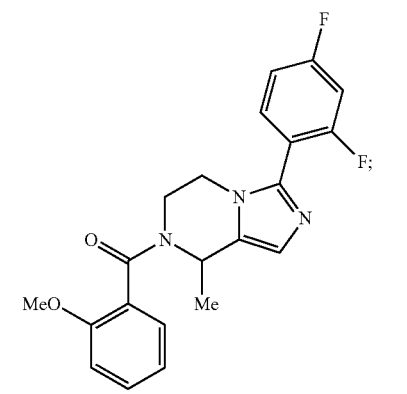
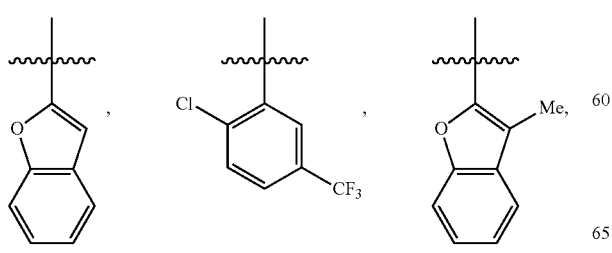
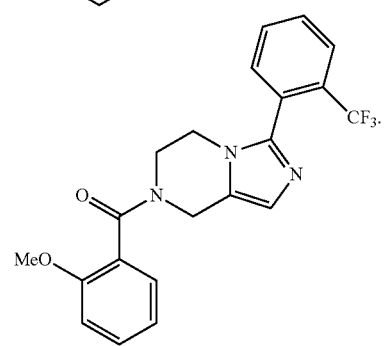

3. A pharmaceutical composition comprising a compound according to claim 1 and a pharmaceutically acceptable carrier or diluent.
4. A compound according to claim 2 selected from the group consisting of:
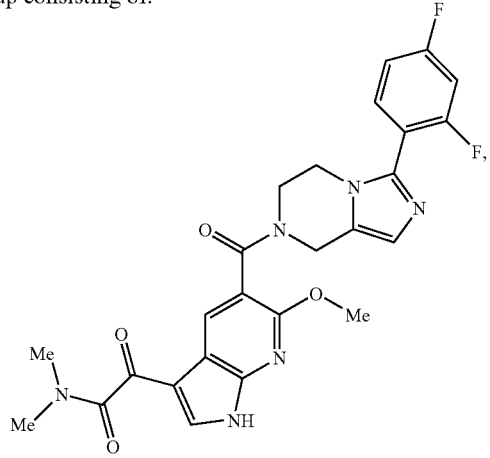
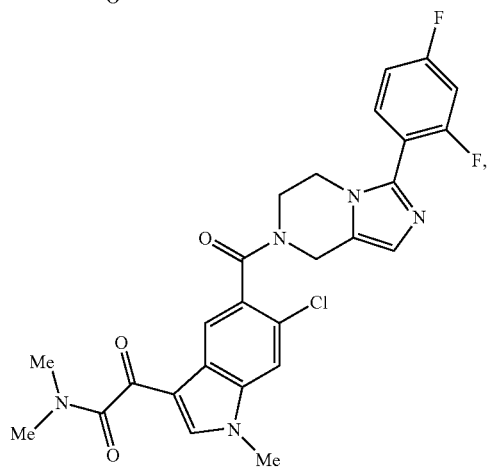
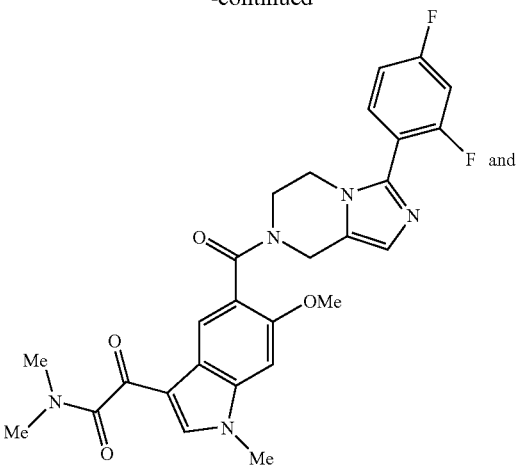
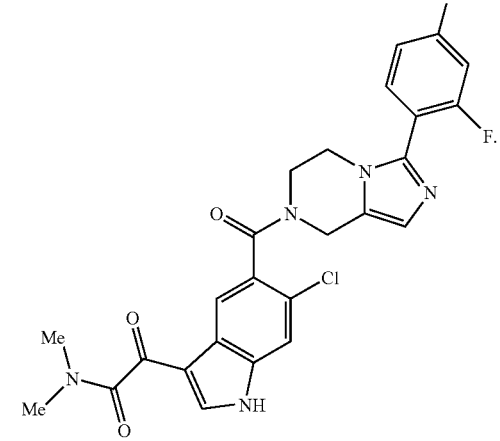
* * * * *

UNITED STATES PATENT AND TRADEMARK OFFICE
CERTIFICATE OF CORRECTION

PATENT NO. : 7,943,617 B2
APPLICATION NO. : 11/940382
DATED : May 17, 2011
INVENTOR(S) : T. G. Murali Dhar et al.

It is certified that error appears in the above-identified patent and that said Letters Patent is hereby corrected as shown below:

In the Claims:

In col. 89, claim 1, line 64, delete "$C_1\text{-}_3$" and insert -- $C_{1\text{-}3}$ --;

In col. 90, claim 1, line 9, delete "halo" and insert -- halo, --;

In col. 90, claim 1, line 14, delete "amindinyl" and insert -- amidinyl --;

In col. 90, claim 1, line 19, after "alkyl," insert -- aryl, --;

In col. 90, claim 1, line 19, delete "alky," and insert -- alkyl, --;

In col. 90, claim 1, line 20, delete "—$S(=O)R^g$,—$S(O)_2R^g$," and insert -- —$S(=O)R^g$, —$S(O)_2R^g$, --;

In col. 90, claim 1, line 21, delete "—$NR^eS(O)_{2-R}{}^g$," and insert -- —$NR^eS(O)_2$—$R^g$, --;

In col. 90, claim 1, line 24, after "$R^f$" insert -- is --;

In col. 90, claim 1, line 28, delete "an" and insert -- can --;

In col. 90, claim 2, line 50, delete "phamaceutically" and insert -- pharmaceutically --; and Signed and Sealed this
Twenty-sixth Day of February, 2013

Teresa Stanek Rea
*Acting Director of the United States Patent and Trademark Office*

CERTIFICATE OF CORRECTION (continued)
U.S. Pat. No. 7,943,617 B2

In the Claims:
In col. 91, claim 2, lines 50-65, delete

" 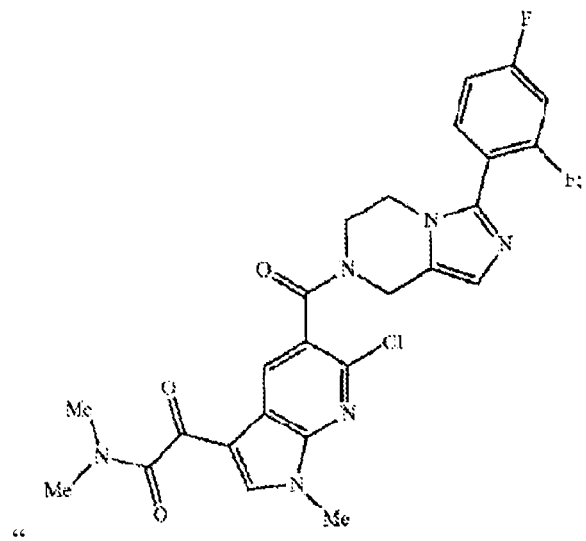 " and insert

-- 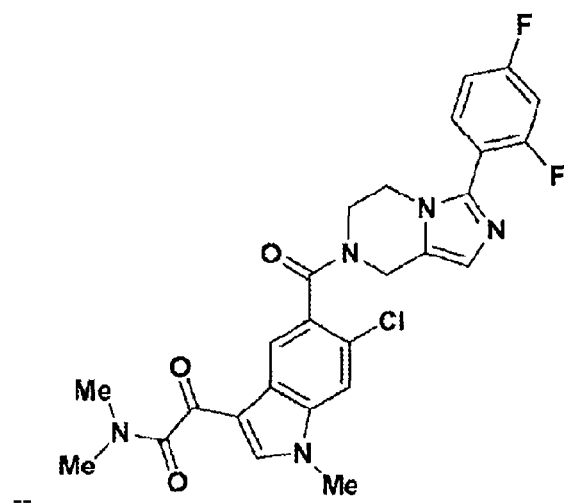 ; --, therefor.